US006265549B1

(12) United States Patent
Altieri et al.

(10) Patent No.: US 6,265,549 B1
(45) Date of Patent: Jul. 24, 2001

(54) METHODS AND COMPOSITIONS FOR INHIBITING ENDOTHELIAL CELL AND FIBRINOGEN MEDIATED INFLAMMATION

(75) Inventors: Dario C. Altieri; Lucia R. Languino, both of La Jolla; George B. Thornton, Ramona, all of CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/347,877

(22) Filed: Jul. 6, 1999

Related U.S. Application Data

(62) Division of application No. 08/748,150, filed on Nov. 12, 1996, now Pat. No. 5,919,754, which is a division of application No. 08/232,532, filed on Apr. 25, 1994, now Pat. No. 5,599,790, which is a continuation-in-part of application No. 08/139,562, filed on Oct. 19, 1993, now abandoned, which is a continuation of application No. 07/898,117, filed on Jun. 11, 1992, now abandoned.

(51) Int. Cl.[7] .................................................. C07K 16/00
(52) U.S. Cl. ..................................... 530/387.9; 530/389.1; 530/388.1
(58) Field of Search .............................. 530/387.1, 388.1, 530/387.9, 389.1

(56) References Cited

FOREIGN PATENT DOCUMENTS

WO 90/03400    4/1990   (WO).

OTHER PUBLICATIONS

Altieri, et al., A Unique Recognition Site Mediates the Interaction of Fibrinogen with the Leukocyte Integrin Mac–1 (CDIIb/CD18), J. Biol. Chem., 265: 12119–12122 (1990).
Altieri, et al., "Oligospecificity of the Cellular Adhesion Receptor MAC–1 Encompasses an Inducible Recognition Specificity for Fibrinogen", J. Cell. Biol., 107: 1893–1900 (1988).
Altieri, et al., "Binding of Fibrinogen to Human Monocytes", J. Clin. Invest., 78: 968–976 (1986).
Altieri, et al., "Occupancy of CDIIb/CD18 (Mac–1) Divalent Ion Binding Site(s) Induces Leukocyte Adhesion", J. Immunol., 147: 1891–1898 (1991).
Erban and Wagner, "A 130–kDa Protein on Endothelial Cells Binds to Amino Acids 15–42 of the BB Chain of Fibrinogen", J. Biol. Chem., 267: 2451–2458 (1992).
Fair, et al., "Immunochemical Mapping of the Conformation of Human Fibrinogen", J. Biol. Chem., 256: 8018–8023 (1981).
Furlan, et al., "Plasmic Degradation of Human Fibrinogen", Biochem. Biophys. Acta, 400: 95–111 (1975).
Hynes, "Integrins: A Family of Cell Surface Receptors", Cell, 48: 549–554 (1987).
Languino, et al., "Fibrinogen–Endothelial Cell Interaction in Vitro; A Pathway Mediated by an Arg–Gly–Asp Recongnition Specificity", Blood, 73: 734–742 (1989).
Pizzo, et al., "The Effect of Plasmin on the Subunit Structure of Human Fibrinogen", J. Biol. Chem., 247: 636–645 (1972).
Price, et al., "In Vivo Inhibition of Neutrophil Function in the Rabbit Using Monoclonal Antibody to CD18", J. Immunol., 139: 4174–4177 (1987).
Ruoslanti and Pierschbacher, "New Perspectives in Cell Adhesion: RGD And Integrins", Science, 238: 491–497 (1987).
Springer, "Adhesion Receptors of the Immune System", Nature, 346: 425–434 (1990).

*Primary Examiner*—Christina Y. Chan
*Assistant Examiner*—Karen Clemens
(74) *Attorney, Agent, or Firm*—Thomas Fitting; Emily Holmes

(57) ABSTRACT

The present invention contemplates therapeutic compositions containing a fibrinogen homolog capable of binding to endothelial cells in an RGD-independent manner that inhibits fibrinogen binding to endothelial cells. Also described are therapeutic compositions containing an ICAM-1 homolog capable of binding to fibrinogen in an RGD-independent manner that inhibits fibrinogen binding to endothelial cells. Methods of inhibiting endothelial cell and fibrinogen mediated inflammation within a patient by administering a homolog of this invention are also contemplated.

2 Claims, 13 Drawing Sheets

```
                                YVAT RDNCCILDER FGSYCPTTCG

IADFLSTYQT KVDKDLQSLE DILHQVENKT SEVKQLIKAI QLTYNPDESS

KPNMIDAATL KSRIMLEEIM KYEASILTHD SSIRYLQEIY NSNNQKIVNL

KEKVAQLEAQ CQEPCKDTVQ IHDITGKDCQ DIANKGAKQS GLYFIKPLKA

NQQFLVYCEI DGSGNGWTVF QKRLDGSVDF KKNWIQYKEG FGHLSPTGTT
           └─────S────S─────────┘
EFWLGNEKIH LISTQSAIPY ALRVELEDWN GRTSTADYAM FKVGPEADKY

RLTYAYFAGG DAGDAFDGFD FGDDPSDKFF TSHNGMQFST WDNDNDKFEG

NCAEQDGSGW WMNKCHAGHL NGVYYQGGTY SKASTPNGYD NGIIWATWKT
     └──S─────S──┘
RWYSMKKTTM KIIPFNRLTI GEGQQHHLGG AKQAGDV
```

FIG. 11

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 411 amino acids
      (B) TYPE: amino acid
      (D) TOPOLOGY: linear (ii) MOLECULE TYPE: protein (ix) FEATURE:
      (A) NAME/KEY: Modified-site
      (B) LOCATION: 88
      (D) OTHER INFORMATION: /note= "SITE OF GLYCOSYLATION"

(ix) FEATURE:
      (A) NAME/KEY: Disulfide-bond
      (B) LOCATION: 153..182

(ix) FEATURE:
      (A) NAME/KEY: Disulfide-bond
      (B) LOCATION: 326..339

(xi) SEQUENCE DESCRIPTION: SEQ ID NO:1:

```
Tyr Val Ala Thr Arg Asp Asn Cys Cys Ile Leu Asp Glu Arg Phe Gly
1               5                  10                  15

Ser Tyr Cys Pro Thr Thr Cys Gly Ile Ala Asp Phe Leu Ser Thr Tyr
            20                  25                  30

Gln Thr Lys Val Asp Lys Asp Leu Gln Ser Leu Glu Asp Ile Leu His
        35                  40                  45

Gln Val Glu Asn Lys Thr Ser Glu Val Lys Gln Leu Ile Lys Ala Ile
50                  55                  60

Gln Leu Thr Tyr Asn Pro Asp Glu Ser Ser Lys Pro Asn Met Ile Asp
65                  70                  75                  80

Ala Ala Thr Leu Lys Ser Arg Ile Met Leu Glu Ile Met Lys Tyr
                85                  90                  95

Glu Ala Ser Ile Leu Thr His Asp Ser Ser Ile Arg Tyr Leu Gln Glu
                100                 105                 110

Ile Tyr Asn Ser Asn Asn Gln Lys Ile Val Asn Leu Lys Glu Lys Val
            115                 120                 125

Ala Gln Leu Glu Ala Gln Cys Gln Glu Pro Cys Lys Asp Thr Val Gln
130                 135                 140

Ile His Asp Ile Thr Gly Lys Asp Cys Gln Asp Ile Ala Asn Lys Gly
145                 150                 155                 160

Ala Lys Gln Ser Gly Leu Tyr Phe Ile Lys Pro Leu Lys Ala Asn Gln
                165                 170                 175

Gln Phe Leu Val Tyr Cys Glu Ile Asp Gly Ser Gly Asn Gly Trp Ile
                180                 185                 190

Val Phe Gln Lys Arg Leu Asp Gly Ser Val Asp Phe Lys Lys Asn Trp
            195                 200                 205

Ile Gln Tyr Lys Glu Gly Phe Gly His Leu Ser Pro Thr Gly Thr Thr
        210                 215                 220

Glu Phe Trp Leu Gly Asn Glu Lys Ile His Leu Ile Ser Thr Gln Ser
225                 230                 235                 240

Ala Ile Pro Tyr Ala Leu Arg Val Glu Leu Glu Asp Trp Asn Gly Arg
                245                 250                 255
```

```
Thr Ser Thr Ala Asp Tyr Ala Met Phe Lys Val Gly Pro Glu Ala Asp
            260                 265                 270

Lys Tyr Arg Leu Thr Tyr Ala Tyr Phe Ala Gly Gly Asp Ala Gly Asp
            275                 280                 285

Ala Phe Asp Gly Phe Asp Phe Gly Asp Asp Pro Ser Asp Lys Phe Phe
            290                 295                 300

Thr Ser His Asn Gly Met Gln Phe Ser Thr Trp Asp Asn Asp Asn Asp
305                 310                 315                 320

Lys Phe Glu Gly Asn Cys Ala Glu Gln Asp Gly Ser Gly Trp Trp Met
            325                 330                 335

Asn Lys Cys His Ala Gly His Leu Asn Gly Val Tyr Tyr Gln Gly Gly
            340                 345                 350

Thr Tyr Ser Lys Ala Ser Thr Pro Asn Gly Tyr Asp Asn Gly Ile Ile
            355                 360                 365

Trp Ala Thr Trp Lys Thr Arg Trp Tyr Ser Met Lys Lys Thr Ile Met
            370                 375                 380

Lys Ile Ile Pro Phe Asn Arg Leu Thr Ile Gly Glu Gly Gln Gln His
385                 390                 395                 400

His Leu Gly Gly Ala Lys Gln Ala Gly Asp Val
            405                 410

(2) INFORMATION FOR SEQ ID NO:2:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:2:

Asn Asn Gln Lys Ile Val Asn Leu Lys Glu Lys Val Ala Gln Leu Glu
1               5                   10                  15

Ala (2) INFORMATION FOR SEQ ID NO:3:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:3:

Asn Asn Gln Lys Ile Val Asn Leu Lys Glu Lys Val Ala Gln Leu Glu
1               5                   10                  15

Ala Cys (2) INFORMATION FOR SEQ ID NO:4:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:4:

Lys Tyr Gly Asn Asn Gln Lys Ile Val Asn Leu Lys Glu Lys Val Ala
1               5                   10                  15
```

```
Gln Leu Glu Ala
        20

(2) INFORMATION FOR SEQ ID NO:5:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:5:

Leu Gly Gly Ala Lys Gln Ala Gly Asp Val
1               5                   10
```

METHODS AND COMPOSITIONS FOR INHIBITING ENDOTHELIAL CELL AND FIBRINOGEN MEDIATED INFLAMMATION

CROSS-REFERENCE TO RELATED APPLICATION

This application is a divisional application of Ser. No.08/748,150, filed Nov. 12, 1996, now U.S. Pat. No. 5,919,754, which is a divisional application of Ser. No. 08/232,532, filed Apr. 25, 1994, now U.S. Pat. No. 5,599,790, which is a continuation-in-part of U.S. patent application Ser. No. 08/139,562 filed Oct. 19, 1993, now abandoned which is a continuation of U.S. patent application Ser. No. 07/898,117 filed Jun. 11, 1992, now abandoned, the disclosures of which are hereby incorporated by reference.

STATEMENT OF GOVERNMENT SUPPORT

This invention was made with government support under Grant Nos. HL 43773 and HL 51372 awarded by the National Institutes of Health.

TECHNICAL FIELD

The present invention contemplates the use of compositions to inhibit fibrinogen binding to endothelial cells for the purpose of inhibiting endothelial cell and fibrinogen mediated inflammation.

BACKGROUND

Adhesion of leukocytes to vascular endothelium is one of the earliest events in a variety of immune-inflammatory reactions. The process participates in vascular occlusions and contributes to atherothrombotic lesions. At the molecular level, leukocyte adhesion to endothelial cells is a redundant mechanism, supported by the regulated recognition of a disparate set of membrane receptors, including integrins, expressed on both leukocytes and resting or cytokine-activated endothelial cells.

Integrins are a functionally and structurally related group of receptors that interact with a wide variety of ligands including extracellular matrix glycoproteins, complement and other cells. Integrins participate in cell-matrix and cell-cell adhesion in many physiologically important processes including embryological development, hemostasis, thrombosis, wound healing immune and nonimmune defense mechanisms and oncogenic transformation. See Hynes, *Cell*, 48:549–554 (1987). The majority of integrins participating in dynamic cell adhesion, bind a tripeptide, arginine-glycine-aspartic acid (RGD), present in their ligand, causing cell adhesion. See Ruoslahti et al., *Science*, 238:491–497 (1987).

Mac-1 (CD11b/CD18) is an integrin receptor found predominantly on macrophages and granulocytes. Like all integrin receptors, Mac-1 is a heterodimeric, transmembrane glycoprotein composed of non-covalently associated alpha and beta subunits.

Mac-1 mediates neutrophil/monocyte adhesion to vascular endothelium and phagocytosis of complement-opsonized particles. Antibodies to the Mac-1 receptor alter neutrophil function in vivo including inhibiting neutrophil migration into inflammatory sites. See Price et al. , *J. Immunol.*, 139:4174–4177 (1987). Mac-1 also functions as a receptor for fibrinogen in a reaction linked to fibrin deposition on the monocyte surface. See Altieri et al., *J. Cell Biol.*, 107:1893–1900 (1988); Wright et al., *Proc. Natl. Acad. Sci. USA*, 85:7734–7738 (1988); Trezzini et al., *Biochem. Biophys. Res. Commun.*, 156:477–484 (1988) and Gustafson et al., *J. Cell Biol.*, 109:377–387 (1989).

Fibrinogen is a complex molecule of approximately 340,000 daltons and consists of three pairs of subunit polypeptides, called the α, β and γ chains. These individual chains are held together by several disulfide bonds. The proteolytic digestion of fibrinogen by plasmin produces fragments A, B, C, D and E, all having a molecular weight of less the 85,000 daltons. See Pizzo et al., *J. Biol. Chem.*, 247:636–645 (1972).

Further proteolytic digestion of fibrinogen by plasmin produces a $D_{30}$ fragment with a molecular weight of about 30,000 daltons containing portions of the α, β and γ chains of fibrinogen. See Furlan et al., *Biochim. Biophys. Acta.*, 400:95–111 (1975).

The deposition of fibrinogen on the leukocyte surface occurs in a variety of inflammatory responses such as delayed type hypersensitivity, incompatible transplant rejection and the physiopathology of vascular obstruction and atherogenesis. See Geczy et al., *J. Immunol.*, 130:2743–2749 (1983); Hooper et al., *J. Immunol.*, 126:1052–1058 (1981); Colvin et al., *J. Immunol.*, 114:377–387 (1975); Hattler et al., *Cell Immunology*, 9:289–295 (1973); Gerrity, R.G., *Am. J. Pathol.*, 103:181–190 (1981) and *Am. J. Pathol.*, 103:191–200 (1981); and Shelley et al., *Nature*, 270:343–344 (1977).

Interactions of fibrinogen on cell surface receptors of endothelial cells have been described.

Languino et al., *Blood*, 73:734 (1989) describe the binding of fibrinogen to endothelial cells by an RGD-dependent mechanism. It is generally believed that the vitronectin receptor is the major endothelial receptor for fibrinogen. Cheresh et al, *Proc. Natl. Acad. Sci. USA*, 84:6471–6475 (1987). Other endothelial cell receptors reported to bind fibrinogen include cell surface bound transglutaminase, and an 130 kilodalton receptor that binds to fibrin peptides. Erban et al., *J. Biol. Chem.*, 267:2451 (1992).

Also on the surface of endothelial cells is an intercellular adhesion molecule 1 (ICAM-1) that has been described by Springer, *Nature*, 346:425–433 (1990), and has been shown to bind the leukocyte integrin LFA-1.

Recently, the interaction of fibrinogen with the Mac-1 receptor of leukocytes has been shown to be a dynamic cell adhesion reaction involving the recognition of the tripeptide RGD within fibrinogen by the Mac-1 receptor similar to the interaction of fibrinogen with the integrin receptors on platelets and endothelial cells. See Altieri et al., *J. Clinic Invest.*, 78:968–976 (1986); Pytela et al., *Science*, 231:1559–1562 (1986); Ruoslahti et al., *Science*, 238:491–497 (1987); Ruoslahti et al., *Cell*, 44:517–518 (1986); and International PCT Application No. PCT/US91/05096.

BRIEF DESCRIPTION OF THE INVENTION

It has now been discovered that fibrinogen binds to both the Mac-1 receptor on leukocytes and to an endothelial cell receptor (ECR), thereby bridging between the leukocyte and the endothelial cell during the process of inflammation. Inflammation arising from this bridging event is referred to as endothelial cell/fibrinogen-mediated inflammation. The ECR is an RGD-independent, fibrinogen specific receptor.

The invention describes novel compositions defining the binding sites for the interaction between ECR and fibrinogen.

Thus, a composition is contemplated comprising a therapeutically effective amount of a substantially pure and pharmaceutically acceptable fibrinogen homolog capable of binding to ECR and inhibiting Fg binding to endothelial cells. In preferred embodiments, ECR is ICAM-1.

A preferred Fg homolog is a polypeptide Fg homolog having an amino acid residue sequence derived from fibrinogen. A preferred polypeptide has a total sequence of from about 17 to 100 amino acid residues in length that includes the fibrinogen γ chain sequence from fibrinogen γ chain residues 117–133, which γ chain sequence is shown in SEQ ID NO 2, and the polypeptide is capable of binding to ICAM-1 and inhibiting fibrinogen binding to endothelial cells, variants thereof, and compositions containing a Fg polypeptide homolog.

Also contemplated is an antibody that immunoreacts with a Fg polypeptide homolog as described herein. The antibody also immunoreacts with fibrinogen and inhibits fibrinogen binding to endothelial cells.

Also contemplated is a composition comprising a therapeutically effective amount of a substantially pure and pharmaceutically acceptable ICAM-1 homolog capable of binding to fibrinogen and inhibiting fibrinogen binding to endothelial cells.

The invention also describes a monoclonal antibody that immunoreacts with ICAM-1, but does not immunoreact with the vitronectin receptor, such that the monoclonal antibody preferentially inhibits fibrinogen binding to stimulated endothelial cells.

A monoclonal antibody is also described that immunoreacts with fibrinogen and that preferentially inhibits fibrinogen binding to stimulated endothelial cells.

Also described is a method of inhibiting fibrinogen (Fg) binding to endothelial cells comprising contacting the endothelial cells with a Fg-binding inhibiting amount of a physiologically acceptable composition comprising a homolog selected from the group consisting of a Fg homolog and an ICAM-1 homolog.

The method is useful for inhibiting fibrinogen/endothelial cell-mediated inflammation in a patient and comprises administering to a patient a therapeutically effective amount of a pharmaceutically acceptable composition comprising a substantially pure homolog selected from the group consisting of a Fg homolog and an ICAM-1 homolog.

The invention also describes a method of detecting the amount of a fibrinogen (Fg) homolog in a liquid sample comprising:

(a) admixing a sample of stimulated endothelial cells with a predetermined amount of a liquid sample containing a Fg homolog and a predetermined amount of labelled Fg homolog to form a competition reaction admixture;

(b) maintaining the reaction admixture for a predetermined time period sufficient for any Fg homolog present in said composition to bind to the endothelial cells and form an endothelial cell:Fg homolog complex and to allow the labelled Fg homolog to bind to the endothelial cells to form a labelled endothelial cell:Fg homolog complex; and (c) assaying for the amount of labelled endothelial cell:Fg homolog complex formed in step (b) thereby detecting the amount of a Fg homolog in the composition.

Also described is a method of screening for compositions effective at inhibiting fibrinogen binding to ICAM-1 comprising the steps of:

a) admixing in an inhibition reaction admixture preselected amounts of a putative inhibitor composition, a fibrinogen homolog, and an ICAM-1 homolog;

b) maintaining the admixture under conditions sufficient for the ICAM-1 homolog to bind to the Fg homolog and form an ICAM-1 homolog:Fg homolog complex; and c) measuring the amount of ICAM-1 homolog:Fg homolog complex formed in step (b), and thereby the effectiveness of the inhibitor composition.

Also described is a method for preparing substantially pure ICAM-1 comprising the steps of:

(a) providing an aqueous detergent composition containing at least ICAM-1;

(b) contacting the ICAM-1-containing composition with a fibrinogen-immobilized matrix comprising fibrinogen affixed to a solid support, wherein the contacting is conducted under conditions sufficient for the ICAM-1 to bind to the fibrinogen and form a solid phase ICAM-1:fibrinogen complex;

(c) washing the solid support and the complex with an aqueous wash buffer comprising $Mg^{++}$, $Mn^{++}$ and an RGD-containing polypeptide under conditions sufficient to elute any proteins bound to fibrinogen in an RGD-dependent manner, wherein the wash buffer is substantially free from $Ca^{++}$; and (d) eluting the ICAM-1 from the solid support using an aqueous buffer comprising $Mg^{++}$, $Mn^{++}$ and EDTA, to form the substantially pure ICAM-1.

BRIEF DESCRIPTION OF THE DRAWINGS

In the drawings, forming a portion of this disclosure.

In lanes 3 and 7, the vitronectin receptor eluted with EDTA from the RGD-Sepharose™ column exhibits the characteristic profile of alpha v/beta 3 under reducing and nonreducing conditions as described in Example 2C. Another integrin beta subunit, beta 1, also shown in lanes 3 and 7, was eluted from the RGD Sepharose™ column with EDTA.

Lanes 1 and 5 show the RGD elution of the flow-through from the first RGD column applied onto the second fibrinogen column. Lane 6 shows the results of EDTA elution following the RGD elution where a single band of approximately 90–95 kD under nonreducing conditions was recovered. Under reducing conditions, the molecular weight of the EDTA-eluted fibrinogen receptor only slightly increased as shown in lane 2.

Figure 3:
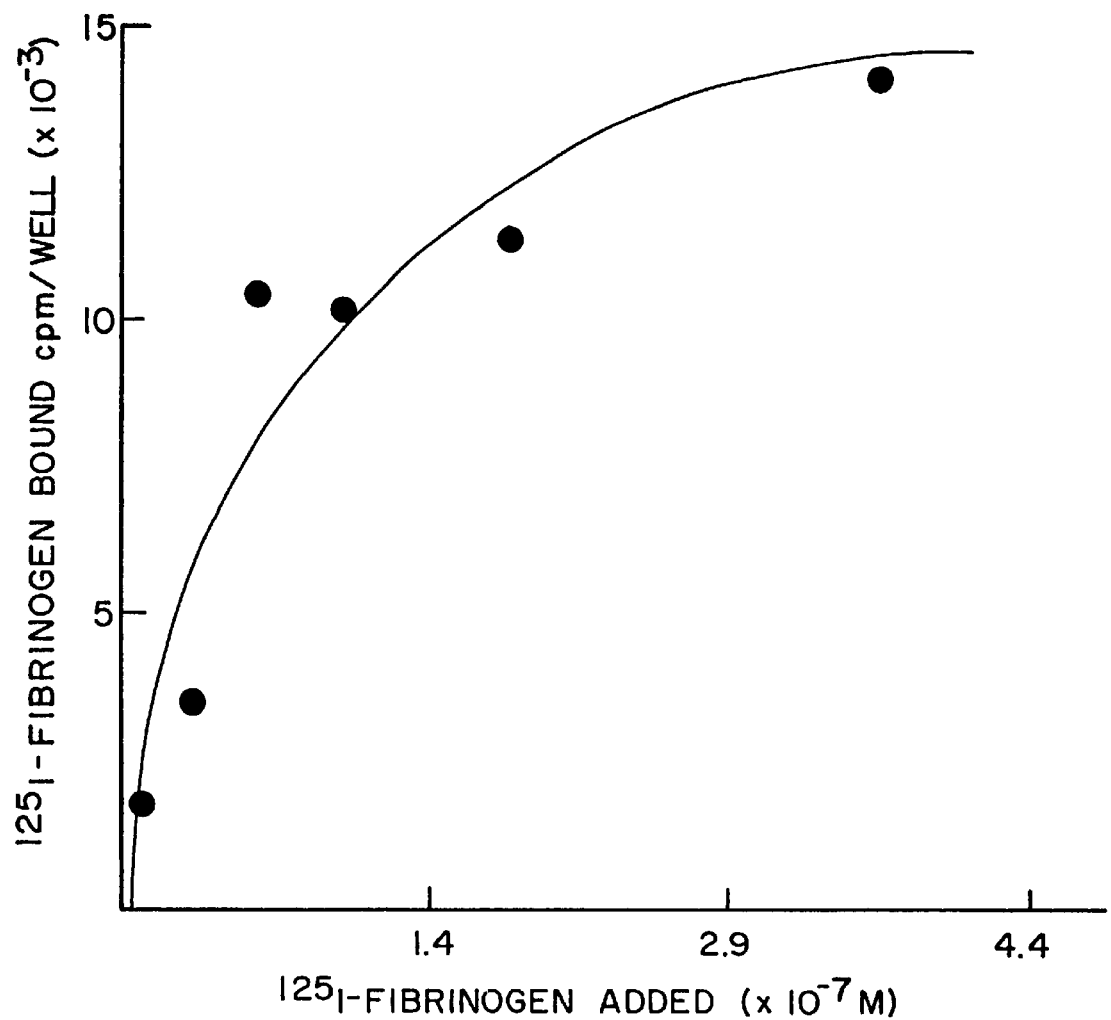

FIG. 3 illustrates the dose-response curve of $^{125}$I-labelled fibrinogen binding to monolayers of HUVEC as described in Example 3A2). The $^{125}$I-labelled fibrinogen bound in counts per minute (cpm) per well (X $10^{-3}$) is plotted on the Y-axis against increasing concentrations of $^{125}$I-labelled fibrinogen (X $10^{-7}$ M) on the X-axis. The data shows that $^{125}$I-labelled fibrinogen binds saturably at a concentration of approximately 0.36 μM to monolayers of unstimulated HUVEC.

Figure 4:
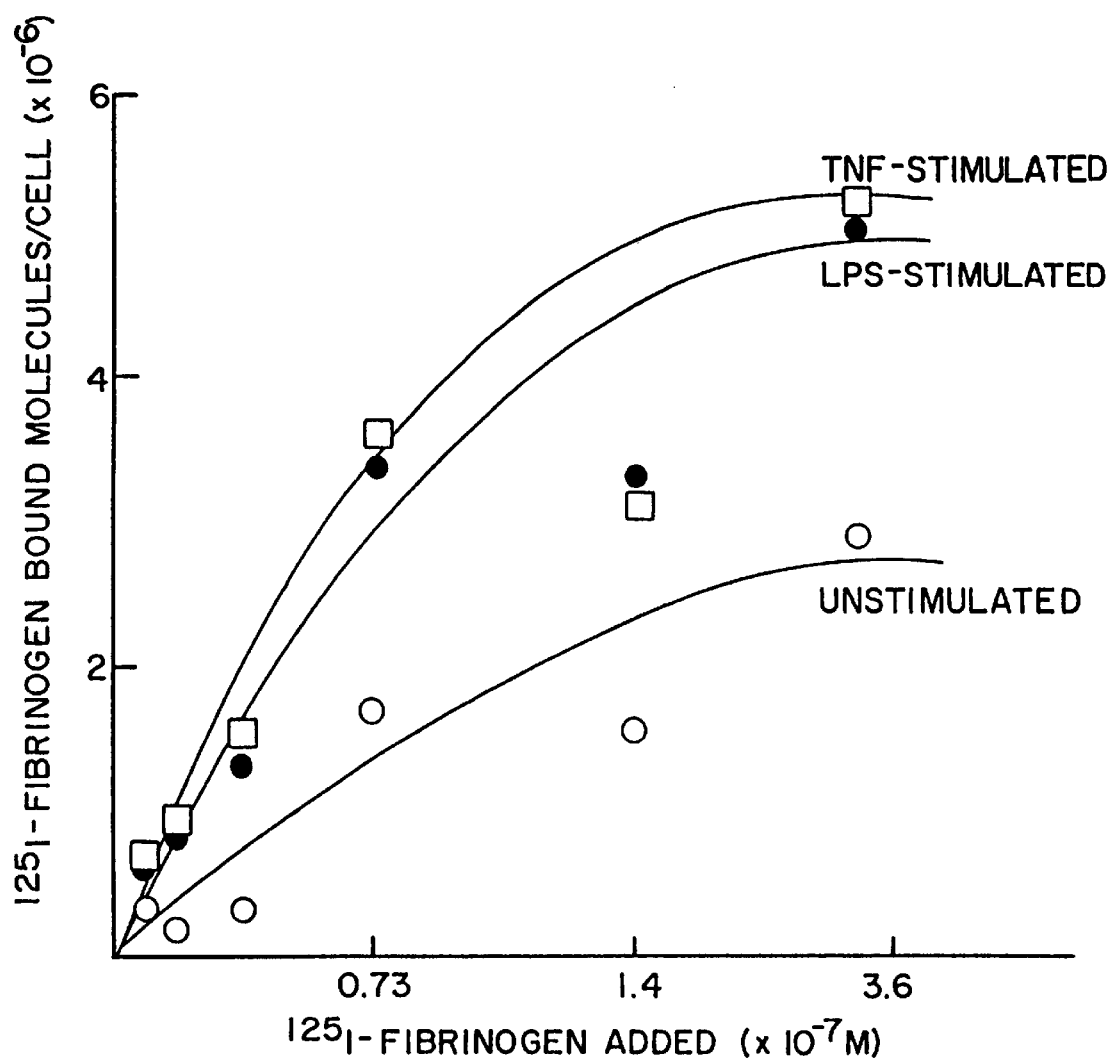

FIG. 4 illustrates the dose-response curve of $^{125}$I-labelled fibrinogen binding to unstimulated and either TNF- or LPS-stimulated HUVEC as described in Example 3A3). $^{125}$I-labelled fibrinogen bound in molecules per cell (X $10^{-6}$) is plotted on the Y-axis against increasing concentrations of $^{125}$I-labelled fibrinogen (X $10^{-7}$ M) on the X-axis. Under stimulation with either TNF or LPS, the number of labelled fibrinogen molecules bound per cell doubled in comparison to those bound to unstimulated cells.

Figure 5:
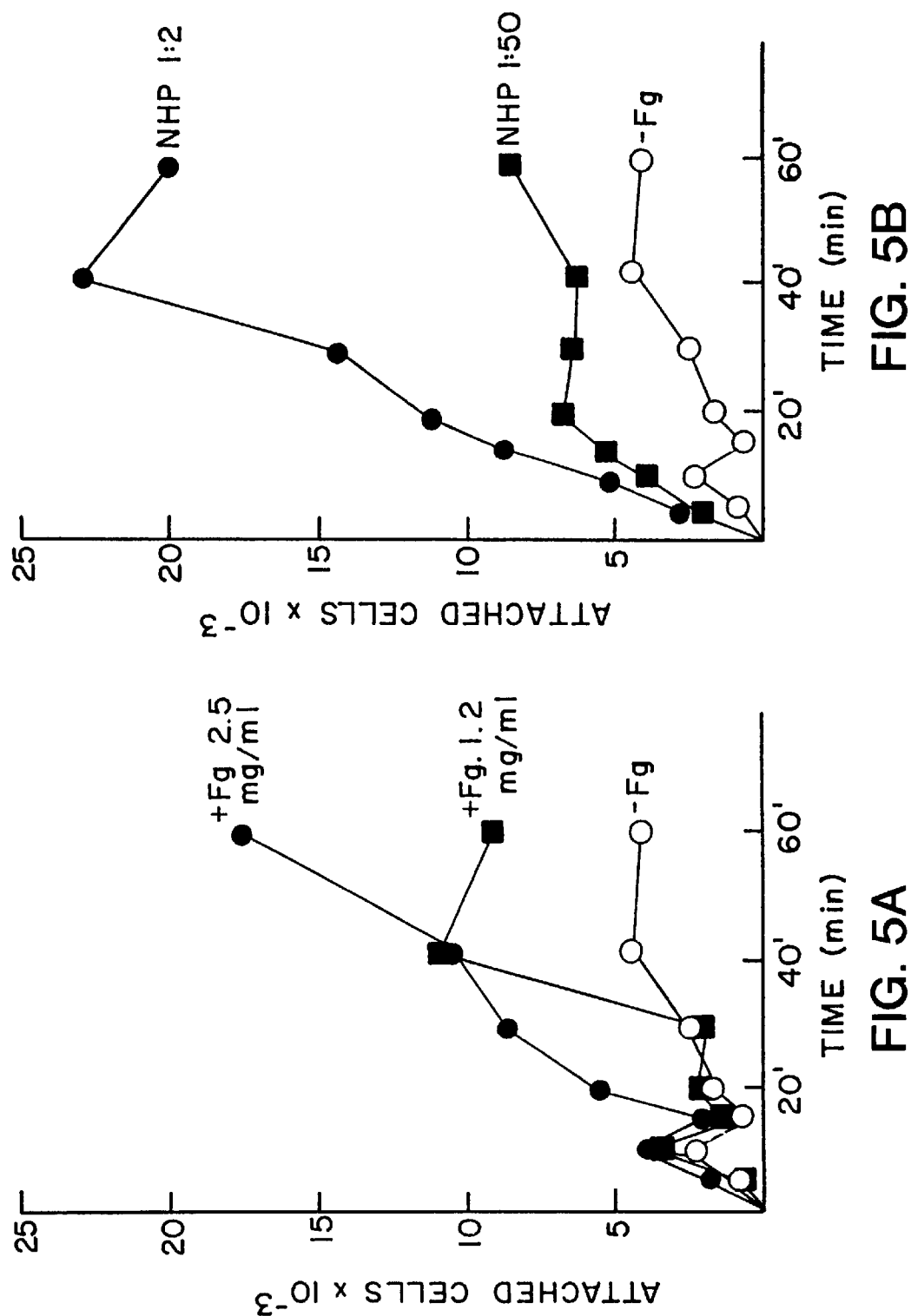

FIGS. 5A and 5B illustrate the dose and time dependent effects on the ability of fibrinogen to mediate the binding of $^{51}$Cr-labelled THP-1 cells to HUVEC. The results of these experiments are shown in FIG. 5A and FIG. 5B where the data is expressed as numbers of $^{51}$Cr-labelled THP-1 cells (X $10^{-3}$) on the Y-axis plotted against the assay time on the X-axis. FIG. 5A shows the effect of different concentrations of purified fibrinogen admixed with THP-1 cells compared to the absence of fibrinogen (labelled as Fg) in mediating the binding to HUVEC cultures over a 60 minute period as described in Example 3B1). FIG. 5B shows results of similar assays done in the presence of dilutions of normal human plasma (NHP).

Figure 6:
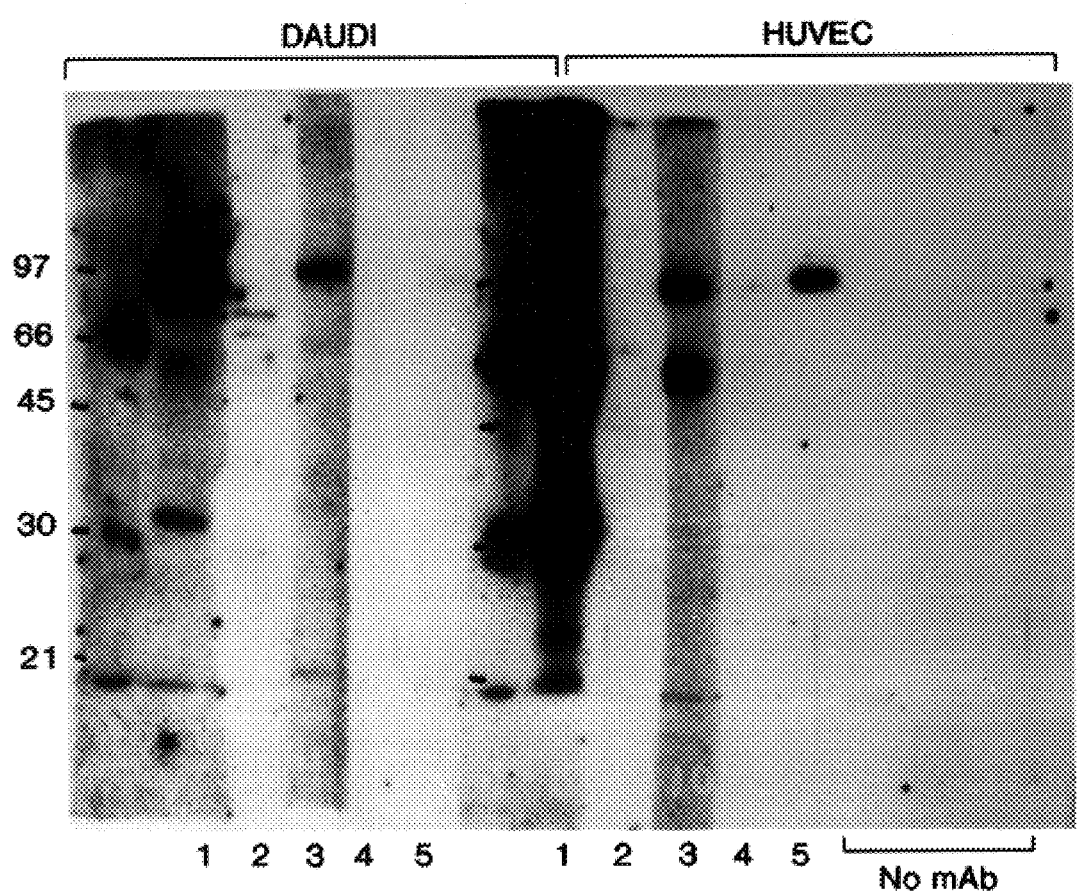

FIG. 6 illustrates the results of the Western blot as described in Example 4E. Radiolabelled molecular weight markers of 97, 66, 45, 30 and 21 kD shown in lane left of the first set of 5 Daudi lanes and left of the second set of 8 HUVEC lanes. Lanes designated 1–5 at the bottom of the blot for both Daudi and HUVEC were respectively immunoreacted with 2E1, PMI-I, affinity purified 14E11, 14E11 culture supernatants and the anti-ICAM-1 BD monoclonal antibodies. The three extra lanes in the HUVEC side of the blot show the nonspecific background when no primary antibody is used.

Figure 7:
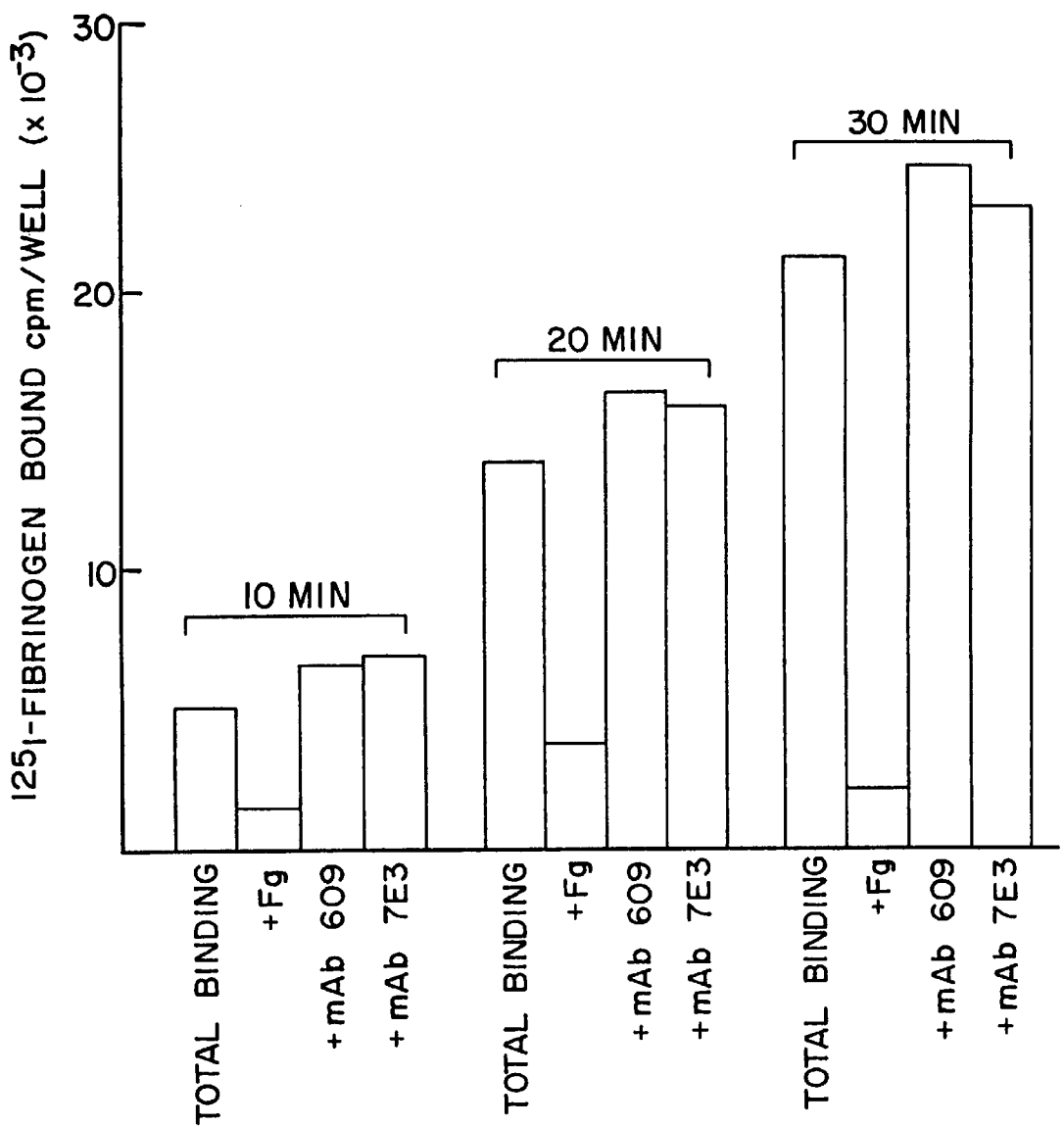

FIG. 7 illustrates in bar graphs the inhibition of binding of $^{125}$I-labelled fibrinogen to HUVEC cultures in the presence of 50 fold excess of unlabelled fibrinogen (Fg) over time as described in Example 5A1). The amount of radioactivity associated with the cells after harvesting is expressed on the Y-axis as cpm/well (X $10^{-3}$). The noninhibitory effects of exposure to the monoclonal antibodies directed against VNR, designated mAb 609 and mAb 7E3, is also shown. Total binding of $^{125}$I-labelled fibrinogen in the absence of admixed inhibitors is also shown.

Figure 8:
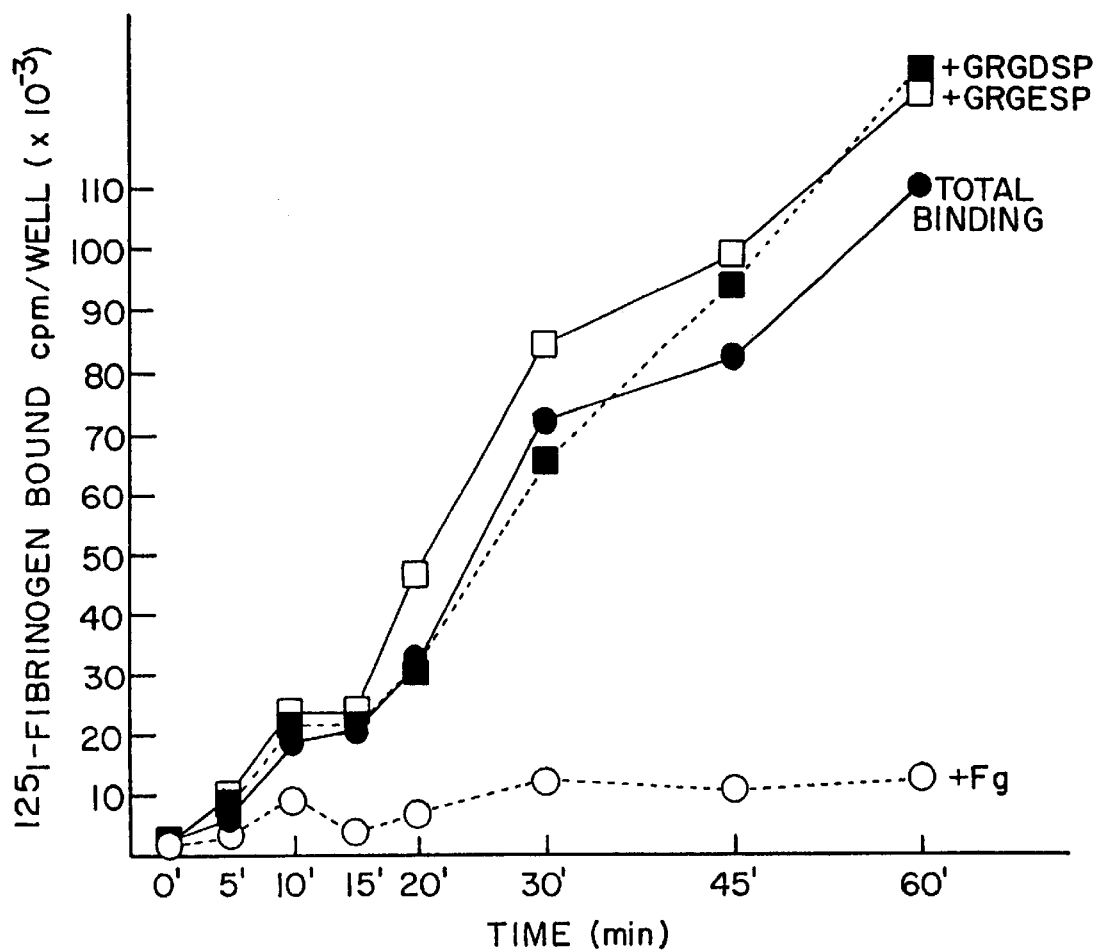

FIG. 8 illustrates the effects of exposure to RGD- and RGE-containing peptides on the binding of 125I-labelled fibrinogen to HUVEC as described in Example 5A1). The amount of $^{125}$I-labelled fibrinogen bound to HUVEC in cpm/well (X $10^{-3}$) is plotted on the Y-axis against the length of time labelled fibrinogen was maintained with HUVEC.

Figure 9B:
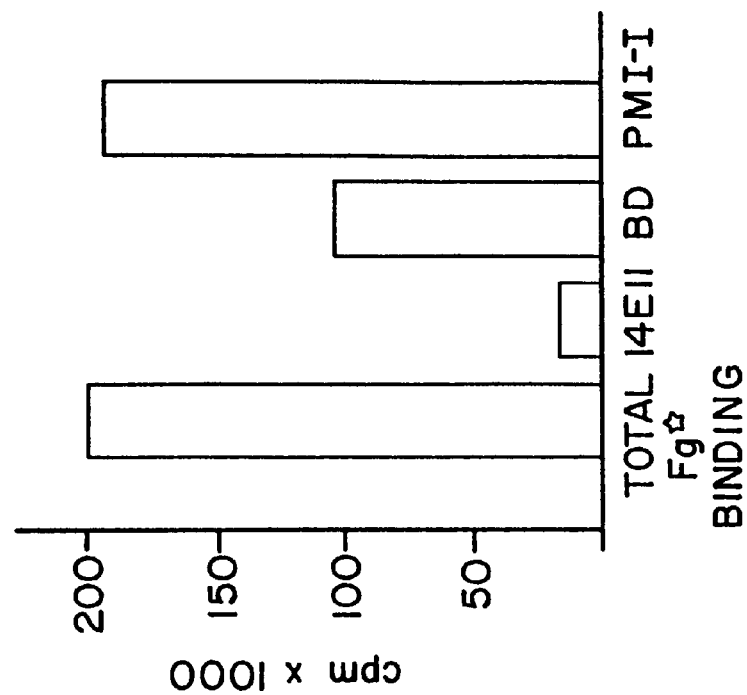
Figure 9A:
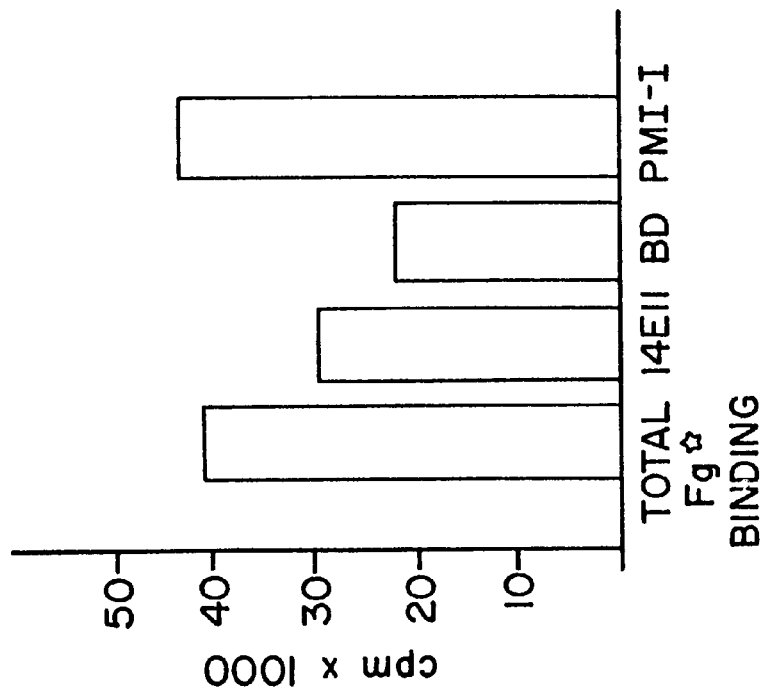

FIGS. 9A and 9B illustrate the inhibition of $^{125}$I-labelled fibrinogen to unst mulated or TNF-stimulated HUVEC cultures, respectively, FIGS. 9A and 9B, by treatment of the HUVEC with the monoclonal antibodies, 14E11, BD (anti-ICAM-1, Becton Dickinson) and a control antibody, PMI-I. The experimental protocol is described in Example 5. The data is expressed in a-bar graph as the specific binding of $^{125}$I-labelled fibrinogen in cpm/well (X $10^{-3}$) on the Y-axis against the specific treatments on the X-axis.

Figure 10A:
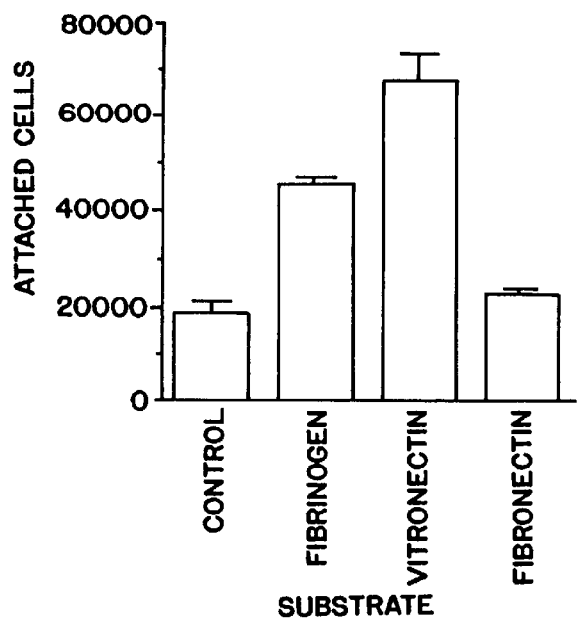
Figure 10B:
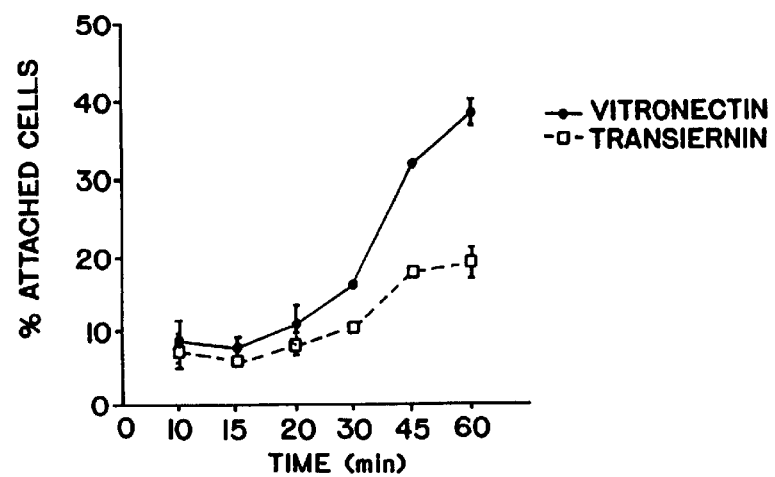
Figure 10C:
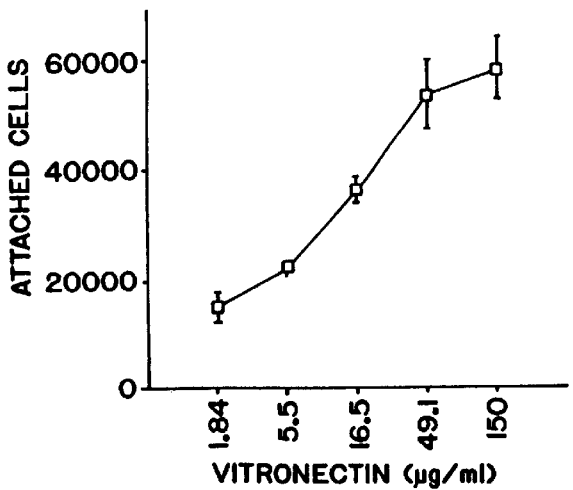

FIGS. 10A–10C illustrate leukocyte-endothelium interaction mediated by the plasma adhesive proteins fibrinogen, vitronectin, and fibronectin. Terminally-differentiated $^{51}$Cr-labeled HL-60 cells were equilibrated with either fibrinogen, vitronectin, or fibronectin prior to incubation with resting HUVEC as described in Example 10C1. The number of HL-60 cells bound to is plotted in a bar graph on the Y-axis (FIG. 10A). Terminally-differentiated $^{51}$Cr-labeled HL-60 cells were equilibrated with either vitronectin or transferrin prior to incubation with resting HUVEC for 10 to 60 minutes as described in Example 10C2. The % HL-60 cells bound is plotted in a bar graph on the Y-axis (FIG. 10B). Terminally-differentiated $^{51}$Cr-labeled HL-60 cells were equilibrated with varying concentrations of vitronectin (1.84 to 150 μg/ml) prior to incubation with resting HUVEC as described in Example 10C3. The numbers of bound HL-60 cells is plotted in a bar graph on the Y-axis (FIG. 10C). Data are the mean±S.D. of triplicates from a representative experiment.

FIG. 11 illustrates the γ-chain amino acid residue sequences of human fibrinogen listed as SEQ ID NO 1. The γ-chain is presented in single letter amino acid code which corresponds to triple letter amino acid code in the Sequence Listing. FIG. 11 represents amino acid residue 1 to amino acid residue 411 in the mature protein. The origin of the γ3 polypeptide (NNQKIVNLKEKVAQLEA, SEQ ID NO 2) is amino acid residue 117 to amino acid residue 133 of the mature γ chain protein. The origin of the L10 polypeptide (LGGAKQAGDV, SEQ ID NO 5) is amino acid residue 402 to amino acid residue 411 in the mature γ chain protein.

Figure 12:
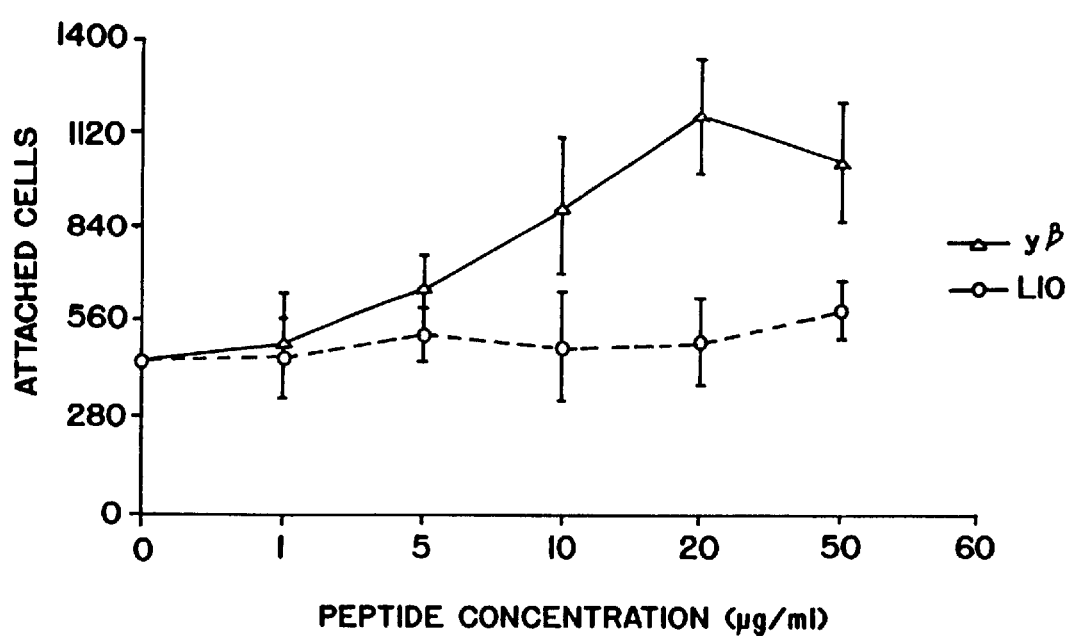

FIG. 12 illustrates the effects of increasing concentrations of polypeptide γ3, represented by open diamonds and polypeptide L10, represented by open circles, on the binding of labeled ICAM-1$^+$ JY lymphocytes. The assay was performed as described in Example 7B. The number of attached cells is plotted on the Y-axis against peptide concentration (μg/ml) plotted on the X-axis. The results demonstrate that JY lymphocytes strongly adhered to immobilized γ3 in a specific and dose-dependent fashion, while control peptide L10 did not support lymphocyte adhesion at any concentration tested under the same experimental conditions.

Figure 13A:
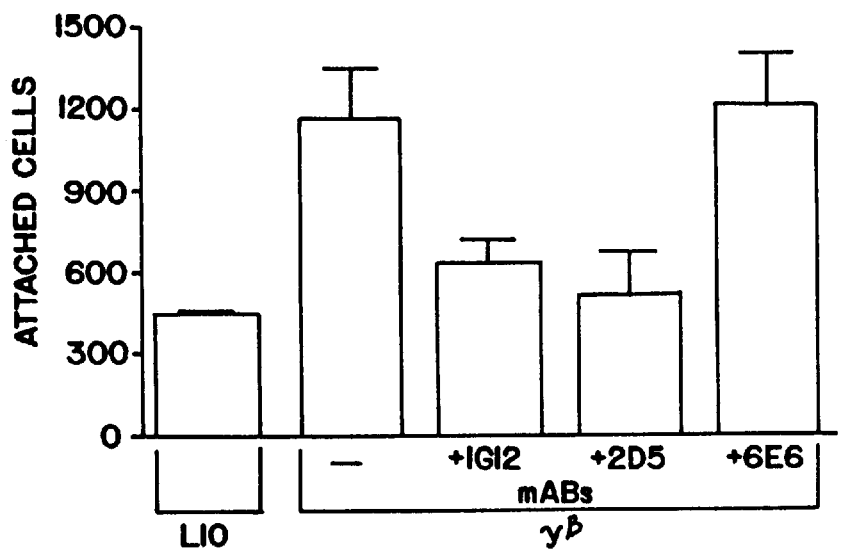

FIG. 13A illustrates the specific attachment of JY lymphocytes to γ3 polypeptide or to control L10 polypeptide in solid phase in the presence of various competitive inhibitors as described in Example 8. The inhibitors used were monoclonal antibodies 1G12 and 2D5 which recognize ICAM-1 and have been shown to block ICAM-1:fibrinogen interaction, monoclonal antibody 6E6 which recognizes ICAM-1 and has not been shown to block ICAM-1:fibrinogen interaction, and monoclonal antibody 6A11which recognizes EPR-1. The number of attached cells is plotted in a bar graph format. 1G12 and 2D5 competitively inhibited the binding of γ3 to JY lymphocytes thus confirming that γ3 contains the receptor binding site of fibrinogen which binds to the ICAM-1 receptor on JY lymphocytes. No binding inhibition occurs with monoclonal antibody 6E6 or 6A11.

Figure 13B:
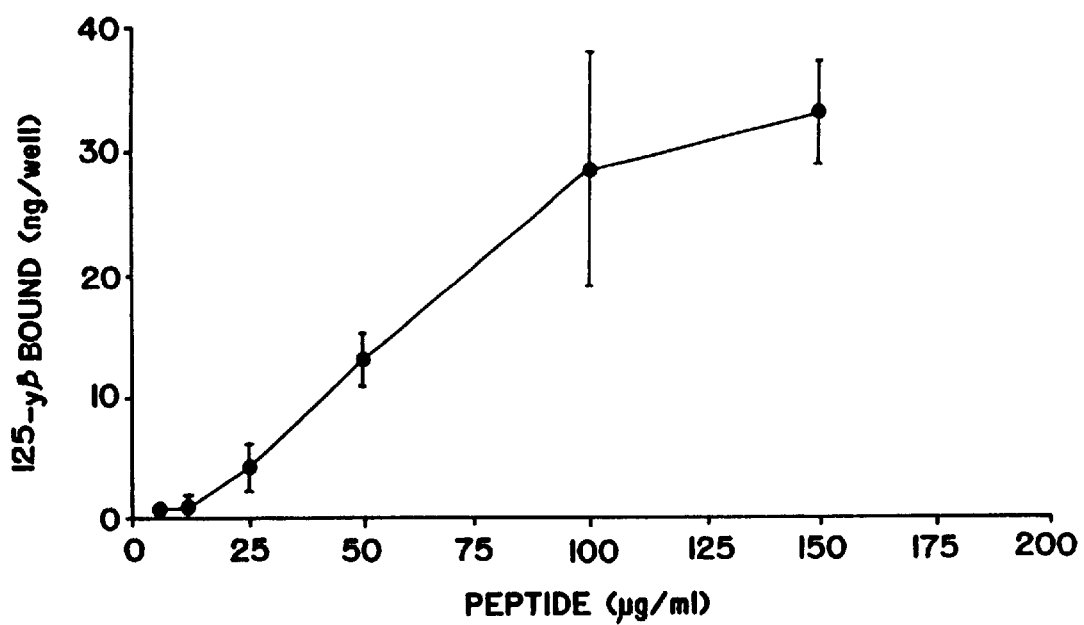

FIG. 13B illustrates the dose-response binding curve of $^{125}$I-labeled γ3 to CHO cells expressing ICAM-1 on their surface. The amount of 125I-γ3 bound in ng/well is plotted on the Y-axis against peptide concentration (μg/ml) plotted on the X-axis. Specific binding is calculated in the presence of 100-fold molar excess of unlabelled γ3 or the irrelevant peptide L10 and is subtracted from the total to calculate the specific binding depicted. Data are the mean±standard error of the mean (SEM) of replicates of a representative experiment.

DETAILED DESCRIPTION OF THE INVENTION

A. General Description

The present invention describes the identification of a novel and specific role for fibrinogen (Fg) in mediating inflammatory processes at endothelial tissues. The role is shown to be a bridging event between the Mac-1 receptor on leukocytes and other Mac-1 receptor-bearing cells and a class of molecules on endothelial cells referred to herein as an endothelial cell receptor (ECR). The interaction of Fg with the ECR is shown to be a unique RGD-independent binding interaction, different from the known binding of Fg to the vitronectin receptor, and to other endothelial cell surface receptors such as transglutaminase or the 130 kilodalton receptor which binds to fibrin-derived peptides.

Insofar as the Fg bridging event described herein adheres Mac-1-bearing cells to endothelial cells, the mechanism discovered and described herein is distinct from the ICAM-1:Mac-1-dependent pathway of leukocyte adhesion, because of the role played by fibrinogen in the present bridging interaction. The Fg-dependent inflammation pathway described herein is referred to as endothelial cell/fibrinogen-mediated inflammation to emphasize the requirement for fibrinogen in the process.

In a related embodiment, the invention describes a related role for vitronectin (Vn) in mediating inflammatory processes at endothelial tissues. This role is shown herein to be a bridging event between leukocytes and endothelial cells. The interaction is shown to be an RGD-independent binding interaction, different from the known binding of Vn to the vitronectin receptor. This vn-dependent inflammation pathway is referred to as endothelial cell/vitronectin-mediated inflammation to emphasize the requirement for vitronectin in the process.

B. Homologs

A homolog, as used herein is a macromolecule, typically a protein or polypeptide, that mimics the structure and function of a domain of a protein after which it is modeled. Where a native protein carries multiple structural domains and thereby mediates multiple distinct functions, as with fibrinogen, a homolog mimics a particular domain and is able to interact and compete with the native protein for participation with the mediators of that protein function in which the domain participates.

1. Fibrinogen Homologs

Thus, according to the present invention, a fibrinogen homolog, or Fg homolog, is a macromolecule that mimics a region of fibrinogen that binds to an endothelial cell receptor (ECR) in an RGD-independent manner according to this invention. The site on ECR to which fibrinogen binds in an RGD-independent manner is referred to as the "ECR RGD-independent Fg-binding site" or "endothelial cell RGD-independent Fg-binding site", that is, a site on endothelial cells, and on the ECR identified herein, that binds to fibrinogen in an RGD-independent manner. The binding site is characterized as RGD-independent because endothelial cells contain other receptors for binding fibrinogen which mediate binding through the RGD-containing region of fibrinogen.

A Fg homolog is any macromolecule which is capable of binding to the ECR RGD-independent Fg-binding site, and thereby can inhibit Fg binding to the ECR RGD-independent Fg-binding site on endothelial cells and consequently inhibit RGD-independent Fg binding to endothelial cells and the inflammation processes resulting therefrom such binding. Assays for measuring the binding of a Fg homolog to the ECR RGD-independent Fg-binding site are described in Example 3a. Assays for measuring the inhibition of Fg binding to the ECR RGD-independent Fg-binding site are described in Example 5.

A preferred Fg homolog is a fragment of fibrinogen that contains the region of Fg that binds to the ECR RGD-independent Fg-binding site. More preferably, the Fg homolog does not bind to the Mac-1 receptor. Such Fg fragments can be proteolytic fragments of Fg, fibrinogen-derived polypeptides, portions of fibrinogen, $D_{30}$, portions of $D_{30}$, polypeptides or proteins homologous to $D_{30}$ or fibrinogen containing non-natural amino acid derivatives or non-proteinaceous side chains, analogs or chemical derivatives of either $D_{30}$, fibrinogen, fragments or polypeptides thereof, and conjugates containing a Fg homolog. A preferred Fg homolog is fibrinogen, a proteolytic fragment of fibrinogen, and particularly the $D_{30}$ fragment of Fg, also referred to as $D_{30}$.

The $D_{30}$ fragment of fibrinogen is produced by proteolytic digestion of fibrinogen. The preparation of $D_{30}$ has been described by Fair et al., *J. Biol. Chem.*, 256:8018–8023 (1981), Furlaw et al., *Biochem. BioPhys. Acta.*, 400:95–11) (1975) and in Example 1. $D_{30}$ contains partially degraded β and γ chains and extensively degraded α chains combined by inter-chain disulfide bonds as described by Pizzo et al., *J. Biol. Chem.*, 247:636–645 (1972). All references and documents cited in this application are hereby incorporated by reference.

The N-terminus of the α chain remnant of $D_{30}$ originates with amino acid residues $Leu^{136}$, $Gln^{137}$, $Lys^{138}$ and $Asn^{139}$ using the amino acid sequence of the alpha chain described by Doolittle et al., *Nature*, 280:464–469 (1979).

The α chain remnant of $D_{30}$ does not contain amino acid residues $Arg^{95}$, $Gly^{96}$ and $Asp^{97}$ (RGD) or the amino acid residues $Arg^{572}$, $Gly^{573}$ and $Asp^{574}$ (RGD) and has a Mw of about 11 to 13 kilodaltons (kDa). The N-termini of the β chain of $D_{30}$ contains amino acid residues $Asp^{134}$, $Asn^{135}$, $Glu^{136}$, and $Asn^{137}$. The N-terminus of the γ chain of $D_{30}$ contains amino acid residues $Met^{89}$, $Leu^{90}$, $Glu^{91}$, and $Glu^{92}$.

Another preferred Fg homolog is a polypeptide derived from fibrinogen, particularly polypeptides having an amino acid residue sequence derived from the ECR binding site on fibrinogen in $D_{30}$ as described herein. Particularly preferred are polypeptides that include an amino acid residue sequence of the fibrinogen (Fg) γ chain from residues 117 to 133 of the γ chain. The Fg γ chain sequence is shown in SEQ ID NO 1, and the region of γ chain from residues 117 to 133 is shown in SEQ ID NO 2.

Preferred Fg homolog polypeptides are short amino acid residue sequences for ease of synthesis, manipulation, storage and versatility of use based on their specific biological properties. In particular, small polypeptides are able to contain (mimic) one but not another binding specificity of Fg, thereby increasing the selectivity and consequent utility of the reagent. A preferred polypeptide has a total sequence length of from about 17 to about 100 amino acids.

Particularly preferred polypeptides are described in the Examples, and include the 17 residue polypeptide corresponding to residues 117–133 of Fg γ chain, and variants of this polypeptide which preserve the basic activity described herein. Terminus-modified polypeptides are described having added residues at the amino and/or carboxy termini. These include the addition of a cysteine (C) residue to the carboxy terminus, shown in SEQ ID NO 3, and the addition of a tripeptide lysine-tyrosine-glycine (KYG) to the amino terminus, shown in SEQ ID NO 4. Thus preferred polypeptides include, and preferably consist essentially of, an amino acid residue sequence selected from the group consisting of SEQ ID NOs 2, 3 and 4.

A subject Fg homolog includes any analog, fragment or chemical derivative of an active fibrinogen polypeptide as defined herein, so long as the polypeptide is capable of inhibiting Fg binding to the ECR RGD-independent Fg-binding site. Therefore, a polypeptide Fg homolog can be subject to various changes, substitutions, insertions, modification and deletions where such changes provide for certain advantages in its use, which changes are summarily referred to as "variants thereof". In this regard, a Fg homolog of this invention can contain one or more changes in the polypeptide so long as the homolog retains its function in one or more of the binding and inhibition assays as defined herein.

The term "analog" includes any polypeptide having an amino acid residue sequence substantially identical to a sequence of a Fg homolog or domain of fibrinogen in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite binding activity.

"Chemical derivative" refers to a polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form 0-acyl or 0-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted or serine; and ornithine may be substituted for lysine. Polypeptides of the present invention also include any polypeptide having one or more additions and/or deletions or residues relative to the sequence of a polypeptide whose sequence is shown herein, so long as the requisite binding activity is maintained.

The term "fragment" refers to any subject polypeptide having an amino acid residue sequence shorter than that the native protein.

When a polypeptide defining a portion of a Fg homolog of the present invention has a sequence that is not identical to the sequence of a portion of fibrinogen, it is typically because one or more conservative or non-conservative substitutions have been made, usually no more than about 30 number percent, more usually no more than 20 number percent, and preferably no more than 10 number percent of the amino acid residues are substituted. Additional residues may also be added at either terminus for the purpose of providing a "linker" by which the polypeptides of this invention can be conveniently affixed to a label or solid matrix, or carrier. Preferably the linker residues do not form Fg homolog epitopes, i.e., are not similar in structure to a Fg homolog.

Labels, solid matrices and carriers that can be used with the Fg homologs of this invention are described hereinbelow.

Amino acid residue linkers are usually at least one residue and can be 40 or more residues, more often 1 to 10 residues, but do not form Fg epitopes. Typical amino acid residues used for linking are tyrosine, cysteine, lysine, glutamic and aspartic acid, or the like. In addition, a subject polypeptide can differ, unless otherwise specified, from the natural sequence of the γ chain of fibrinogen by the sequence being modified by terminal-$NH_2$ acylation, e.g., acetylation, or thioglycolic acid amidation, by terminal-carboxylamidation, e.g., with ammonia, methylamine, and the like.

A polypeptide forming a Fg homolog of the present invention can be prepared using the solid-phase synthetic technique initially described by Merrifield, *J. Am. Chem. Soc.*, 85:2149–2154 (1963). Other polypeptide synthesis techniques may be found, for example, in M. Bodanszky et al., *Peptide Synthesis*, John Wiley & Sons, 2d Ed., (1976) as well as in other reference works known to those skilled in the art. A summary of polypeptide synthesis techniques may be found in J. Stuart and J.D. Young, *Solid Phase Peptide Synthesis*, Pierce Chemical Company, Rockford, Ill., 3d Ed., Neurath, H. et al., Eds., p. 104–237, Academic Press, New York, N.Y. (1976). Appropriate protective groups for use in such syntheses will be found in the above texts as well as in J. F. W. McOmie, *Protective Groups in Organic Chemistry*, Plenum Press, New York, N.Y. (1973).

In general, those synthetic methods comprise the sequential addition of one or more amino acid residues or suitably protected amino acid residues to a growing polypeptide chain. Normally, either the amino or carboxyl group of the first amino acid residue is protected by a suitable, selectively removable protecting group is utilized for amino acids containing a reactive side group such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amid linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence any remaining terminal and side group protecting groups (and solid support) are removed sequentially or concurrently, to provide the final polypeptide. A preferred polypeptide synthesis method is described in the Examples.

Methods and procedures for determining inhibition are well known in the art and include the use of competition assays similar to the antigen competition assays described in *Antibodies: A Laboratory Manual*, Harlow and Lane, eds., Cold Spring Harbor, N.Y. (1988). For example, an unlabelled compound suspected of being a Fg homolog can be used to inhibit the binding of labelled Fg or a labelled Fg homolog to the ECR RGD-independent Fg-binding site of ECR on endothelial cells. The amount of labelled Fg binding to the binding site in the presence or absence of the unlabelled compound would be compared and if the presence of the unlabelled compound inhibits the amount of labelled Fg binding to the binding site, then the unlabelled compound is a Fg homolog. A preferred method for measuring inhibition of Fg binding to ECR is described in Example 5.

Another Fg homolog contemplated by the present invention are antibody molecules which immunoreact with the ECR RGD-independent Fg-binding site. Exemplary antibody molecules are anti-ECR antibodies and anti-ICAM-1 antibodies, defined further herein.

A further Fg homolog contemplated by the present invention is any bifunctional molecule which contains a Fg homolog of this invention, and therefore possesses the biological activity, and uses therefor, of a Fg homolog of this invention. A bifunctional Fg homolog molecule can be, for example, a polypeptide which contains two amino acid residue sequences operatively linked into a single polypeptide that defines both a Fg homolog and another polypeptide function. A preferred bifunctional polypeptide defines both the ECR-binding site on fibrinogen and the Mac-1 binding site on fibrinogen, referred to as an ECR/Mac-1 binding polypeptide.

An ECR/Mac-1 binding polypeptide comprises the amino acid residue sequence defining the ECR binding site, i.e., the Fg γ chain sequence from residues 117 to 133, and further contains the amino acid residue sequence defining the Mac-1 binding site, i.e., the Fg γ chain sequence from residues 190 to 202. A preferred ECR/Mac-1 binding polypeptide has the amino acid residue sequence that comprises residues 117 to 202 of fibrinogen γ.

Alternatively, a bifunctional Fg homolog can be formed using fusion polypeptide technology, so long as the included functional regions include residues 117–133, and residues 190–202.

2. Endothelial Cell Receptor Homologs

An endothelial cell receptor (ECR) homolog, according to the present invention, is a macromolecule that mimics a region of ECR that binds to fibrinogen in an RGD-independent manner. The site on fibrinogen to which ECR binds in an RGD-independent manner is referred to as the "Fg RGD-independent ECR-binding site", that is, a site on Fg that binds to ECR in an RGD-independent manner.

An ECR homolog is any macromolecule which is capable of binding to the Fg RGD-independent ECR-binding site, and thereby can inhibit ECR binding to the Fg RGD-independent ECR-binding site on Fg, and thereby inhibit RGD-independent Fg binding to endothelial cells. Assays for measuring the binding of an ECR homolog to the Fg RGD-independent ECR-binding site are described in Example 3a. Assays for measuring the inhibition of ECR binding to the Fg RGD-independent ECR-binding site are described in Example 5.

A preferred ECR homolog is a substantially purified ECR protein, or a fragment of ECR that contains a region of ECR that binds to the Fg RGD-independent ECR-binding site. A particularly preferred ECR homolog is the ECR protein identified as ICAM-1 in Example 2. Thus, where the species of ECR is ICAM-1, the ECR homolog is referred to herein as an ICAM-1 homolog. Also contemplated ECR homologs are ICAM-1 associated or ICAM-1 related molecules.

An ECR homolog of the present invention may be modified, fragmented, coupled or otherwise manipulated as described herein for a Fg homolog so long as the desirable binding and inhibiting properties are maintained.

Particularly preferred are polypeptides and their analogues derived from the region of ICAM-1 that binds to fibrinogen, particularly a soluble ICAM-1 and functional derivatives thereof. A soluble ICAM-1 for use in a composition or method described herein typically lacks the transmembrane domain that serves as a membrane anchor. ICAM-1 and soluble ICAM-1 compositions suitable for use as an ECR homolog can be prepared by a variety of methods, including the purification methods described in Example 2. Additional preparative methods for ICAM-1 and soluble ICAM-1 are described in the Published EPO Application No. EP 365837 and Published Canadian Application No. 2008368.

Another ECR homolog contemplated by the present invention is an antibody molecule which immunoreacts with the Fg RGD-independent ECR-binding site. Exemplary antibody molecules are anti-Fg antibodies, defined further herein.

A Fg or ECR homolog can be coupled to or conjugated with another protein or polypeptide to produce a homolog conjugate. A homolog conjugate has advantages over a homolog used alone. For example, coupling the homolog to a protein or polypeptide known to contain a second biological function allows the targeting of that second biological function to the location at or near an ECR.

When coupled to a carrier to form what is known in the art as a carrier-hapten conjugate, a homolog of the present invention is capable of inducing antibodies that immunoreact with the homolog. In view of the well established principle of immunologic cross-reactivity, the present invention therefore contemplates antigenically related variants of a Fg or ECR homolog. An "antigenically related variant" is a subject polypeptide that is capable of inducing antibody molecules that immunoreact with a Fg homolog of this invention and with Fg, or with an ECR homolog of this invention and with ECR.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

In other preferred embodiments a homolog is conjugated with a carrier molecule to form a homolog conjugate containing at least one carrier molecule. Typical carriers include Sepharose™, Sephadex™, proteins, polypeptides and the like.

A homolog may also be conjugated to itself or aggregated in such a way as to produce a large complex containing a homolog. A large complex containing a homolog is advantageous because it has new biologic properties such as longer half-life in circulation or greater activity.

3. Vitronectin Homologs

A vitronectin (Vn) homolog, according to the present invention, is a macromolecule that mimics a region of Vn that is capable of binding to endothelial cells in an RGD-independent manner, and in doing so competes with the ability of Vn to mediate leukocyte adhesion onto endothelial cells. The site on endothelial cells to which Vn binds in this embodiment is referred to as an "endothelial cell RGD-independent Vn-binding site", that is, a site on endothelial cells that binds to Vn in an RGD-independent manner.

A Vn homolog is any macromolecule which is capable of binding to the endothelial cell RGD-independent Vn-binding site, and thereby can inhibit Vn binding to the endothelial cell RGD-independent Vn-binding site and consequently inhibit RGD-independent Vn-mediated adhesion of leukocytes onto endothelial cells and the inflammation processes resulting therefrom such binding. Assays for measuring the binding of a Vn homolog to the endothelial cell RGD-independent Vn-binding site are described in the Examples. Assays for measuring the inhibition of Vn binding to the endothelial cell RGD-independent Vn-binding site are also described in the Examples.

A preferred Vn homolog is a fragment of vitronectin that contains the region of Vn that binds to the endothelial cell RGD-independent Fg-binding site. Such Vn fragments can be proteolytic fragments of Vn, vitronectin-derived polypeptides and portions of vitronectin.

C. Compositions Containing Homologs

In one preferred embodiment, the invention contemplates a composition comprising a carrier and a fibrinogen (Fg) homolog according to this invention capable of binding to the ECR RGD-independent Fg-binding site and inhibiting fibrinogen binding to the ECR RGD-independent Fg-binding site. Preferred Fg homologs for use in a composition were described earlier. A particularly preferred Fg homolog for use in a composition is a Fg homolog polypeptide of this invention.

In a related embodiment, the invention contemplates a composition comprising a carrier and an endothelial cell receptor homolog according to this invention capable of binding to the Fg RGD-independent ECR-binding site and inhibiting ECR binding to the Fg RGD-independent ECR-binding site. Preferred ECR homologs, particularly ICAM-1 homologs, for use is a composition were described earlier.

Both of these compositions are useful for inhibiting the binding of Fg to endothelial cells. When practiced in vivo, inhibiting Fg binding to endothelial cells inhibits endothelial cell/fibrinogen-mediated inflammation and the associated disease processes described in more detail elsewhere herein.

The Fg or ECR homolog is typically present in an effective amount, that is, an amount sufficient to be used to inhibit Fg binding to endothelial cells, or an Fg-binding inhibiting amount. Assays for determining effective amounts of a homolog are readily available, such as those described herein, and can be used to determine effective amounts.

The homolog is preferably present in the composition in substantially pure form. Furthermore, the homolog is typically in a physiologically acceptable composition, i.e., a composition compatible with endothelial cells. When formulated for use in vivo, the composition is typically pharmaceutically acceptable, and the amount is referred to as a therapeutically effective amount.

A therapeutically effective amount of a Fg or ECR homolog is an amount that when administered to a patient is capable of inhibiting fibrinogen binding to endothelial cells. Assays for detecting the inhibition of Fg binding to endothelial cells and thereby measuring effective inhibiting amounts of homolog include, but are not limited to the competitive and other binding assays described in Example 5 of this specification.

Preferably, a therapeutically effective amount of a Fg or ECR homolog is an amount that reduces (inhibits) fibrinogen binding to endothelial cells by at least 10 percent, preferably by at least 50 percent, and more preferably by at least 99 percent, when measured in an in vitro assay for fibrinogen binding to endothelial cells. An exemplary in vitro assay to quantitate effective inhibitory amounts of a Fg homolog is described in Example 5. Typically, a composition of this invention contains at least about 0.1 weight percent of homolog in the total weight of the composition.

In one embodiment, a therapeutic composition is useful for inhibiting endothelial cell/fibrinogen mediated inflammation in a patient exhibiting one or more of the conditions associated with inflammation as described further herein. In this embodiment, a therapeutically effective amount is an amount that when administered to a patient is sufficient to inhibiting fibrinogen binding to endothelial cell, thereby inhibiting endothelial cell/fibrinogen mediated inflammation.

Assays for directly detecting the inhibition of endothelial cell/fibrinogen mediated inflammation include, but are not limited to, clinical inspection of symptoms attendant in a patient presenting with inflammation.

Substantially pure, when used in the context of a Fg or ECR homolog, refers to compositions that are enriched in Fg or ECR homolog, and preferably are free of detectable amounts of blood cells, immunoglobulin and albumin proteins, and lipoproteins, and more preferably contains in excess of 99 percent by weight of homolog per total mass in the composition.

In one embodiment, the present invention contemplates compositions, and their methods of use, comprising both an Fg and ECR homolog of this invention in a range of ratios of Fg homolog to ECR homolog. The ratio can be anywhere from vast excesses of Fg homolog relative to ECR homolog, to vast excesses of ECR homolog to Fg homolog, ie, about 0.01:99.00 percent by weight. Preferred ratios range from 10:1 to 1:1. The only impermissible combination of Fg homologs and ECR homologs in a contemplated composition is the admixture of an anti-ECR antibody (Fg homolog) with an ECR homolog, or the admixture of an anti-Fg antibody (ECR homolog) with a Fg homolog, because these particular combinations will cross-immunoreact and neutralize effectiveness.

By pharmaceutically acceptable is meant that a Fg or ECR homolog, when used in a therapeutic composition, does not cause any undesirable physiological effects due to the presence of contaminants. Thus a pharmaceutically acceptable Fg or ECR homolog is free of pharmaceutically unacceptable contaminants such as pyrogens (lipopolysaccharides) and other contaminants such as poisonous chemicals (i.e., sodium azide) and detergents, namely sodium dodecyl sulfate.

The preparation of therapeutic compositions which contain polypeptides or proteins as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is mixed with (dispersed in) inorganic and/or organic carriers which are pharmaceutically acceptable and compatible with the active ingredient. Carriers are pharmaceutically acceptable excipients (vehicles) comprising more or less inert substances when added to a therapeutic composition to confer suitable consistency or form to the composition. Suitable carriers are, for example, water, saline, dextrose, glycerol, ethanol, or the like and combinations thereof. In addition, if desired, the composition can contain minor amounts of auxiliary substances such as wetting or emulsifying agents and pH buffering agents which enhance the effectiveness of the active ingredient.

A therapeutic composition useful in the practice of the present invention typically contains a Fg or ECR homolog formulated into the therapeutic composition as a neutralized pharmaceutically acceptable salt form. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic Fg or ECR homolog-containing composition is conventionally administered parenterally, as by injection of a unit dose, for example. In this way the therapeutic composition can be delivered by a variety of means including intravenous, intramuscular, infusion, oral, intranasal, intraperitoneal, subcutaneous, rectal, topical, or into other regions, such as into synovial fluids. However delivery of a Fg or ECR homolog-containing composition transdermally is also contemplated, such by diffusion via a transdermal patch.

The term "unit dose" when used in reference to a therapeutic composition used in the present invention refers to physically discrete units suitable as unitary dosages for humans, each unit containing a predetermined quantity of active material calculated to produce the desired therapeutic effect in association with the required diluent, carrier or excipient.

In preferred embodiments, a therapeutic composition of the present invention contains an effective amount of a Fg or ECR homolog and is prepared by dispersing the homolog in a sterile solution to form a sterile composition. A sterile composition is well understood in the pharmaceutical arts and is substantially free of microorganisms such as a virus, bacteria or fungus. Typically a composition is made sterile by passing the composition through a filter such as a 0.2 micron filter designed for this purpose.

In other preferred embodiments, a composition of the present invention is optimized to allow the Fg or ECR homolog it contains to be delivered transdermally.

In other preferred embodiments, a composition of the present invention contains an immunologically effective amount of Fg or ECR homolog. An immunologically effective amount of Fg or ECR homolog is an amount sufficient to produce antibodies that immunoreact with the immunized homolog.

D. Antibodies and Monoclonal Antibodies

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of the heavy and light chain variable and hypervariable regions that specifically binds antigen. The site can be reduced to a minimum amount of the complementarity determining regions (CDRs) of the variable regions so long as the antigen-binding property is preserved.

The phrase "antibody molecule" in its various grammatical forms as used herein therefore contemplates both an intact immunoglobulin molecule and an immunologically active portion of an immunoglobulin molecule, i.e., an immunoreactive fragment of an intact immunoglobulin molecule.

Exemplary antibody molecules for use in the methods and systems of the present invention are intact immunoglobulin molecules, substantially intact immunoglobulin molecules and those portions of an immunoglobulin molecule that contain the paratope, including those portions known in the art as Fab, Fab', $F(ab')_2$, F(v), and portions thereof.

Fab and $F(ab')_2$ portions of antibodies can be prepared by the proteolytic reaction of papain and pepsin, respectively, on substantially intact antibodies by methods that are well known. See for example, U.S. Pat. No. 4,342,566, Inbar et al., *Proc. Natl. Acad. Sci. USA*, 69:2659–62 (1972), and Goding, *Monoclonal Antibodies: Principles and Practice*, Academic Press, P118–124 (1983).

Fab' antibody portions are also well known and are produced from $F(ab')_2$ portions followed by reduction of the disulfide bonds linking the two heavy reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

1. Anti-ECR Homolog Antibodies

In one embodiment, the present invention contemplates an anti-ECR homolog antibody, ie, a composition comprising antibody molecules, that immunoreacts with an ECR homolog of this invention at or near the ECR RGD-independent Fg-binding site. Stated differently, and anti-ECR homolog antibody immunoreacts with ECR, is specific for the Fg-binding site on ECR as defined herein and inhibits fibrinogen binding to endothelial cells. A preferred anti-ECR homolog antibody preferentially inhibits fibrinogen binding to stimulated endothelial cells.

A preferred anti-ECR antibody does not immunoreact with vitronectin receptor (VnR), ie, is substantially free of antibody molecules that immunoreact with VnR. More preferably, the antibody does not immunoreact with any RGD-dependent endothelial cell surface receptor, or with transglutaminase or the 130 kilodalton receptor which binds fibrin peptides.

By "preferentially inhibits" is meant that the antibody exhibits more inhibition of Fg binding to endothelial cells that are stimulated than endothelial cells that are not stimulated when assayed on endothelial cells in monolayer, such as is described in Example 5. In other words, a preferred antibody inhibits Fg binding to stimulated endothelial cells at lower antibody doses or resulting in lower Fg binding than the same antibody when tested on non-stimulated endothelial cells. Endothelial cells may be stimulated by a variety of means, including by exposure to cytokines such as TNF and chemoattractant peptides such as N-FMLP.

2. Anti-Fg Homolog Antibodies

In one embodiment, the invention describes an anti-fibrinogen homolog antibody molecule that immunoreacts with fibrinogen or a fibrinogen homolog of this invention.

Preferred anti-Fg homolog antibodies immunoreact with a Fg homolog polypeptide of this invention. Exemplary polypeptides are the polypeptides described earlier having a sequence shown in SEQ ID NOs 2, 3 or 4.

Particularly preferred are anti-Fg homolog antibodies which are immunospecific for the site on Fg that binds to ECR in an RGD independent manner, i.e., the Fg RGD-independent ECR-binding site described herein. This class of antibody specificity is preferred because it allows for the diagnostic and therapeutic advantages described herein for reagents having the selective binding properties related to the Fg RGD-independent ECR-binding site. Thus, a preferred antibody is substantially free of immunoreactivity with other functionally separate sites on fibrinogen, such as the Mac-1 binding site.

The Mac-1 binding site on fibrinogen has been defined by fibrinogen polypeptides as described by Altieri et al in published International PCT Application No. PCT/US91/05096. A polypeptide corresponding to residues 190–202 of the Fg γ chain, and shown at residues 190–202 of SEQ ID NO 1, inhibits $D_{30}$ binding to monocytes, was shown to define the Mac-1 binding site. Therefore, a preferred anti-Fg homolog antibody of this invention does not immunoreact with the polypeptide shown in SEQ ID NO 1 from residues 190 to 202.

By "substantially free" means that an antibody molecule of this invention does not immunoreact with the stated antigen at levels within one order of magnitude, and preferably within two orders of magnitude, of the level of immunoreaction with a species of antigen recited to immunoreact with the antibody molecule when immunoreaction is expressed as an equilibrium constant between bound (immunoreacted) and nonbound antigen.

Antibody reactivity with a stated antigen can be measured by a variety of immunological assays known in the art. Exemplary immunoreaction assays are described herein.

The preparation of antibodies is well known in the art. See, Staudt et al., *J. Exp. Med.*, 157:687–704 (1983), Examples 4 and 6 of the specification or *Antibodies: A Laboratory Manual*, Harlowe and Lane, Eds., Cold Spring Harbor, N.Y. (1988). Briefly, to produce an antibody composition of this invention, a laboratory mammal is inoculated with an immunologically effective amount of a ECR homolog, typically as present in a vaccine or inoculum of the present invention, thereby inducing in the mammal antibody molecules having immunospecificity for the immunogen. The antibody molecules induced are then collected from the mammal and are isolated to the extent desired by well known techniques such as, for example, by immunoaffinity chromatography, or by using DEAE Sephadex™ to obtain the IgG fraction.

To enhance the specificity of the antibody, the antibody molecules are preferably purified by immunoaffinity chromatography using solid phase-affixed immunogen. The antibody is contacted with the solid phase-affixed immunogen for a period of time sufficient for the immunogen to immunoreact with the antibody molecules to form a solid phase-affixed immunocomplex. The bound antibodies are separated from the complex by standard techniques.

A vaccine useful for preparing antibodies of the present invention comprises immunologically effective amounts of both an immunogen and an immunopotentiator suitable for use in mammals.

An immunopotentiator is a molecular entity that stimulates maturation, differentiation and function of B and/or T lymphocytes. Immunopotentiators are well known in the art and include T cell stimulating polypeptides such as those described in U.S. Pat. No. 4,426,324 and the C8-substituted guanine nucleosides described by Goodman et al., *J. Immunol.*, 135:3284–88 (1985) and U.S. Pat. No. 4,643,992.

The word "inoculum" in its various grammatical forms is used herein to describe a composition containing, for example, a Fg homolog or an ECR homolog of this invention as an active ingredient used for the preparation of antibodies of this invention.

When a small molecule such as a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide" and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. An exemplary polypeptide having a cysteine residue at its carboxy terminus for conjugation to a carrier is shown in SEQ ID NO 3.

The techniques of polypeptide conjugation or coupling through activated functional groups presently known in the art are particularly applicable. See, for example, Aurameas, et al., *Scand. J. Immunol.*, Vol. 8, Suppl. 7:7–23 (1978) and U.S. Pat. No. 4,493,795, U.S. Pat. No. 3,791,932 and U.S. Pat. No. 3,839,153. In addition, a site directed coupling reaction can be carried out so that any loss of activity due to polypeptide orientation after coupling can be minimized. See, for example, Rodwell et al., *Biotech.*, 3:889–894 (1985), and U.S. Pat. No. 4,671,958.

Exemplary additional linking procedures include the use of Michael addition reaction products, di-aldehydes such as glutaraldehyde, Klipstein, et al., *J. Infect. Dis.*, 147:318–326 (1983) and the like, or the use of carbodiimide technology as in the use of a water-soluble carbodiimide to form amide links to the carrier. Alternatively, the heterobifunctional cross-linker SPDP (N-succinimidyl-3-(2-pyridyldithio) proprionate)) can be used to conjugate peptides, in which a carboxy-terminal cysteine has been introduced.

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a homolog of this invention, typically as a conjugate linked to a carrier. The effective amount of homolog per unit dose sufficient to induce an immune response to the immunogen depends, among other things, on the species of animal inoculated, the body weight of the animal and the chosen inoculation regimen as is well known in the art. Inocula typically contain homolog concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid homolog-conjugate by dispersing the conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

The anti-homolog specific antibody so produced can be used, inter alia, in the therapeutic and diagnostic methods and systems of the present invention to inhibit fibrinogen binding to endothelial cells, and to detect homologs present in a sample such as a body fluid sample. In particular, the antibodies can be used to monitor the therapeutic fate and half-life of homologs administered according to the therapeutic methods of the invention.

An antibody of this invention is preferably a monoclonal antibody due to the controlled specificity offered by a monoclonal antibody.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line.

The preparation of such antibodies was first described by Kohler and Milstein, *Nature* 256:495–497 (1975). An exemplary hybridoma technology is described by Niman et al., *Proc. Natl. Acad. Sci., U.S.A.*, 80:4949–4953 (1983). Other methods of producing a monoclonal antibody, a hybridoma cell, or a hybridoma cell culture are also well known. See, for example, *Antibodies: A Laboratory Manual*, Harlow et al., Cold Spring Harbor Laboratory, 1988; or the method of isolating monoclonal antibodies from an immunological repertoire as described by Sastry, et al., *Proc. Natl. Acad. Sci. USA*, 86:5728–5732 (1989); and Huse et al., *Science*, 246:1275–1281 (1981). The references cited are hereby incorporated herein by reference.

The hybridoma so prepared produces a supernate that can be screened for the presence of antibody molecules that immunoreact with a homolog of this invention, or for inhibition of fibrinogen binding to endothelial cells as described further herein.

Briefly, to form the hybridoma from which the monoclonal antibody composition is produced, a myeloma or other self-perpetuating cell line is fused with lymphocytes obtained from the spleen of a mammal hyperimmunized with a homolog of this invention as the immunogen.

It is preferred that the myeloma cell line used to prepare a hybridoma be from the same species as the lymphocytes. Typically, a mouse of the strain 129 G1X$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the enzyme linked immunosorbent assay (ELISA) described in Example 4.

A monoclonal antibody of the present invention can also be produced by initiating a monoclonal hybridoma culture comprising a nutrient medium containing a hybridoma that produces and secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/1 glucose, 20 mm glutamine, and 20% fetal calf serum. An exemplary inbred mouse strain is the BALB/c.

The monoclonal antibodies of this invention can be used in the same manner as disclosed herein for antibodies of the present invention.

For example, the monoclonal antibody can be used in the therapeutic, diagnostic or in vitro methods disclosed herein where inhibition of fibrinogen binding to endothelial cells is desired.

A preferred monoclonal antibody immunoreacts with the prototype ECR described herein, namely ICAM-1. The anti-ICAM-1 monoclonal antibody was produced by immunization with endothelial cells, followed by screening for the ability to inhibit Fg binding to endothelial cells, as described in Example 4.

A particularly preferred anti-ICAM-1 monoclonal antibody produced using endothelial cells as the immunogen is the monoclonal antibody produced by the hybridoma 14E11, 16G8, 2E12, or 2B12 that immunoreact with ICAM-1, and inhibit Fg binding to endothelial cells.

Additional anti-ICAM-1 monoclonal antibodies were produced by immunization with Daudi cells, followed by screening for the ability to first immunoreact with endothelial cells, and further screened for the ability to inhibit leukocyte adhesion to HUVEC cells in the presence of Fg binding as described in Example 7.

A particularly preferred anti-ICAM-1 monoclonal antibody produced using Daudi cells as the immunogen is the monoclonal antibody produced by the hybridoma 1G12 or 2D5 that immunoreact with ICAM-1, and are shown herein to inhibit Fg binding to endothelial cells.

Also contemplated are monoclonal antibodies having a binding specificity for the same or cross-reacting epitopes, i.e., immunospecific for the same epitope, on ICAM-1 as the above preferred anti-ICAM-1 antibodies, or derived from the above antibodies. Thus, the present invention contemplates a monoclonal antibody, and immunoreactive fragments thereof, that has the immunospecificity of a monoclonal antibody produced by a hybridoma selected from the group consisting of 14E11, 16G8, 2E12, 2B12, 1G12 and 2D5.

Immunological techniques for determining the immunospecificity of a monoclonal antibody are well known in the art, and can include competition binding studies and other cross-reaction assays. See, for example the immunoassays described in *Antibodies: A Laboratory Manual*, Harlow et al., Cold Spring Harbor Laboratory, 1988.

Also contemplated by this invention is the hybridoma cell, and cultures containing a hybridoma cell that produce a monoclonal antibody of this invention.

Hybridomas 14E11, 16G8, 2E12, and 2B12 have been deposited pursuant to Budapest Treaty requirements with the American Type Culture Collection (ATCC), Rockville, Md., on Jun. 10, 1992, and were assigned accession numbers HB 11064, HB 11063, HB 11062 and HB 11061, respectively.

Hybridomas 14E11, 16G8, 2E12, and 2B12 were deposited in a depository affording permanence of the deposit and ready accessibility thereto by the public upon the issuance of a patent, under conditions which assure that access to the hybridomas will be available during the pending of the patent application to those deemed by the Commissioner to be entitled to such access, and that all restrictions on the availability to the public of the hybridomas as deposited will be irrevocably removed upon the granting of the patent. The deposited hybridomas will be maintained by the ATCC for the term of the patent or 30 years from the date of deposit, whichever is longer, and in all events for at least five years after the date of the last request for access.

E. Methods of Inhibiting Fibrinoaen Binding To Endothelial Cells and Inhibiting Fibrinogen/ Endothelial Cell-Mediated Inflammation The present invention contemplates a method of inhibiting fibrinogen (Fg) binding to endothelial cells by contacting said endothelial cells with a composition containing a Fg or ECR homolog, or both, of this invention dispersed in a physiologically acceptable excipient. The method can be practiced both in vitro and in vivo.

The method requires that an amount of Fg or ECR homolog be used in the contacting as to be effective at inhibiting Fg binding to the endothelial cells, i.e., an Fg-binding inhibiting amount.

As described herein, the use of a Fg homolog or an ECR homolog, or both, exhibit(s) inhibition of Fg binding to endothelial cells because these two reagents mimic, as homologs, their natural counterparts and thereby block the fibrinogen-ECR interaction as identified by the present invention.

In the examples herein, the ECR homolog monoclonal antibody anti-ICAM-1 is as an exemplary reagent for use in a composition for the present method. In another example, the Fg homolog, a polypeptide derived from fibrinogen, is used as an exemplary reagent. However, it should be understood that the invention contemplates the use of any Fg or ECR homolog and is not limited to those specific reagents.

In the method, a physiologically acceptable composition containing a Fg homolog or ECR homolog is contacted with endothelial cells in an a Fg-binding inhibiting amount. Typically the amount is an amount sufficient to contact the cells with a concentration of homolog in the range of about 0.1 to 100 microgram per milliliter (ug/ml).

Insofar as the binding of Fg to endothelial cells mediates fibrinogen and endothelial cell-mediated inflammation, inhibiting Fg binding in vivo provides a therapeutic method for inhibiting inflammation in a patient suffering from, or at risk for, fibrinogen and endothelial cell-mediated inflammation.

Thus, the present invention also contemplates a method of inhibiting fibrinogen/endothelial cell-mediated inflammation in a patient comprising administering to the patient a therapeutically effective amount of a pharmaceutically acceptable composition comprising a substantially pure homolog selected from the group consisting of a Fg homolog and an ICAM-1 homolog dispersed together with a pharmaceutically acceptable excipient (carrier).

Patients in which the inhibition of Fg binding to endothelial cells, and the inhibition of inflammation, would be clinically useful include patients with various types of inflammation, or at risk of inflammation, including but not limited to patients with very recent myocardial infarction (within 40 hours of the acute event) where the Fg or ECR homolog would prevent neutrophil accumulation on exposed tissues due to injury to those tissues, patients with autoimmune responses, general inflammatory or localized inflammatory reactions, glomerular nephritis, delayed type hypersensitivity, psoriasis, autoimmune thyroiditis, multiple sclerosis, rheumatoid arthritis, lupus erythematosis, tissue transplants, graft rejection, reperfusion injury of tissue, and the like inflammatory disorders.

The inhibition of fibrinogen/endothelial cell-mediated inflammation can be detected by measuring changes in the amount of neutrophil accumulation at the site of an inflammation producing injury or wound. For example, the number of neutrophils that accumulate at the site of a sponge placed under the skin can be determined both before and after a Fg or ECR homolog is administered to the patient. See, for example, Price et al., *J. Immunol.*, 139:4174–4177 (1987).

Fibrinogen/endothelial cell-mediated inflammation includes any of the various biological processes mediated lymphocyte having a Mac-1 receptor on its cell surface. Typical biological processes include adhesion of Mac-1 bearing cells to vascular endothelium and specific interactions with extracellular matrix proteins.

In a related embodiment, the invention contemplates methods for inhibiting tumor cell growth, particularly tumor cell adhesion and tumor cell metastasis. This embodiment is based on the established role of endothelial cell ICAM-1 receptor in tumor cell growth and particularly metastasis.

The mechanism of action for inhibition of tumor cell growth and metastasis is based on the inhibition of ability of ICAM-1 to interact with fibrinogen. Such inhibition is conducted as described herein using a Fg or ECR homolog of this invention.

Thus, the present invention also contemplates a method of inhibiting tumor metastasis formation in a patient with tumors comprising administering to the patient a therapeutically effective amount of a pharmaceutically acceptable composition comprising a Fg or ECR homolog of this invention. Particularly preferred are the Fg homolog polypeptides described herein. Dosages and routes of administration are substantially the same as for methods for inhibiting Fg binding to endothelial cells.

A homolog is typically administered according to the present invention as a pharmaceutically acceptable composition in the form of a solution or suspension. However, as is well known, peptides and proteins such as a Fg or ECR homolog can also be formulated for therapeutic administration as tablets, pills, capsules, sustained release formulations or powders. Typically, suitable dosage ranges for an therapeutic composition are of the order of one to hundreds of nanomoles of Fg or ECR homolog per kilogram body weight per minute and depend on the route of administration. In any case, the administered composition contains at least about 0.10% to about 99% by weight of a Fg or ECR homolog per weight of composition, preferably 10%–90% and more preferably 25–75%.

The composition is administered in a manner compatible with the dosage formulation, and in a therapeutically effective amount. The quantity to be administered depends on the subject to be treated, capacity of the subject's blood hemostatic system to utilize the active ingredient, and degree of inflammation inhibition or fibrinogen binding inhibition desired. Precise amounts of active ingredient required to be administered depend on the judgement of the practitioner and are peculiar to each individual.

A therapeutically effective amount of homolog can be expressed as an amount sufficient to produce a final concentration of homolog in a patient's blood. That blood concentration can be determined by an in vitro assay for the homolog in a liquid body sample (e.g., blood), such as is described herein, or can be calculated based on the patient's body weight and blood volume as is well known.

Suitable dosage ranges of a homolog for the therapeutic methods described herein are in the order of about 0.1 to about 20 milligrams, preferably one to ten milligrams of homolog per kilogram of body weight of patient per day, and depending on the route of administration. Stated differently, a therapeutically effective dosage is an amount sufficient to produce an intravascular concentration of in the blood of the patient in the range of about 0.1 to about 100 micrograms/milliliter ($\mu$g/ml), preferably about 10 to about 20 $\mu$g/ml of the active ingredient.

F. Methods of Detecting Homolog

The present invention contemplates any method that results in detecting a homolog by producing a reaction product using a monoclonal antibody, polyclonal antibody, or homolog binding reagent.

Due to the binding interaction of a Fg homolog and an ECR homolog, a Fg homolog binding reagent can be any ECR homolog, and an ECR homolog binding reagent can be any Fg homolog.

Those skilled in the art will understand that there are numerous well known clinical diagnostic chemistry procedures that can be utilized to form and detect such reaction products. Thus, while exemplary assay methods are described herein, the invention is not so limited.

Various heterogeneous and homogeneous assay protocols can be employed, either competitive or non-competitive for detecting the presence and preferably the amount of a Fg or ECR homolog in a tissue or liquid composition.

A Fg or ECR homolog may be detected in any sample such as a solid, liquid or body fluid sample. In preferred embodiments a homolog is detected in body fluid samples include blood, plasma, serum, mucous, sputum and the like.

A homolog may also be detected in vitro or in vivo in various tissues and organs. In preferred embodiments tissue slices or tissue sections may be assayed for the presence and location of a homolog. In other preferred embodiments organs may be assayed in vivo for the presence and to determine the location of a homolog.

Detection of the amount of homolog present in vitro or in vivo is useful because the amount of homolog present correlates with the progress of therapeutically administered homolog present in the patient being analyzed. Thus determination of the amount of homolog present in the patient being analyzed allows the therapeutic administration of a homolog to a patient to be monitored to determine the clinical state of the patient.

In one embodiment the present invention contemplates a method of detecting the presence and preferably the amount, of a Fg homolog in a liquid composition. The steps of this method include:

(1) admixing a sample of endothelial cells with a predetermined amount of a liquid sample containing a Fg homolog and a predetermined amount of labelled Fg homolog to form a competition reaction admixture;

(2) maintaining the reaction admixture formed in step (1) for a predetermined time period sufficient for the Fg homolog present in the liquid composition to bind to the endothelial cells and form a endothelial cell:Fg homolog complex and to allow the labelled Fg homolog to bind the endothelial cells and form a labelled endothelial cell:Fg homolog complex;

(3) assaying for the presence and/or amount of labelled endothelial cell:Fg homolog complex formed in step (2) thereby detecting the presence and/or amount of a Fg homolog in the composition.

A predetermined amount of a liquid composition containing a Fg homolog is a known amount of Fg-containing liquid composition that is useful and easily assayed. This predetermined amount of Fg homolog containing liquid composition has been shown to be useful by performing a series of test assays with an amount of liquid composition containing a known concentration of Fg homolog and is sufficient to allow the assay to be performed. Preferred amounts of a liquid composition are from about 1 microliter ($\mu$l) to about 1000 $\mu$l.

The liquid composition also contains a labelled Fg homolog. A label is an atom or molecule that is either directly or indirectly involved in the production of a detectable signal to indicate the presence of a complex. Any label or indicating means can be linked to or incorporated in an expressed protein, polypeptide, or antibody or monoclonal antibody composition of the present invention, or used separately, and those atoms or molecules can be used alone or in conjunction with additional reagents. Labels include various in vivo labels useful within the body of a patient such as $^{111}$In, $^{99}$Tc, $^{67}$Ga, $^{186}$Re, and $^{132}$I.

The label can be a fluorescent labelling agent that chemically binds to antibodies or antigens without denaturing them to form a fluorescent (dye) that is a useful immunofluorescent tracer. Suitable fluorescent labelling agents are fluorochromes such as fluorescein isocyanate (FIC), fluorescein isothiocyanate (FITC), 5-dimenthylamin-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques in found in Deluca, "Immunofluorescence Analysis", in *Antibody As A Tool*, Marchalonis et al., eds., John Wiley & Sons, Ltd., pp. 189–231 (1982), which is incorporated herein by reference.

In preferred embodiments the label is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di(3-ethyl-4-2-benzthiazoline-G-sulfonic acid) (ABTS).

Radioactive elements are also useful as labels. An exemplary radiolabel is a radioactive element that produces gamma ray emissions. Elements which themselves emit gamma rays, such as $^{124}I$, $^{125}I$, $^{128}I$, $^{131}I$, $^{132}I$, and $^{51}Cr$ represent one class of gamma ray emission-producing radioactive element indicating groups. Particularly preferred is $^{125}I$. Another group of useful indicating groups are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such as indium.

The linking of labels, i.e., labelling of, polypeptides and proteins such as a Fg homolog is well known in the art. For instance, antibody molecules produced by a hybridoma can be labelled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas et al., *Scand. J. Immunol.*, Vol. 8, 7:7–23 (1978), Rodwell et al., *Biotech.*, 3:889–894 (1985), and U.S. Pat. No. 4,493,795, which is incorporated herein by reference. In addition, site directed coupling reactions can be carried out so that the label does not substantially interfere with the ability of the antibody molecules to bind their specific antigen. See, for example, Rodwell et al., *Biotech.*, 3:889–894 (1985).

Alternatively, where polypeptides are used as a homolog, a label can be incorporated by adding amino acid residues to either termini of the polypeptide adapted for labelling. For example, iodinated tyrosine can be used by the addition of a tyrosine residue to the polypeptide. A exemplary labelled polypeptide has the tripeptide KYG added to the amino terminus, with the tyrosine iodinated, using the polypeptide shown in SEQ ID NO 4.

The reaction admixture is maintained for a predetermined time period sufficient for the Fg homolog and the labelled Fg homolog present in the liquid composition to bind to the endothelial cells and form an endothelial cell:Fg homolog complex and a labelled endothelial cell:Fg homolog complex.

The amount of time sufficient for the Fg homolog and the labelled Fg homolog to bind the endothelial cells depends upon several physical parameters including temperature and the concentration of the various reactants. In preferred embodiments, the predetermined time period is from about 1 minute to 24 hours. In more preferred embodiments the predetermined time period is from about 10 minutes to about 1 hour. In the most preferred embodiments, the predetermined time period is from about 15 minutes to 30 minutes. Typically this time period is predetermined to optimize the assay.

Typically the reaction admixture is maintained under biological assay conditions that maintain the activity of the polypeptide and protein molecules including the Fg homolog and the endothelial cell sought to be assayed, and include a temperature range of about 4 degrees C (4° C.) to about 45° C., a Ph value range of about 5 to about 9 and an ionic strength varying from that of distilled water to that of about one molar sodium chloride. Methods for optimizing such conditions are well know in the art.

The presence of labelled endothelial cell:Fg homolog complex formed by maintaining the reaction admixture in step (2) is assayed.

The direct or indirect methods used to assay for the presence of and preferably the amount of labelled endothelial cell:Fg homolog complex formed depend on the particular label used and are well known in the art. For example, the amount of radioactivity in the labelled endothelial cell:Fg homolog complex may be determined as described in Example 5. Alternatively, homogeneous assay methods such as those described in U.S. Pat. No. 4,536,479; U.S. Pat. No. 4,233,401; U.S. Pat. No. 4,233,402 and U.S. Pat. No. 3,996,345, whose disclosures are incorporated herein by reference.

In other preferred embodiments, the present invention contemplates another method of detecting the amount of a Fg homolog in a liquid sample using an Fg homolog binding reagent, ie, an ECR homolog. The steps of this method include;

(1) admixing an ECR homolog with a predetermined amount of a liquid sample containing a Fg homolog to form an binding reaction admixture;

(2) maintaining the binding reaction admixture formed in step (1) for a preselected time period sufficient for the Fg homolog present in the liquid sample to bind to the ECR homolog and form a complex containing Fg homolog and ECR homolog; and (3) determining the amount of the complex formed in step (2), thereby detecting the amount of a Fg homolog within the liquid sample.

A preferred ECR homolog is an anti-Fg monoclonal antibody, and the complex formed is an immunoreaction complex.

In a related embodiment, the invention contemplates a method for the detection of the amount of an ECR homolog in a liquid sample using an ECR homolog binding reagent, ie, a Fg homolog. The method is practiced in the same manner as above, except that an Fg homolog is added as the binding reagent to a sample containing an ECR homolog.

Preferably, the liquid sample containing a homolog is a biological fluid sample such as blood, plasma, serum, sputum, saliva, and the like. Preferably, the amount of liquid sample admixed is known.

For the determining step, it is preferred that the added homolog (Fg homolog for detecting ECR homolog, and ECR homolog for detecting Fg homolog) is labelled, i.e., operatively linked to an indicating means such as an enzyme, radionuclide and the like as described earlier. In this embodiment, the determination is made by detecting the presence/amount of the label in the complex, thereby determining the presence/amount of the homolog in the sample.

In one embodiment, the added homolog is present as part of the solid support, i.e., operatively linked to a solid matrix, so that the reaction admixture formed is a solid and liquid phase, with the objective of "capturing" the sample to be determined.

The reaction admixture is maintained for a predetermined time period sufficient for the homolog present in the liquid sample to bind to the antibody and form a complex containing a homolog to be detected and the added homolog.

Biological assay conditions are those conditions that maintain the biological activity of the reagents and the homolog to be assayed as discussed earlier.

In a preferred embodiment, the amount of homolog in the complex can be determined, either directly or indirectly, using assay techniques well known in the art, and typically depend upon the type of indicating means used.

G. Detection of ECR Receptors In Vivo

A method of detecting the presence and preferably the amount and location of cells having ECR receptors in a mammal is contemplated. An effective amount of a composition containing a physiologically tolerable diluent and an amount of Fg homolog linked to an in vivo indicating means is parenterally administered to a human subject. Parenteral administration includes intramuscular administration, intravenous administration, and administration into other body sites, such as synovial fluid. The amount of composition administered is sufficient to bind a detectable quantity of ECR receptors. In preferred embodiments the Fg homolog is anti-ICAM-1 antibody molecules, or $D_{30}$ fragment.

As used herein, the terms "label" and "indicating means" in their various grammatical forms refer to single atoms and molecules that are either directly or indirectly involved in the production of a detectable signal to indicate the presence of a complex. "In vivo" labels or indicating means are those useful within the body of a human subject. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well known in clinical diagnostic chemistry and constitute a part of this invention only insofar as they are utilized with otherwise novel proteins methods and/or systems.

The linking labels, i.e., labelling of, polypeptides and proteins is well known in the art. For instance, antibody molecules produced by a hybridoma can be labelled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas et al., *Scand. J. Immunol.*, Vol. 8, 7:7–23 (1978), Rodwell et al., *Biotech.*, 3:889–894 (1984) and U.S. Pat. No. 4,493,795.

The subject is then maintained for a predetermined time period sufficient for the Fg homolog to bind to the ECR receptors present on the cells of the human subject and form a ECR:Fg homolog complex. Preferably, this time period has been predetermined to optimize the formation of an ECR:Fg homolog complex.

The subject is then assayed for the presence of and preferably the location of any ECR:Fg homolog complexes formed.

H. Method For Identifying Inhibitors

The present invention also contemplates methods for identifying a composition that inhibits the fibrinogen binding interaction to endothelial cells where the interaction is mediated by the fibrinogen binding site on ECR as described herein.

The method is generally useful for the design of novel therapeutics used in the inhibition of endothelial cell/fibrinogen mediated inflammation, and is particularly useful as a mass screening procedure to identify active inhibitor compounds and formulations.

The invention therefore contemplates a method for identifying a composition which inhibits fibrinogen binding to ECR on endothelial cells, which comprises:

(a) incubating components comprising the composition to be tested together with an ECR homolog and a Fg homolog under conditions which allow the ECR homolog to interact and bind with the Fg homolog; and (b) measuring the interaction of the ECR homolog with the Fg homolog, thereby measuring the capacity of the composition to inhibit the interaction.

A preferred ECR homolog is ICAM-1, and a preferred Fg homolog is Fg, as defined herein.

The measuring can be directed at detecting free Fg homolog, free ECR homolog, or free composition. Alternatively, the measuring can detect the binding interaction of the composition with either the ECR homolog or the Fg homolog. Typically, the binding interaction is measured by detecting a complex formed upon binding.

Conditions sufficient for a binding interaction are generally physiological, and are time temperature and buffer conditions compatible with the binding of fibrinogen onto endothelial cells, as shown in the Examples.

More preferably, the binding interaction is detected in assays where one or the other of Fg homolog and ECR homolog are in the solid phase, and the other is labelled. The measuring comprised detecting the presence, and preferably amount of label in the solid phase, directly indicating the amount of inhibition by the composition.

In a related embodiment, the invention describes a method of screening for compositions effective at inhibiting fibrinogen binding to ECR comprising the steps of:

a) admixing in an inhibition reaction admixture preselected amounts of a putative inhibitor composition, a fibrinogen homolog, and an ECR homolog as defined herein;

b) maintaining said admixture under conditions sufficient for said ECR homolog to bind to said Fg homolog and form an ECR homolog:Fg homolog complex; and c) measuring the amount of ECR homolog:Fg homolog complex formed in step (b), and thereby the effectiveness of said inhibitor composition.

In practicing the method, one of the homologs is labelled and in the liquid phase, and the other homolog is in the solid phase, wherein the measuring involves detecting the amount of label in the solid phase. Other formats are readily apparent.

Preferably, the ECR homolog is purified ICAM-1. More preferably, the ECR homolog is in the solid phase. Still more preferably, the solid phase is a cell on which ECR is located such as an endothelial cell, lymphoid cell, or a recombinant cell capable of expressing recombinant ICAM-1.

Exemplary screening methods are described in Example 5 where antibodies where identified that inhibit Fg binding to endothelial cells. Fg homologs and ECR homologs can also be developed and/or identified by the above methods.

EXAMPLES

The following examples are intended to illustrate, but not limit, the present invention.

1. Preparation of Fibrinogen Analogs

A. Purification of Plasma Fibrinogen

Fibrinogen was isolated from fresh plasma by cold ethanol fractionation procedures. To one volume of plasma, 0.22 volumes of cold 50% ethanol, pH 7.0 was admixed which lowered the temperature to −3 degrees Celsius (−3° C.). The admixture was centrifuged and the resultant precipitate was washed with 0.5 original volumes (OV) of 7% ethanol, pH 6.5 at −3° C. The precipitate was re-collected and dissolved in 0.25 OV of 0.55 M trisodium citrate buffer, pH 6.5 at 30° C. The resultant solution was cooled to 0° C. and the fibrinogen was precipitated by the addition of cold 20% ethanol to a final concentration of 8% to form purified fibrinogen.

To remove any possible contamination of the purified fibrinogen with fibronectin, the purified fibrinogen preparation was passed over a gelatin Sepharose™ 4B column (Pharmacia LKB, Piscataway, N.J.) according to manufacturer's instructions resulting in fibronectin-free fibrinogen.

B. Preparation of $D_{30}$ From Purified Fibrinogen

1) Proteolytic Digestion of Purified Fibrinogen

Fifty milligrams (mg) of purified fibrinogen prepared in Example 1A was dissolved in 1 milliliter (ml) of a TBS buffer solution containing 0.01 M Tris(hydroxymethyl) aminomethane (Tris-HC1), 0.14 M sodium chloride (NaCl), pH 7.4, and was proteolytically digested by Streptokinase-activated plasminogen (plasmin) according to the following procedure.

Streptokinase-activated plasminogen was prepared by admixing plasminogen (KABI, 20 units (U)) to 2 ml of 0.1 M sodium phosphate buffer, pH 7.4 and pre-maintaining for 10 minutes at 37° C. with 500 U of streptokinase (Streptase, Behring). This solution was then admixed at a final concentration of 18 micrograms per ml ($\mu$g/ml) to the solution of purified fibrinogen in 2 M urea.

The admixture was maintained for 2 hours at 37° C. The proteolytic reaction in the admixture was terminated by the addition of 50,000 U/ml trasylol (Sigma Chemical Co., St. Louis, Mo.). The resulting solution of fibrinogen fragments was extensively dialyzed against a solution of TBS for 24 hours at 4° C. The dialysis buffer was changed every 8 hours. The dialyzed solution was then recovered and applied on a Sephadex™ G-100 column (Pharmacia LKB). The column chromatography was performed to separate the fragments resulting from the proteolytic digestion of fibrinogen. The column was prewashed with a running buffer of TBS followed by application of the dialyzed fibrinogen fragments. Fractions of 3 ml were collected and the molecular weights of the separated fragments in the fractions were determined by 10% sodium dodecyl sulfate-polyacrylamide gel electrophoresis (SDS-PAGE) with and without reduction by 3% mercaptoethanol.

Three fragments of different molecular weights were visualized by Coomassie Blue staining of the gel. Fragments X, D, and E had respective molecular weights of approximately 240,000, 85,000, and 50,000 under non-reducing conditions. The fractions corresponding to the three separate peaks were separately pooled, dialyzed against distilled water, and concentrated by lyophilization.

2) Proteolytic Digestion of Fragment D to Produce a $D_{30}$ Homolog

Fibrinogen fragment D with a molecular weight of 80,000 (80 kilodaltons (kD)), purified and concentrated, was proteolytically digested with plasmin in 2 M urea for 24 hours at 37° C. as described in Example 1B. The digestion was terminated and the resultant solution dialyzed as described in Example 1B. The dialyzed solution was recovered and the products of the digestion were isolated by high performance liquid chromatography (HPLC) on a Mono-Q-column (Pharmacia LKB) equilibrated in 0.01 M sodium phosphate, pH 7.0. The fragments were eluted with a solution of 0.01 M sodium phosphate and 1 M sodium chloride, pH 7.0. The purity of the eluted proteins in the collected fractions was assayed on 15% SDS-PAGE under non-reducing conditions. Coomassie Blue staining of the gel revealed a 30 kD fragment of greater than 90% homogeneity. The purified proteolytic digestion product of fragment D having a kD of 30 was designated $D_{30}$. The peak fractions containing $D_{30}$ were pooled and concentrated by lyophilization.

2. Purification of the Endothelial Cell RGD-Independent Fibrinogen Receptor

A. Preparation of an Human Umbilical Vein Endothelial Cell Lysate

Human umbilical vein endothelial cells, (HUVEC) commercially available from Clonetics, San Diego, Calif., were passaged into 40 gelatin-coated T75 tissue culture flasks (Falcon, Thousand Oaks, Calif.) and maintained in endotoxin-free RPMI 1640 (Whittaker M.A. Bioproducts, Walkersville, Md.) supplemented with 10% fetal bovine serum (FBS) (Hyclone, Sterile Systems, Logan, Utah), 25 mM Hepes [4-(2-hydroxyethyl)-1-piperidineethanesulfonic acid] (Calbiochem Boehring, La Jolla, Calif.), 100 $\mu$g/ml penicillin-streptomycin-fungizone (Whittaker), 0.5% endothelial cell growth factor (Biomedical Technologies, Stoughton, Mass.) and 1 mM glutamine (Whittaker). In order to increase the yield of purified endothelial cell receptor (ECR), the cultured endothelial cells, at a density of approximately $5 \times 10^6$ cells/flask, were stimulated 6 hours prior to harvesting by exposure to tumor necrosis factor alpha (TNF, Genzyme Corp., Cambridge, Mass.) at a concentration of 20 ng/ml. The cellular response to TNF was initially revealed in experiments described in Example 3A. After the culture medium was removed, the cells were detached from the flasks with 4 mM ethylenediaminetetraacetic acid (EDTA, Sigma Chemical Co.) at 37° C. for 30 minutes. The detached cell suspensions from all the flasks were pooled and pelleted by centrifugation at 1200 rpm for 10 minutes. The pelleted cells were washed twice with cold phosphate-buffered saline (PBS).

After the final wash, the cells were resuspended in PBS containing 1 millimolar (mM) calcium chloride ($CaCl_2$) and 1 mM magnesium chloride ($MgCl_2$) in preparation of labelling cell surface proteins with 4 mCi of sodium $^{125}$iodide ($^{125}$I) (NEN Du Pont de Nemours, Wilmington, Del.) by the lactoperoxidase iodination method known to one skilled in the art and as described in "Antibodies: A Laboratory Method", Eds Harlow et al., Cold Spring Harbor Laboratory, pp 434–435 (1988). After the labelling procedure, the cells were washed 3 times with PBS lacking all cations. After the final centrifugation wash, the pellet was frozen, thawed then resuspended in a volume of 3 parts Tris-buffered saline extraction buffer (TBS extraction buffer) to 1 part pellet. TBS extraction buffer consisted of 25 mM Tris-HCl, 136 mM NaCl and 2 mM potassium chloride (KCl) that also contained 1–2 mM $MgCl_2$, 1–2 mM manganese chloride ($MnCl_2$), 50 mM octyl beta glucopyranoside, 1 mM phenylmethylsulfonyl-fluoride (PMSF), 1 $\mu$g/ml aprotinin, 1 $\mu$g/ml leupeptin, 1 $\mu$g/ml pepstatin and 1 $\mu$g/ml alpha 2 macroglobulin. The preferred concentrations of $MgCl_2$ and $MnCl_2$ were 1 mM. Calcium chloride was absent from the extraction buffer and all subsequent buffers used in the isolation and purification of the ECR.

The resultant cell lysate having 3 ml was centrifuged at 3000×g to pellet the insoluble cellular debris. The supernatant containing the isolated ECR was removed and labelling efficiency was determined by gamma detection. Approximately a specific activity of 200,000 counts per minute (cpm) per 10 microliters ($\mu$l) was obtained by the labelling procedure.

B. Purification of Labelled ECR by Affinity Chromatography on a Fibrinogen Sepharose™ Column 1) Sequential Elutions of Fibrinogen Affinity Column The labelled cell supernatant prepared above was precleared prior to purification by chromatography over a plain Sepharose™ CL4B column (Pharmacia) previously equilibrated with the TBS extraction buffer. For purification of the ECR by affinity chromatography, the flow-through containing the labelled ECR was collected from the plain Sepharose™ column and loaded onto a fibrinogen Sepharose™ column prewashed with 10 column volumes of TBS extraction buffer. The column was previously prepared by coupling 8 mg of purified fibrinogen prepared in Example 1A to one ml (approximately 0.333 grams of resin) of cyanogen bromide-activated (CNBr) Sepharose™ 4B according to manufacturer's instructions (Pharmacia LKB). The labelled ECR-containing solution was maintained on the fibrinogen column overnight at 4° C. and was mixed occasionally to immobilize the ECR on the fibrinogen ligand. Following the maintenance period, the flow-through was collected and stored separately at 4° C.

The column was then washed with 10 column volumes of TBS extraction buffer. Prior to the EDTA elution of the ECR immobilized on the fibrinogen column, the column was first maintained with 300 µl of a 1 mg/ml Arg-Gly-Glu (RGE) peptide solution dissolved in TBS extraction buffer to elute nonspecifically immobilized labelled proteins. The collection of the eluate was followed by a 10 minute waiting period before the next application of 300 µl of the RGE solution to the column. The elution with RGE was repeated 10 times for a total of 10 collected fractions. For the second set of elutions to remove contaminating fibrinogen-bound labelled vitronectin receptor, a member of the integrin superfamily, the column was maintained with 300 µl of a 1 mg/ml Arg-Gly-Asp (RGD) peptide solution dissolved in TBS extraction buffer. The RGD eluate was collected and the elution protocol was repeated 10 separate times as described for the RGE elution resulting in the collection of labelled vitronectin receptor over 10 fractions. Peak fractions were determined by gamma detection. The peptides used for the above-described elutions were synthesized using the classical solid-phase technique described by Merrifield, Adv. *Enzymol.*, 32:221–296 (1969) as adapted for use with a model 430 automated peptide synthesizer (Applied Biosystems, Foster City, Calif.). Prepared polypeptide resins were cleaved by hydrogen fluoride, extracted and analyzed for purity by high-performance liquid chromatography (HPLC) using a reverse-phase C18 column manufactured by Waters Associates, Milford, Mass.

Labelled ECR bound to the then vitronectin receptor-free fibrinogen column was then eluted with 10–20 mM EDTA dissolved in TBS extraction buffer. The 20 mM EDTA elution was preferred. The elution protocol was performed as described above resulting in the collection of purified ECR over 10 separate fractions. Peak fractions containing the eluted $^{125}$I-labelled ECR were determined by gamma detection. The column was then washed with 10 column volumes of TBS extraction buffer followed by 3 column volumes of 1 M NaCl in TBS. The column was stored at 4° C. after a final wash with at least 20 column volumes of PBS containing 0.02% sodium azide.

2) Characterization of the Purified Fibrinogen-Specific ECR

Figure 1:
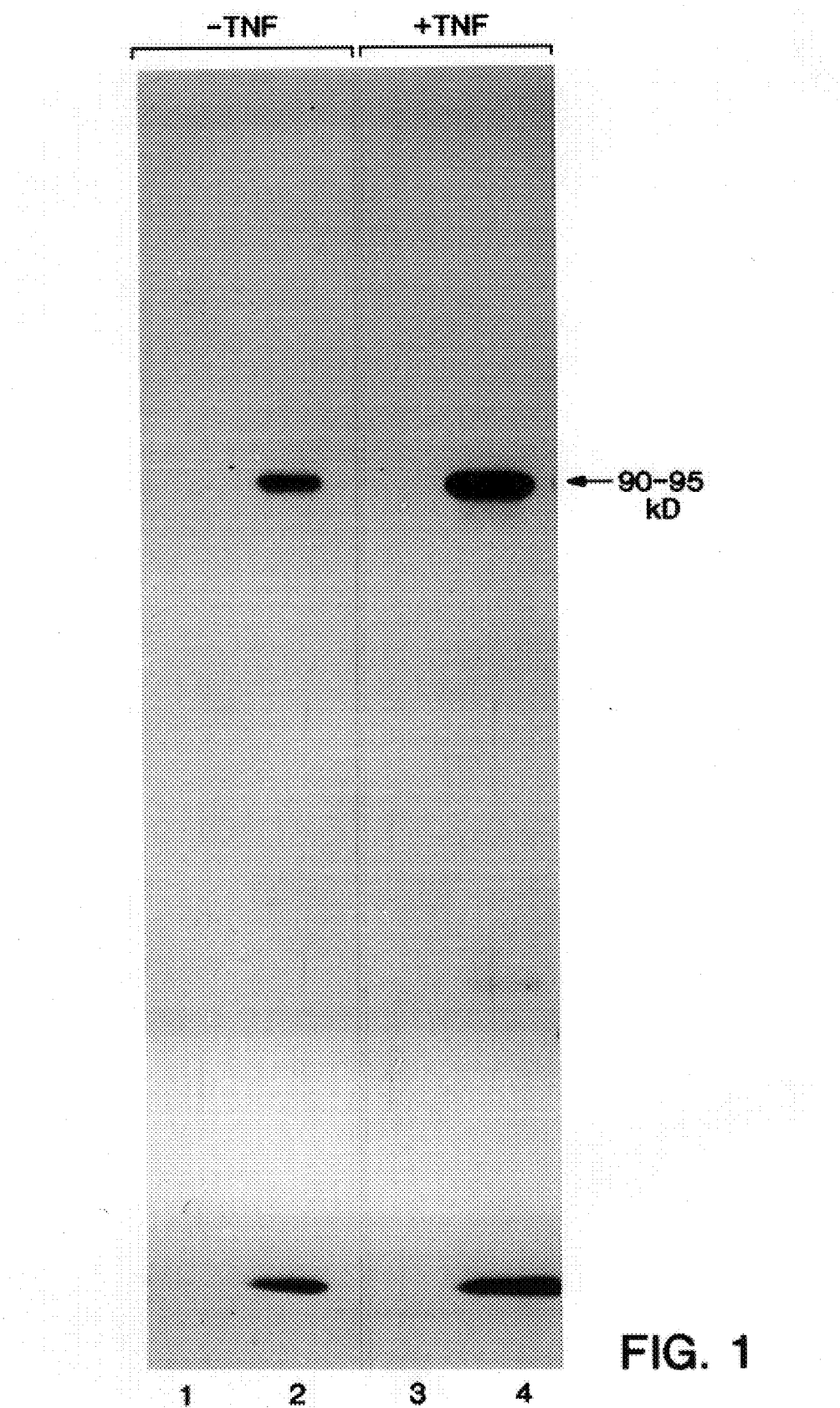
FIG. 1 illustrates the autoradiographic results of electrophoresis of aliquots of peak fractions from both the RGD and EDTA elutions of cell lysate supernatants prepared from cells either left untreated or treated with TNF as described in Example 2A. Lanes 1 and 3 show the RGD-eluted receptors isolated from cell lysates respectively prepared from untreated or TNF-treated cells. The characteristic pattern of VNR is present in lane 3. Lanes 2 and 4 respectively show the EDTA-eluted ECR isolated from untreated and TNF-treated cells having a molecular weight band of approximately 90–95 kD, the intensity of which is enhanced about 3–5 fold as a result of the induction of ECR expression by exposure to TNF.

The molecular weight of the fibrinogen Sepharose™-purified $^{125}$I-labelled ECR was determined by 7.5% SDS-PAGE with and without reduction with 3% beta-mercaptoethanol. FIG. 1 shows the autoradiographic results of electrophoresis of aliquots of peak fractions from both the RGD and EDTA elutions of cell lysates prepared from cells either left untreated or treated with TNF as described in Example 2A. Lanes 1 and 3 show the RGD-eluted receptors isolated from cell lysates respectively prepared from untreated or TNF-treated cells. No bands are detectable in lane 1. However, in lane 3, two bands corresponding to the approximate molecular weights of 125 and 110 kD are present. These bands respectively correspond to alpha v and beta 3 subunits of the vitronectin receptor as described by Cheresh et al., *Proc. Natl. Acad. Sci.*, 84:6471–6475 (1987), hereby incorporated by reference. Lanes 2 and 4, respectively EDTA-eluted ECR isolated from untreated and TNF-treated cells, reveal the presence of a lower molecular weight band of approximately 90–95 kD, the intensity of which is enhanced about 3–5 fold as a result of the induction of ECR expression by exposure to TNF. Thus, the EDTA-eluted fractions contained a non-RGD dependent ECR having a molecular weight of 90–95 kD distinct from the vitronectin receptor that binds to fibrinogen via the RGD tripeptide sequence (Cheresh et al., supra).

C. Purification of Labelled ECR by Affinity Chromatography on a RGD Sepharose ™ Column Followed by a Fibrinoaen Sepharose™ Column 1) Seauential Column Chromatography That the EDTA-eluted fibrinogen-binding ECR was a receptor distinct from vitronectin receptor was confirmed using a alternative approach of purifying ECR from labelled cell lysates by affinity chromatography over two different columns. The cell lysate prepared in Example 2A was first applied onto an RGD Sepharose™ column previously equilibrated with TBS extraction buffer to immobilize RGD-specific receptors to the Sepharose™-bound RGD. Coupling of RGD to CNBr-Sepharose™ was performed as described in Example 2A for preparation of a fibrinogen Sepharose™ column. After the overnight maintenance period for maximizing the interaction of the $^{125}$I-labelled cell lysate containing RGD-dependent receptors with the Sepharose™-bound RGD, the flow-through was collected and applied on a fibrinogen Sepharose™ column as described in Example 2B. The RGD column was then washed as previously described. EDTA elution buffer was subsequently applied to the washed RGD column and fractions containing $^{125}$I-labelled EDTA-eluted receptors were collected as described for the elution protocol in Example 2B. The characterization of the EDTA-eluted receptors from the RGD Sepharose™ column is described in Example 2C2) below.

The flow-through from the RGD column was maintained overnight with the fibrinogen column to allow for maximum interaction of the RGD-extracted cell lysate containing RGD-independent fibrinogen receptors with the Sepharose™-bound fibrinogen. After the maintenance period, the $^{125}$I-labelled receptors bound to fibrinogen were eluted following the same procedure as described for the elution from the fibrinogen column in Example 2B. Ten fractions were collected from each of the sequential RGE, RGE and EDTA elutions. The characterization of the RGD- and EDTA-eluted material from the fibrinogen Sepharose™ column is described in Example 2C2) below.

2) Characterization of the RGD- Versus Fibrinogen-Dependent Receptors

Figure 2:
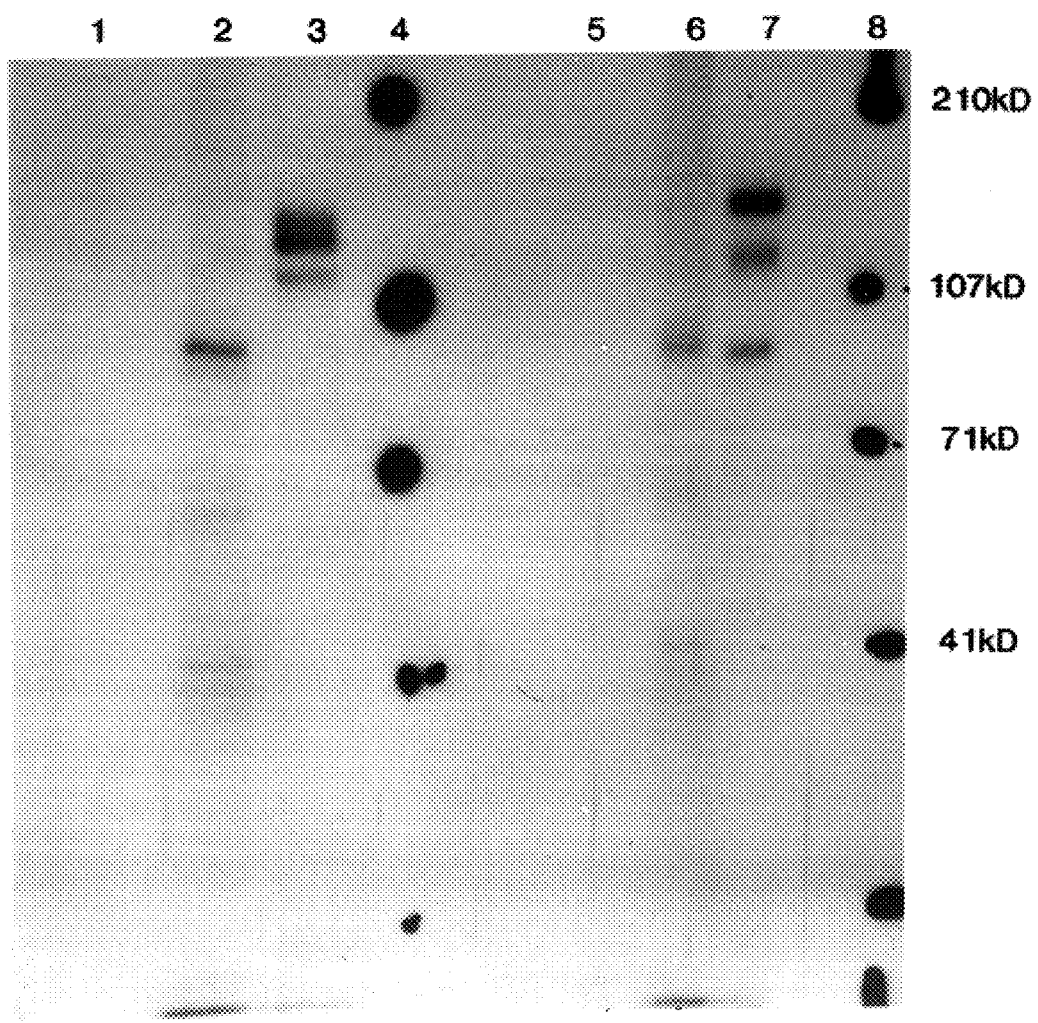
FIG. 2 illustrates the results of autoradiographic exposure of the electrophoresed $^{125}$I-labelled receptors isolated from sequential affinity chromatography of $^{125}$I-labelled HUVEC cell lysate supernatants over an RGD Sepharose™ followed by a fibrinogen Sepharose™ column. The lanes are labelled 1–8. Lanes 1 through 4 show migration of proteins under reducing conditions while lanes 5 through 8 show the migration of identical aliquots run under nonreducing conditions. $^{125}$I-labelled molecular weight standards of 210, 107, 71 and 41 kD, respectively, myosin, beta-galactosidase, bovine serum albumin and ovalbumin are run in lanes 4 and 8.

Aliquots of the collected fractions from the EDTA elution of the RGD Sepharose™ column were electrophoresed adjacent to aliquots from both of the RGD and EDTA elutions from the fibrinogen Sepharose™ column under both nonreducing and reducing conditions to provide for an optimal comparison and characterization of the eluted receptors. Aliquots of the collected fractions were electrophoresed as described in Example 2B2). The results of autoradiographic exposure of the electrophoresed $^{125}$I-labelled receptors are shown in FIG. 2 in 8 lanes. Lanes 1 through 4 show migration of proteins under reducing conditions while lanes 5 through 8 show the migration of identical aliquots run under nonreducing conditions. The molecular weight determinations of the electrophoresed eluted receptors are made by comparison to $^{125}$I-labelled molecular weight standards of 210, 107, 71 and 41 kD, respectively, myosin, beta-galactosidase, bovine serum albumin and ovalbumin. These markers are shown in lanes 4 and 8.

In lanes 3 and 7, the vitronectin receptor eluted with EDTA from the RGD-Sepharose™ column exhibits the characteristic profile of alpha v/beta 3 under reducing and nonreducing conditions. Unreduced alpha v has a molecular weight of 150 kD (lane 7, upper band) which is cleaved into two polypeptides of 125 and 25 kD under reducing conditions (lane 3, middle band—the 25 kD fragment has run off the gel). Unreduced beta 3 has a molecular weight of 90 kD (lane 7, lower band) which is increased to 110 kD under reducing conditions (lane 3, lower band).

In addition to the vitronectin integrin receptor having alpha v and beta 3 subunits, another integrin beta subunit, beta 1, was eluted from the RGD Sepharose™ column with EDTA. Alpha v has been shown to separately associate with both beta 3 and beta 1 as described by Vogel et al., *J. Biol. Chem.*, 265:5934–5937 (1990). Beta 1 migrates as a 120 kD protein under nonreducing conditions (lane 7, middle band) which increases to 140 kD under reducing conditions (lane 3, upper band). Thus, the RGD-dependent vitronectin receptor consisting of alpha v/beta 3 subunits was eluted from both a fibrinogen Sepharose™ column with RGD and from a RGD column with EDTA.

In contrast, a different profile of the eluted proteins was obtained from fibrinogen affinity chromatography of cell lysates precleared on the RGD Sepharose™ column. As described above under Example 2C1), the flow-through collected from the RGD Sepharose™ column lacking alpha v/beta 1 and beta 3 was then chromatographed on a fibrinogen Sepharose™. Since all the RGD-dependent receptors were removed by the first affinity column chromatography run, no $^{125}$I-labelled elution products were obtained when the fibrinogen column was subjected to RGD elution (lanes 1 and 5, respectively, reduced and nonreduced conditions). However, with EDTA elution following the RGD elution, a single band of approximately 90–95 kD under nonreducing conditions (lane 6) was recovered. Under reducing conditions, the molecular weight of the EDTA-eluted fibrinogen receptor derived from human umbilical vein endothelial cells (HUVEC) referred to as ECR only slightly increased (lane 2). The determined molecular weights of the isolated ECR purified by either of the two approaches described in Examples 2 (sequential elutions of a single fibrinogen Sepharose™ affinity chromatography) or 2C (sequential affinity chromatography on separate affinity columns) were the same. Thus, the identical ECR was purified using two alternative approaches as shown in both FIGS. 1 and 2. In addition, the ECR was also purified by affinity chromatography on a fibrinogen Sepharose™ column with EDTA without a prior elution step with RGD to remove other fibrinogen-binding receptors.

D. Identification of the Purified Fibrinogen-Specific ECR as ICAM-1 by Immunoprecipitation 1) Immunoprecipitation of a 90–95 kD ECR with Anti-ICAM-1 Monoclonal Antibodies Aliquots of fractions containing $^{125}$I-labelled 90–95 kD ECR purified by either approach as described in Example 2B or 2C were used in immunoprecipitations to further identify the fibrinogen-binding ECR. Fifty to 100 µl of peak fractions containing the ECR as determined by affinity chromatography as described above were separately admixed with 20 µg of a mouse monoclonal anti-human Intercellular Adhesion Molecule-1 (ICAM-1) antibody commercially available from Becton Dickinson Immunocytochemistry Systems, Mountain View, Calif. Separate aliquots were admixed with control antibodies. For the IgG control, a mouse monoclonal designated 1C10 commercially available from Telios, San Diego, Calif., was used as a control which recognized a 130 kD endothelial cell surface protein. For the IgM control, an irrelevant IgM mouse monoclonal antibody was used. The admixtures were maintained on ice for one hour to form immune complexes. To immunoprecipitate or collect the formed immune complexes, 100 µl of goat anti-mouse IgG coupled to agarose (Sigma Chemical Co.) at a ratio of 1:1.

Typically, 50 µl of the eluted ECR in a peak fraction was admixed with 50 µl of the goat anti-mouse IgG-coupled agarose and maintained on ice for 30 minutes. The immune complexes bound to goat anti-mouse agarose were subsequently pelleted by centrifugation at 10,000×g for one minute at 4° C. The resultant supernatants were removed by aspiration and the pellets were resuspended in TBS extraction buffer. The pellets were washed 3 times and finally resuspended in Laemmli sample buffer for SDS-PAGE analysis against the molecular weight standards described above. Following electrophoresis, the gel was dried and autoradiographed. A single 90–95 kD band was evident on the developed films indicating that the 90–95 kD fibrinogen affinity purified ECR was in fact ICAM-1 as determined by immunoprecipitation with a mouse monoclonal antibody raised against human ICAM-1.

2) Immunoprecipitation of a 90–95 kD ECR With Anti-HUVEC Monoclonal Antibodies

Immunoprecipitations as described above were also performed with mouse monoclonal antibodies raised against intact unstimulated HUVEC. The preparation and characterization of four such monoclonal antibodies is described in Example 4. Fifty µl of the IgM monoclonal antibody designated 2E12 was admixed with 50 µl of the same fraction used in the immunoprecipitations with the commercially available anti-ICAM-1 antibody. After electrophoresis and exposure of the autoradiographic film, a 90–95 kD band was evident. Thus, the monoclonal antibodies directed against HUVEC cell surface proteins immunoprecipitated the same 90–95 kD protein as that immunoprecipitated with a commercially available mouse monoclonal antibody to human ICAM-1. The ECR that binds to fibrinogen via a RGD-independent binding site is now identified as ICAM-1 as determined by affinity chromatography analysis (Examples 2B and 2C). The binding of the ECR, hereinafter referred to as ICAM-1, to an RGD-independent binding site in fibrinogen is a novel finding.

3. Confirmation of an RGD-Independent Fibrinogen Receptor on Endothelial Cells (HUVEC)

Adhesion of leukocytes to vascular endothelium is one of the earliest events in a variety of immune-inflammatory reactions. At the molecular level, leukocyte adhesion to endothelial cells is a redundant mechanism, supported by the regulated recognition of a disparate set of membrane receptors expressed on both leukocytes and endothelial cells, the latter of which may either be in a resting or a cytokine-stimulated state. A novel set of molecular interactions participating in leukocyte adhesion are now identified. Fibrinogen has been shown to interact leukocytes (monocytes, peripheral mononuclear cells and various cell lines) via the integrin CD11b/CD18, also referred to as Mac-1, as described by Altieri et al., *J. Biol. Chem.*, 265:12119–12122 (1990), hereby incorporated by reference. Studies of the interaction of fibrinogen with endothelial cells in vitro has now resulted in the discovery of an endothelial cell surface membrane receptor that binds an RGD-independent site on fibrinogen. Presented herein are data showing that the interaction between circulating leukocytes and endothelial cells is mediated by a bridging effect of different parts of the fibrinogen molecule to distinct cell surface membrane receptors expressed on each cell type.

A. Demonstration of Fibrinogen Binding to HUVEC

1) Preparation of Iodinated Fibrinogen

Fibrinogen was iodinated using the Iodogen™ method. Briefly, Iodogen™ was dissolved in dichloromethane for a final concentration of 1 $\mu$g/ml and 170 $\mu$l of dissolved Iodogen™ that was dried in the bottom of a glass tube. Fibrinogen, prepared in Example 1A, was resuspended in 0.055 M sodium citrate buffer, pH 7.4, for a final concentration of 5 $\mu$g/ml. Two hundred $\mu$l of dissolved fibrinogen solution was placed into the Iodogen™-coated tube with 700 $\mu$Ci of carrier-free sodium iodide. The admixture was maintained on ice for 20 minutes with occasional agitation. To stop the iodination reaction, the admixture was removed from the tube and gel filtered on a Sepharose™ G-25 coarse column (100×2.5). Fractions of iodinated fibrinogen were determined by trichloroacetic acid precipitable counts. The labelled fibrinogen produced was radiolabelled to a specific activity of 0.3 $\mu$Ci/$\mu$g of protein. Labelled fibrinogen was used in the binding and inhibition of binding assays described herein at a concentration of 50 $\mu$g/ml whereas unlabelled fibrinogen was generally used at a concentration of 500 $\mu$g/ml.

2) Analysis of Dose Dependency

To determine if fibrinogen bound to a cell surface HUVEC receptor and if so, at what concentrations, increasing concentrations from 0.01 micromolar ($\mu$M) up to 0.44 $\mu$M ( 0.14 $\mu$M is equivalent to 50 $\mu$g/ml; 0.29 $\mu$M is equivalent to 100 $\mu$g/ml and 0.44 $\mu$M is equivalent to 150 $\mu$g/ml) of iodinated fibrinogen ($^{125}$I-Fg) prepared above were separately admixed to monolayers of HUVEC cells that were previously washed two times with serum-free RPMI 1640. The HUVEC cell cultures were initially plated in individual wells of a 48 well plate coated for tissue culture (Costar Corp., Cambridge, Mass.) as described in Example 2A for culturing of cells in T75 flasks. The divalent cation, presented as calcium chloride ($CaCl_2$), at a concentration of 2.5 mM was also admixed into the cell-fibrinogen admixtures. The inhibitor of fibrin polymerization, PPack (D-phenyl-1-prolyl-1 arginine chloramethyl; Calbiochem Boehring), was admixed to the cell admixtures at a concentration of 100 mM. PPack was present in all assays where it was necessary to prevent the polymerization of fibrinogen into fibrin.

The resultant admixtures were maintained at 22° C. for 45 minutes to allow for fibrinogen to bind to the plated HUVEC. After the maintenance period, the cells were washed two times with serum-free RPMI 1640 to remove unbound fibrinogen. The cells were then solubilized in 10% SDS and the radioactivity associated under the maintenance conditions was quantitated in a gamma counter.

The resultant data is plotted in FIG. 3 as $^{125}$I-labelled fibrinogen bound in counts per minute (cpm) per well (X $10^{-3}$) on the Y-axis against increasing concentrations of $^{125}$I-labelled fibrinogen (X $10^{-7}$ M) on the X-axis. The data shows that $^{125}$I-labelled fibrinogen binds saturably at a concentration of approximately 0.36 $\mu$M to monolayers of unstimulated HUVEC.

3) Analysis of Effect of HUVEC Stimulation by Exposure to TNF or Lipopolysaccharide on Binding of Fibrinogen To determine the effect that known stimulators of HUVEC have on the binding characteristics of fibrinogen to HUVEC, dose-response experiments were performed as described in Example 3A2) on untreated HUVEC and TNF or lipopolysaccharide (LPS, Genzyme))-stimulated HUVEC. TNF and LPS were separately admixed at the respective concentrations of 5 nanograms (ng)/ml and 1.0 $\mu$g/ml to monolayers of HUVEC and maintained at 37° C. for 4 hours prior to the admixture of the labelled fibrinogen ranging in concentration from 0.01 $\mu$M up to 0.36 $\mu$M.

The resultant data is plotted in FIG. 4 as $^{125}$I-labelled fibrinogen bound in molecules per cell (X $10^{-6}$) on the Y-axis against increasing concentrations of $^{125}$I-labelled fibrinogen (X $10^{-7}$ M) on the X-axis. Under stimulation with either TNF or LPS, the number of labelled fibrinogen molecules bound per cell doubled in comparison to those bound to unstimulated cells. Thus, the increase of fibrinogen binding to ICAM-1 receptor on HUVEC is cytokine or immunostimulant mediated.

4) Analysis of Binding of $D_{30}$ to HUVEC

Binding assays described above in Example 3A2) were also performed with the fibrinogen homolog, $D_{30}$, to determine if that region of fibrinogen also immunoreacted with HUVEC. Since $D_{30}$ was known to bind to leukocytes via the Mac-1 receptor as described by Altieri et al., *J. Biol. Chem.*, 265:12119–12122 (1990), these experiments were performed to determine if regions of fibrinogen mediating the binding of leukocytes to HUVEC are contained within the $D_{30}$ fragment. For this analysis, the $D_{30}$ fragment of fibrinogen prepared in Example 1B was labelled with 125I as described for labelling of fibrinogen above. Iodinated $D_{30}$ was admixed to HUVEC monolayers at a concentration of 10 $\mu$g/ml to form a binding complex. After washing the cells to remove the unbound $D_{30}$ as described in Example 3A2) above, the cells were solubilized and the amount of bound radioactivity was determined. The binding of $D_{30}$ to HUVEC was maximal at 120 minutes of the maintenance period with approximately 60,000 cpm. The binding of $D_{30}$ was specifically competed by admixture of 50 fold molar excess of cold fibrinogen thus confirming that $D_{30}$ specifically bound to a fibrinogen binding site on HUVEC. Myoglobin, a nonspecific protein, did not inhibit the binding of $D_{30}$, to HUVEC.

Confirmation of the specificity of $D_{30}$ binding to HUVEC was obtained by inhibiting the binding of $D_{30}$ to ICAM-1 transfected cells prepared in Example 4 in the presence of the 14E11 IgG monoclonal antibody also prepared in Example 4. The inhibition of binding assays were performed as described in Example 5. The anti-ICAM-1 BD monoclonal antibody described in Example 4 was also used in the assay. Both 14E11 and the anti-ICAM-1BD monoclonal antibodies, at a concentration of 20 $\mu$g/ml in the presence of $MnCl_2$, specifically inhibited the binding of $D_{30}$ to HUVEC. Approximately 3000 and 7500 cpm were recovered from the binding of $D_{30}$ in the presence of $CaCl_2$ and $MnCl_2$, respectively, in the absence of any inhibitors. With 14E11 and $MnCl_2$, $D_{30}$ binding to the transfectants was completely inhibited. The portion of fibrinogen containing $D_{30}$, therefore, binds to the fibrinogen receptor on HUVEC and to surface-expressed ICAM-1 on transfectants.

Furthermore, $D_{30}$-derived peptides defining the Mac-1 receptor binding site on $D_{30}$ did not block the binding of either fibrinogen or $D_{30}$ to the HUVEC, as described herein.

Therefore, the bridging site of fibrinogen that binds to the endothelial fibrinogen receptor is within the $D_{30}$ fragment but is not the same region of $D_{30}$ that mediates the binding of $D_{30}$ or fibrinogen to Mac-1 on leukocytes.

B. Demonstration of Fibrinogen Bridging the Binding of Mac-1-Bearing Cells to an RGD-Independent Fibrinogen Receptor on HUVEC 1) Analysis of Dose Dependency Over Time In vivo, circulating leukocytes have been shown to bind to the apical surface of endothelial cells. In addition, experiments have been performed in vitro where the monocytic cultured cell line, THP-1 having the ATCC accession number TIB 202, (ATCC, Bethesda, Md.), was shown to bind directly to unperturbed HUVEC in the presence of divalent cations with or without stimulation with 1 $\mu$M of the chemotactic peptide, N-formyl-methionyl-leucyl-phenylalanine (N-FMLP) (Sigma Chemical Co.) as described by Altieri, J. Immunol., 147:1891–1898 (1991), hereby incorporated by reference. To determine whether this event was the result of a fibrinogen mediated-bridging phenomenon, in vitro cell attachment binding assays were performed.

For these assays, HUVEC were plated in the medium described in Example 2A at a density of approximately 1–5×10$^4$ cells/well into flat-bottom microtiter wells of a 96 well tissue-culture treated plate. The cells were then washed in serum-free RPMI 1640 and further maintained with $^{51}$-Chromium-labelled ($^{51}$Cr) THP-1 cell suspensions previously exposed to different concentrations of unlabelled fibrinogen or left untreated. To label THP-1 cells, serum-free suspensions of the cells at a concentration of 1×10$^7$ cells/ml were labelled with 0.5 mCi $^{51}$Cr (Na$_2$CrO$_4$ having a specific activity of 487.4 mCi/mg, NEN Du Pont de Nemours) for 2 hours at 37° C. with incorporation of an average of 12 to 20 cpm/THP-1 cell. The labelled cells were then washed twice at room temperature with serum-free RPMI 1640 and resuspended in the same medium at a concentration of 5×10$^5$ cells/ml. The labelled cells were used in the assays within 2 hours from the labelling procedure. For the assays, the cells were pre-stimulated with 1 $\mu$M N-FMLP in the presence of 1 mM CaCl$_2$ and 100 mM PPack. The resultant N-FMLP-stimulated THP-1 cell suspensions were then separately admixed with the following: 1) Medium without any admixed fibrinogen as a control; 2) Fibrinogen at 1.2 mg/ml and at 2.5 mg/ml concentrations; and 3) Normal human plasma (NHP) diluted 1:2 and 1:50. Purified fibrinogen was prepared as described in Example 1. Fibrinogen was present in undiluted normal human plasma at the concentration of approximately 1–3 mg/ml. The resultant admixtures were maintained for 20 minutes at 22° C. to allow for the binding of fibrinogen, either purified or present in NHP, to the Mac-1 receptor on the surface of the THP-1 cells.

The resultant fibrinogen-bound THP-1 cells were then admixed to the washed immobilized HUVEC described above to allow for the binding of a non-Mac-1 receptor binding site on fibrinogen to the RGD-independent fibrinogen receptor on the surface of HUVEC, thereby resulting in the binding of THP-1 cells to HUVEC via a fibrinogen bridge. The admixtures were maintained at 37° C. to allow for adhesion. At selected time intervals between 1 to 60 minutes, the HUVEC monolayers were gently washed five times with serum-free RPMI 1640 to remove nonadherent or loosely adherent THP-1 cells to which fibrinogen was initially immobilized. The adherent cells were then solubilized in 10% SDS and the cell lysate was quantitated in a beta scintillation counter. Spontaneous $^{51}$Cr release from THP-1 cells was always less than 2% during the adhesion assay. The number of specifically attached THP-1 cells was determined by dividing the cpm harvested by the cpm/cell.

The results of these experiments are shown in FIG. 5A and FIG. 5B where the data is expressed as numbers of $^{51}$Cr-labelled THP-1 cells (X 10$^{-3}$) on the Y-axis plotted against the assay time on the X-axis. THP-1 cells did not significantly bind to immobilized HUVEC in the absence of fibrinogen throughout the time course. In contrast, THP-1 cells maintained in the presence of 1.2 mg/ml fibrinogen exhibited significant increases of binding to HUVEC over the time course with the maximum cell attachment occurring at 10,000 cells (FIG. 5A). In the presence of 2.5 mg/ml of fibrinogen, TPC-1 cell attachment had not saturated at the end of 60 minutes where approximately 18,000 THP-1 cells were attached to fibrinogen (FIG. 5A). Similar binding curves were obtained in the presence of NHP shown in FIG. 5B. Maximum THP-1 cell attachment of approximately 23,000 cells was obtained after 40 minutes in the presence of NHP diluted 1:2 which contains approximately 0.5–1.5 mg/ml fibrinogen. NHP diluted 1:50 exhibited a profile comparable to that seen with 1.2 mg/ml of purified fibrinogen. Thus, the time-dependent binding of THP-1 cells to HUVEC was fibrinogen-dependent confirming that fibrinogen, either purified or present in NHP, serves as a protein bridge between the two cell types.

2) Analysis of Temperature Dependency

To determine the effects that temperature has on the ability of fibrinogen to mediate the binding of $^{51}$Cr-labelled THP-1 cells to monolayers of HUVEC, cell adhesion assays as described in Example 3B1) were performed at 22° C. and at 37° C. over the course of one hour. The assays were performed in an identical manner as described above with the exception that 500 $\mu$g/ml of fibrinogen was used instead of 1.2 or 2.5 $\mu$g/ml. The maximum binding of THP-1 cells to HUVEC at 22° C. was 7500 cells after 40 minutes. At 60 minutes, the binding decreased to 5000 cells. The data is significant in comparison to the approximately 2000 THP-1 cells attached in the absence of fibrinogen. However, at 37° C., approximately 20,000 THP-1 cells attached to HUVEC after 40 minutes against a background binding of approximately 5000 cells in the absence of fibrinogen. The binding of $^{51}$Cr-labelled THP-1 cells to HUVEC, thus, is maximized at the physiologic temperature of 37° C. with physiologic concentrations of fibrinogen.

3) Analysis of Cell Type Specificity

Cell adhesion binding assays described above were performed on bovine aortic endothelial cells (BAE) to determine if fibrinogen could mediate the binding of $^{51}$Cr-labelled THP-1 cells to endothelial cells from a different source. Cell cultures were prepared from bovine aorta following procedures known to one skilled in the art. THP-1 cells were either left untreated or treated with 500 $\mu$g/ml fibrinogen over a 60 minute time course. At selected time points, the cells were harvested as described in Example 3B1) and the number of attached THP-1 cells were determined as previously described. In the absence of fibrinogen, THP-1 cells did not significantly bind to BAE cells (less than 5000 cells attached) after an initial rise of attachment peaking at 20 minutes. However, in the presence of fibrinogen, approximately 20,000 cells bound to BAE cells after a 40 minute maintenance period. This maximum binding dropped off at 60 minutes to approximately 15,000 attached cells. Binding of THP-1 cells to HUVEC was done in parallel as a control for the experiment; the non-saturable binding of THP-1 cells in the presence of fibrinogen was maximal at 60 minutes with approximately 25,000 cells attached. Thus, fibrinogen mediates the binding of THP-1 cells not only to human endothelial cells but also to bovine-derived endothelial cells.

4. Preparation of Anti-Endothelial Cell Monoclonal Antibodies to an RGD-Independent Fibrinogen Receptor on HUVEC A. Preparation of Immunogen HUVEC, cultured as described in Example 2A but without TNF or LPS stimulation, were prepared for use as immunogens in order to raise monoclonal antibodies against HUVEC surface proteins for eventual screening by assaying the inhibition of $^{125}$I-labelled fibrinogen binding to HUVEC cultures. For the immunizations, 10×106 cells harvested from the culture plates by treatment with 4.0 mM EDTA and resuspended in saline were injected into mice as described below.

B. Preparation of Monoclonal Antibodies to an RGD-Independent Fibrinogen Receptor on HUVEC The HUVEC, prepared as immunogens according to Example 4A, were injected intraperitoneally (i.p.) into separate BALB/c ByJ mice (The Scripps Research Institute Vivarium, La Jolla, Calif.). The mice received booster injections at 1, 3 and 5 weeks. The last boost was 4 days prior to fusion.

The animals so treated were sacrificed and the spleen of each mouse was harvested. A spleen cell suspension was then prepared. Spleen cells were then extracted from the spleen cell suspension by centrifugation for about 10 minutes at 1000 rpm, at room temperature. Following removal of the resultant supernatant, the cell pellet was resuspended in 5 ml cold ammonium chloride ($NH_4Cl$) lysing buffer, and was maintained for about 10 minutes.

Ten ml of Dulbecco's Modified Eagle Medium (DMEM) (Whittaker M.A. Bioproducts) and Hepes buffer were admixed to the lysed cell suspension to form an admixture, and that admixture was centrifuged for about 10 minutes at 1000 rpm at room temperature.

After the resultant supernatant was decanted, the pellet was resuspended in 15 ml of DMEM and Hepes and was centrifuged for about 10 minutes at 1000 rpm at room temperature. The above procedure was repeated.

The pellet was then resuspended in 5 ml DMEM and Hepes. An aliquot of the spleen cell suspension was then removed for counting. Fusions were accomplished in the following manner using the non-secreting mouse myeloma cell line P3X63Ag8.653.1, a subclone of line P3X63Ag8.653 (ATCC Accession Number CRL 1580). With a myeloma to spleen cell ratio of about 1 to 10 or about 1 to 5, a sufficient quantity of myeloma cells were centrifuged into a pellet, washed twice in 15 ml DMEM and Hepes, and then centrifuged for 10 minutes at 1000 rpm at room temperature.

Spleen cells and myeloma cells were combined in round bottom 15 ml tubes. The cell mixture was centrifuged for 10 minutes at 1000 rpm. at room temperature and the supernatant was removed by aspiration. Thereafter, 200 µl of 50 percent (weight per volume) aqueous polyethylene glycol 4000 molecular weight (PEG) at about 37° C. were admixed with the pellet using a 1 ml pipette with vigorous stirring to disrupt the pellet. The cells were then gently mixed for between 15 and 30 seconds. The resultant cell mixture was centrifuged 4 minutes at 700 rpm.

At about 8 minutes from the time of adding the PEG, 5 ml of DMEM plus Hepes buffer were admixed slowly to the pellet, without disturbing the cells. After 1 minute, the resulting admixture was broken up with a 1 ml pipette and was maintained for an additional 4 minutes. This admixture was centrifuged for 7 minutes at 1000 rpm. The resultant supernatant was decanted, 5 ml of HT (hypoxanthine/thymidine) medium were slowly admixed to the pellet and the admixture was maintained undisturbed for 5 minutes. The pellet was then broken into large chunks and the final cell suspension was placed into T75 flasks (2.5 ml per flask) into which 7.5 ml HT medium had been previously placed. The resulting cell suspension was maintained at 37° C. to grow the fused cells. After 24 hours, 10 ml of HT medium were admixed to the flasks followed 6 hours later by admixture of 0.3 ml of 0.04 mM aminopterin. Forty-eight hours after the fusion, 10 ml of HAT (hypoxanthine/aminopterin/thymidine) medium were admixed to the flasks.

Three days after fusion, viable cells were plated out in 96-well tissue culture plates at about $2 \times 10^4$ viable cells per well (768 total wells) in HAT buffer medium as described in Kennett et al., *Curr. Top. Microbiol. Immunol.*, 81:77 (1978). The cells were fed seven days after fusion with HAT medium and at approximately 4–5 day intervals thereafter as needed with HT medium. Growth was followed microscopically and culture supernatants were collected about two weeks later.

C. Immunoscreenina of Monoclonal Antibodies by Cell Adhesion Assays

The culture supernatants from HAT resistant cultures prepared above were subsequently assayed for the presence of HUVEC RGD-independent fibrinogen receptor antibodies by the binding assays and cell adhesion assays respectively described in Example 3A and 3B, and further described in Example 5. Culture supernatants were tested for their ability to inhibit the binding of $^{125}$I-labelled fibrinogen to monolayers of HUVEC. For this assay, the monolayers were maintained in the presence of hybridoma culture supernatant and 2.5 mM $CaCl_2$ for 30 minutes at 37° C. After the maintenance period, the supernatant-treated HUVEC were washed once with RPMI 1640. Labelled fibrinogen was then admixed to the treated HUVEC at a concentration of 50 µg/ml in the presence of 2.5 mM $CaCl_2$ and 100 mM PPack. The resultant admixtures were maintained for 30–60 minutes at 22° C. The fibrinogen-treated HUVEC were then washed, solubilized and counted as described in Example 3A.

Supernatants were also screened for their ability to block the binding of $^{51}$Cr-labelled THP-1 cells previously exposed to fibrinogen to HUVEC cells. The assay was performed essentially as described for the cell adhesion assay in Example 3B with the exception that the HUVEC were separately maintained with hybridoma supernatants for 30 minutes at 37° C. as described above. Following the antibody exposure, the cells were washed once with culture medium prior to the admixture of the fibrinogen-bound and labelled THP-1 cells at the desired concentrations as described in Example 3B.

Hybridoma culture supernatants that produced an antibody of this invention which effectively blocked the fibrinogen-mediated binding of THP-1 cells to monolayers of HUVEC were then selected for subsequent purification and characterization. Hybridoma cultures producing antibodies against RGD-independent fibrinogen receptors (also referred to as a fibrinogen binding site) on HUVEC were identified. Four separate antibodies, designated 14E11, 16G8, 2E12 and 2B12, were obtained. 14E11 was determined to be an IgG while the remaining monoclonals were determined to be IgMs. The monoclonal antibodies, specific for an endothelial cell RGD-independent fibrinogen receptor (also referred to as anti-ECR equivalent to anti-ICAM-1 based on the affinity chromatography analysis in Example 2), were shown to immunoreact with HUVEC in addition to the purified ECR eluted from a fibrinogen Sepharose™ column with EDTA as described in Example 2D, and to not immunoreact with VNR.

D. Purification of the Selected Monoclonal Antibodies

The four hybridomas secreting anti-ECR antibodies as described in Example 4C were injected into 10-week old BALB/c mice as described below to produce ascites fluid.

To that end, separate sets of 10-week old BALB/c mice were primed with 0.3 ml of mineral oil and then injected intraperitoneally with $5 \times 10^6$ hybridoma cells for each monoclonal. The average time for development of ascites was 9 days. Following clarification by centrifugation at 15,000×g for 15 minutes at room temperature, ascites fluids produced by hybridomas were pooled and stored frozen at −20° C. to form monoclonal antibody compositions.

The ascites-produced monoclonal antibodies were further purified by fast protein liquid chromatography (FPLC) using a Pharmacia Mono Q HR5/5 anion exchange column (Pharmacia) using a 0–0.5 M NaCl gradient in 10 mM Tris-HCl at pH 8.0 following directions supplied with the column. The FPLC-treated monoclonal antibodies were then concentrated using an Amicon stirred ultrafiltration cell (Danvers, Mass.; PM 30 membrane) to a concentration of 1 mg/ml, dialyzed into PBS and stored at −70° C. to form purified MAb.

The monoclonal antibody, 14E11, was further affinity purified using a affinity purification kit, Affi-Prep, according to the manufacturer's instructions (Bio-Rad, Richmond, Calif.). The IgM monoclonal antibodies were further purified by hydroxylapatite gel filtration over a Bio-Gel HPHT hydroxylapatite column according to manufacturer's instructions (Bio-Rad). These purified antibodies were used in subsequent binding assays, Western immunoblots and immunoprecipitations are described in the Examples.

E. Confirmation of the Immunospecificity of the Monoclonal Antibodies to an RGD-Independent Fibrinogen ReceDtor on HUVEC The immunospecificity of the monoclonal antibodies, 14E11, 16G8, 2E12 and 2B12, was confirmed by a number of approaches. Firstly, as described in Example 2D, immunoprecipitation of the fibrinogen affinity chromatography-purified ECR was performed using 2E12 in comparison to immunoprecipitation with a commercially available anti-ICAM-1 antibody (Becton Dickinson, referred to as BD). The 90–95 kD purified ECR was immunoprecipitated with both of the antibodies indicating that the 2E12 antibody had the same immunospecificity as the anti-ICAM-1 antibody and that the purified ECR was ICAM-1. The exact epitopes of the ECR (ICAM-1) recognized by the antibodies, 2E12 and Becton Dickinson anti-ICAM-1, have not been determined. Based on the blotting profile obtained by Western immunoblot analysis described below and by the inhibition of binding data presented in Example 5, the epitopes are likely to be unique.

Fluorescent Activated Cellscan (FACscan) analysis was performed on an fibroblast-like cell line which was genetically engineered to express the recombinant form of ICAM-1 on the surface of the cells as described by Seed et al., Nature, 331:624–627 (1988), hereby incorporated by reference. Briefly, a cDNA library, constructed using RNA prepared from HL-60 cells induced with 12-O-tetradecanoyl phorbol 13-acetate (TPA), was transfected into COS cells. The cells expressing surface antigens were screened by panning with anti-ICAM monoclonal antibodies, designated 8F5 and 84H10, resulting in the selection of a cDNA clone in a transfected cell expressing ICAM-1. These transfectants were used in FACscan analysis to confirm the immunospecificity of the anti-ECR antibodies of this invention.

For the analysis, $1 \times 10^6$ ICAM-1 transfectant cells in suspension were separately admixed with 1 µg/ml affinity-purified 14E11, an admixture of hydroxylapapatite purified of all three IgM monoclonal antibodies (16G8, 2E12 and 2B12), with the anti-ICAM-1 BD monoclonal antibody and a control monoclonal antibody designated PMI-I having the ATCC Accession Number HB 9476. The latter recognizes the C-terminal hGPIIb fragment of the receptor GPIIb/IIIa found on platelets. The separate admixtures were maintained for 30 minutes at 4° C. to form immunoreaction products. After 3 washes in serum-free RPMI 1640, the immunoreacted transfected cells were admixed with fluorescein-conjugated goat anti-mouse immunoglobulins and maintained for 30 minutes at 4° C. to form secondary immunoreaction products. After washing 3 times, the cells were subjected to flow cytometry on a Becton Dickinson IV/40 fluorescence activated cell sorter.

The results of the FACscan revealed that 16G8, 2E12 and 2B12 monoclonal antibodies specifically immunoreacted with the ICAM-1-expressing transfectants comparably to that seen with the anti-ICAM-1 BD antibody. 14E11, however; did not specifically immunoreact with the ICAM-1-expressing transfectants as its profile overlapped that seen with the control PMI-I antibody. Since the ICAM-1 expressed on the transfectants is known to be unglycosylated, the lack of immunoreactivity of 14E11 with the cells is mostly likely due to this reason. In the initial screen of the hybridomas, the 14E11 monoclonal antibody did block the binding of $^{125}$I-labelled fibrinogen to HUVEC as well as block the binding of THP-1 cells via a fibrinogen bridge to HUVEC cells.

That the 14E11 monoclonal antibody specifically recognized the ECR identified as ICAM-1 was confirmed by Western immunoblot. Both HUVEC and Daudi cells were used for the blotting. Daudi is a Burkitt's lymphoma human cell line that expresses high levels of ICAM-1 and is available from ATCC having the ATCC Accession Number CCL 213. Cell lysates were prepared from cultures of each cell type as described for preparation of a cell lysate in Example 2A with the exception that the cells were lysed with 0.5% Triton-X 100 and 0.5% NP-40. After centrifugation as described in Example 2A, aliquots of each resultant supernatant were electrophoresed into multiple lanes by 10% SDS-PAGE.

Following the electrophoresis, the proteins in the gel were transferred electrophoretically to nitrocellulose for subsequent immunoreactions. After the nitrocellulose blot was maintained for 2 hours at room temperature immersed in a solution of non-fat dry milk (Blotto) to block nonspecific binding sites, it was then cut into strips to isolate each individual lane of electrophoresed proteins, 5 for Daudi and 8 for HUVEC. The nitrocellulose strips were then separately immunoreacted with two control antibodies, 2E1 and PMI-I, purified 14E11 IgG, 14E11 culture supernatant and anti-ICAM-1BD monoclonal antibody for 1 hour at room temperature to form primary immunoreaction products. The concentration of the primary antibodies added was approximately 10 µg/ml. The immunoreacted blots were then washed 4 times with PBS for 5 minutes each. The washed blots were then immersed for 1 hour at room temperature in a solution of secondary $^{125}$I-labelled goat anti-mouse antibodies (Zymed Laboratories Inc., San Francisco, Calif.) to form secondary immunoreaction products. The immunoreacted blots were then washed 4 times with PBS and exposed to X-ray film for the detection of immunoreacted electrophoresed proteins from the cell lysate supernatants. Additional controls included reacting the strips with a only the labelled secondary antibody.

The results of the Western blot are shown in FIG. 6. The relative molecular weights of the electrophoresed proteins in the cell lysate supernatants were determined by comparison with a set of radiolabelled molecular weight markers of 97, 66, 45, 30 and 21 kD shown in lane left of the first set of 5 Daudi lanes and left of the second set of 8 HUVEC lanes. Lanes designated 1–5 at the bottom of the blot for both Daudi and HUVEC were respectively immunoreacted with 2E1, PMI-I, affinity purified 14E11, 14E11 culture supernatants and the anti-ICAM-1 BD monoclonal antibodies. A 90–95 kD band was detected in both Daudi and HUVEC cell lysate supernatants with the affinity purified 14E11 monoclonal antibody shown in number 3 labelled lanes. In addition, the affinity purified 14E11 immunoreacted with a protein of approximately 50–55kD in lane 3 of the HUVEC-electrophoresed proteins. While the anti-ICAM-1 BD antibody slightly immunoreacted with the Daudi proteins, it strongly immunoreacted with only the 90–95 kD band in the HUVEC electrophoresed proteins. The apparent difference in blotting patterns between the 14E11 and anti-ICAM-1 BD monoclonal antibodies supports the position that they recognize separate epitopes on the ICAM-1 molecule. The control primary antibodies, 2E1 and PMI-I, immunoreacted with the electrophoresed Daudi and HUVEC proteins as predicted based on prior characterizations of binding specificities. Thus, the 14E11 IgG monoclonal antibody specifically recognized the 90–95 kD cell surface protein isolated from both Daudi and HUVEC comparable to that seen with the anti-ICAM-1 BD antibody by both Western blot described herein and by immunoprecipitation described in Example 2D.

In addition, as shown in Example 5, the affinity purified 14E11 antibody was completely effective at inhibiting the binding of THP-1 cells via the fibrinogen bridge to HUVEC.

5. Inhibition of Fibrinogen-Mediated Binding of Leukocytes to Endothelial Cells

A. Inhibition of Fibrinogen-Mediated Binding of THP-1 Cells to HUVEC Using Fibrinogen Analogs 1) Excess Cold Fibrinogen Binding of $^{125}$I-labelled fibrinogen binding to HUVEC assays were performed in the presence of 50 molar excess of unlabelled fibrinogen in order to confirm the specificity of binding as shown in Example 3A. The binding assay was performed as described in Example 3A with the exception that unlabelled fibrinogen was admixed to HUVEC at a 50 molar excess (approximately $7.5 \times 10^{-3}$ M fibrinogen) concurrently with 50 μg/ml of $^{125}$I-labelled fibrinogen. The protein-cell admixtures were maintained at 22° C. for 30 minutes to allow for binding of fibrinogen to HUVEC. In addition to cold fibrinogen, a 50 fold molar excess of BSA was separately admixed as a control. The amount of fibrinogen bound under the above conditions was quantitated as described in Example 3A. The uninhibited total binding of $^{125}$I-labelled fibrinogen saturated after 30 minutes at approximately 4000 cpm per well. The BSA did not inhibit the binding and thus $^{125}$I-labelled fibrinogen exhibited a similar profile in the presence of BSA. Unlabelled fibrinogen, however, competed the binding of the labelled fibrinogen to half that of the total uninhibited binding. The binding of fibrinogen to the HUVEC surface fibrinogen receptor is therefore specific.

The specificity of binding to an RGD-independent fibrinogen receptor was confirmed in competition assays performed as described above in the presence of monoclonal antibodies against the beta subunit of the RGD-dependent VNR and in the presence of RGD-containing peptides. For the assays in which the ability of anti-VNR monoclonal antibodies, designated mAb 609 and mAb 7E3, to inhibit the binding of $^{125}$I-labelled fibrinogen to HUVEC, the antibodies were separately maintained at a concentration of 25 μg/ml with HUVEC for 20 minutes at 37° C. After the maintenance period, the antibody-treated HUVEC were washed once with serum-free RPMI 1640 to remove any unbound antibody. Labelled fibrinogen was then admixed to the treated HUVEC at a concentration of 50 μg/ml in the presence of 2.5 mM $CaCl_2$ and 100 mM PPack. The resultant admixtures were maintained for 10–30 minutes at 22° C. The fibrinogen-treated HUVEC were then washed, solubilized and counted as described in Example 3A.

The results are shown in the bar graphs in FIG. 7 where the amount of $^{125}$I-labelled fibrinogen bound to HUVEC in cpm/well ($X 10^{-3}$) is plotted on the Y-axis against the length of time labelled fibrinogen was maintained with HUVEC. Each part of the bar graph is separately identified for each time point as follows: total binding (no inhibitors admixed), +Fg (fibrinogen) admixed, +mAb 609; and +mAb 7E3. Cold fibrinogen that was added in 50 molar excess as described above almost completely inhibited the binding of $^{125}$I-labelled fibrinogen to HUVEC. The VNR antibodies, however, had no inhibitory effect as anticipated by the results with the affinity chromatography in Example 2. Thus, fibrinogen binds to an receptor on HUVEC that is not VNR.

To confirm that the fibrinogen binding site on HUVEC was not RGD dependent, inhibition assays performed as described above for inhibiting with antibodies except that they were done in the presence of 1.0 mM of an RGD-containing peptide. A control RGE-containing peptide was also included in the assay. At selected time points over the time course of one hour, the HUVEC were harvested as described in Example 3A.

The resultant data are shown in FIG. 8 where the amount of $^{125}$I-labelled fibrinogen bound to HUVEC in cpm/well ($X 10^{-3}$) is plotted on the Y-axis against the length of time labelled fibrinogen was maintained with HUVEC. Neither the RGD- nor the RGE-containing peptide had any inhibitory effect of the binding of labelled fibrinogen to HUVEC as compared to the total binding of the labelled fibrinogen in the absence of any inhibitor. The RGD- and the RGE-containing peptide data are shown respectively as the lines indicated by the solid and open squares. Cold fibrinogen completely inhibited the binding of labelled fibrinogen as expected.

In summary, an excess of unlabelled fibrinogen completely inhibits the binding of labelled fibrinogen to HUVEC and this binding is mediated through an RGD-independent fibrinogen receptor that is not VNR.

2) Anti-ECR (ICAM-1) Monoclonal Antibodies

The monoclonal antibodies generated by immunizing mice with intact unstimulated HUVEC as prepared in Example 4 were tested for their ability to inhibit the binding of $^{125}$I-fibrinogen to HUVEC either unstimulated or stimulated with TNF. The binding assays were performed as described in Example 3A with the exceptions described in Example 4 for the screening of hybridoma culture supernatants. HUVEC were exposed to 5 ng/ml TNF for 4 hours at 37° C. prior to admixture of the antibodies. After the stimulation, the cells were washed once with the HUVEC culture medium prepared in Example 2A. The monoclonal antibodies, affinity purified 14E11, anti-ICAM-1 BD, and PMI-I (all described in Example 4), were separately admixed at a concentration of 20 μg/ml to either stimulated or unstimulated HUVEC cultures and maintained for 30 minutes at 37° C. After the antibody-reacted cells were washed once with culture medium, 50 μg/ml of $^{125}$I-labelled fibrinogen prepared in Example 3A was admixed to each well and maintained for 30 minutes at 22 $\mu$C. The cells were subsequently washed and solubilized as described in Example 3A.

The resultant data is shown in FIGS. 9A and FIGS. 9B which respectively shown the effects of antibody exposure on binding of $^{125}$I-labelled fibrinogen to unstimulated and TNF-stimulated HUVEC. The data is expressed in a bar graph as the specific binding of $^{125}$I-labelled fibrinogen in cpm/well (X 10–3) on the Y-axis against the specific treatments on the X-axis. As shown in FIG. 9A, 14E11 partially inhibited the binding of fibrinogen while the BD anti-ICAM-1 antibody was slightly more effective. However, in the TNF-stimulated HUVEC cultures shown in FIG. 9B, 14E11 completely inhibited the binding while the BD antibody was only partially effective. The control antibody, PMI-I, was not inhibitory as compared to the amount of binding in the absence of any antibody. The results, therefore, support the finding that 14E11 specifically recognizes a fibrinogen receptor (or binding site) on the surface of HUVEC the occupation of which completely inhibits the binding of fibrinogen to TNF-stimulated HUVEC. This in vitro system mimics that found in vivo and thus the antibodies of this invention would be useful as therapeutics.

6. Preparation of Anti-Fibrinogen Monoclonal Antibodies That Block the Binding of Fibrinogen to the RGD-Independent Fibrinogen Receptor on Endothelial Cells A. Preparation of Immunogen Fibrinogen and the fragments D and E prepared therefrom as described in Example 1, are prepared for use as immunogens in order to raise monoclonal antibodies against the portion of fibrinogen that mediates the binding of fibrinogen to the RGD-independent fibrinogen binding site on endothelial cells. For the immunizations, 50 $\mu$g of separately prepared fibrinogen immunogens are admixed in complete Freund's adjuvant (CFA).

B. Preparation of Monoclonal Antibodies to the Fibrinogen Site That Mediates the Binding of Fibrinogen on HUVEC The HUVEC, prepared as immunogens according to Example 4A, are injected intraperitoneally (i.p.) into separate BALB/c ByJ mice followed by a second and third immunization using the same fibrinogen immunogens, each about three weeks apart, in incomplete Freund's adjuvant (IFA). The mice receive a boost of 50 $\mu$g of prepared fibrinogen immunogens intravenously (i.v.) in normal saline four days prior to fusion and a second similar perfusion boost one day later.

The animals so treated are sacrificed and the spleen of each mouse is harvested. A spleen cell suspension is then prepared and subjected to the fusion protocol as described in Example 4. Growing clones are then screened for the expression of hybridomas having the selected specificity as described below.

C. Immunoscreening of Monoclonal Antibodies by Binding Assays

The culture supernatants from HAT resistant cultures prepared above are subsequently assayed for the presence of fibrinogen antibodies that function to inhibit the binding of fibrinogen to the RGD-independent fibrinogen receptor on endothelial cells. The supernatants are screened by both the inhibition of $^{125}$I-labelled fibrinogen binding assay and the inhibition of $^{51}$Cr-labelled and fibrinogen-bound THP-1 cell attachment assay as described in Example 4C, which are based on the assays described in Example 3A and 3B. The inhibition of binding assay is further described in Example 5.

Hybridoma culture supernatants that produce an antibody that binds to the site on fibrinogen that mediates the binding of fibrinogen to the RGD-independent fibrinogen receptor on endothelial cells (also referred to as ICAM-1 based on the analysis in Examples 2–5 are then selected for subsequent purification and characterization. Hybridoma cultures producing antibodies against fibrinogen are identified. The monoclonal antibodies, specific for a region on fibrinogen that binds to the RGD-independent fibrinogen receptor on endothelial cells (ICAM-1) shown to immunoreact with fibrinogen in addition to the analogs thereof, and to not immunoreact with the site on fibrinogen that mediates the binding to MAC-1, namely the site defined by the $D_{30}$-derived peptides described in Example 3.

D. Purification of the Selected Monoclonal Antibodies

The selected hybridomas secreting anti-fibrinogen antibodies as described in Example 6C are injected into 10-week old BALB/c mice as described in Example 4D produce ascites fluid.

The ascites-produced monoclonal antibodies are further purified by fast protein liquid chromatography (FPLC) using a Pharmacia Mono Q HR5/5 anion exchange column (Pharmacia) using a 0–0.5 M NaCl gradient in 10 mM Tris-HCl at pH 8.0 following directions supplied with the column. The FPLC-treated monoclonal antibodies are then concentrated using an Amicon stirred ultrafiltration cell (Danvers, Mass.; PM 30 membrane) to a concentration of 1 mg/ml, dialyzed into PBS and stored at −70° C. to form purified monoclonal antibody.

The monoclonal antibodies is further affinity purified using a affinity purification kit, Affi-Prep, according to the manufacturer's instructions (Bio-Rad, Richmond, Calif.). The IgM monoclonal antibodies are further purified by hydroxylapatite gel filtration over a Bio-Gel HPHT hydroxylapatite column according to manufacturer's instructions (Bio-Rad). These purified antibodies are used in subsequent binding assays, Western immunoblots and immunoprecipitations for use in this invention.

7. Preparation of Anti-Endothelial Cell Monoclonal Antibodies Immunoreactive with the RGD-Independent Fibrinogen Receptor on Daudi Cells A. Preparation of Immunogen Daudi is a Burkitt's lymphoma human cell line that expresses high levels of ICAM-1 and is available from ATCC having the ATCC Accession Number CCL 213. Daudi was prepared for use as immunogens in order to raise monoclonal antibodies against Daudi surface proteins for eventual screening by assaying the inhibition of fibrinogen-mediated binding of leukocytes to HUVEC.

Daudi was cultivated in complete RPMI 1640 medium supplemented with 10% fetal calf serum (FCS, Whittaker) and 2 mM L-glutamine (Irvine Scientific, Santa Ana, Calif.).

B. Preparation of Monoclonal Antibodies to a Fibrinogen Receptor on Daudi

For the immunizations, $10 \times 10^6$ Daudi cells harvested from the culture plates by treatment with 4.0 mM EDTA and resuspended in saline were injected into mice and monoclonal antibodies prepared as described in Example 4B.

C. Immunoscreening of Monoclonal Antibodies by Binding Assays

The culture supernatants from HAT resistant cultures prepared above were assayed for HUVEC fibrinogen receptor antibodies by flow cytometry as described by Languino, et al., Cell, 73:1423–1434 (1993). HUVEC were activated with TNF to increase the number of fibrinogen binding sites expressed on the surface of the cells as described in Example 3A3. Briefly, TNF was admixed at 5 nanograms (ng)/ml and added to monolayers of HUVEC and maintained at 37° C. for 4 hours. Aliquots of suspended TNF stimulated HUVEC at 1.5×10⁷/ml were washed in PBS, pH 7.2, plus 5 mM EDTA; blocked with 20% normal human serum to prevent Fc-mediated monoclonal antibody binding for 30 min at 4° C.; and incubated with aliquots of the culture supernatants containing the monoclonal antibody for 30 min at 4° C. in complete RPMI 1640 medium plus 10% FCS. After washes, binding of the primary monoclonal antibodies was revealed by the addition of a 1:20 dilution of fluorescein-conjugated goat anti-mouse F(ab')$_2$ fragments for 30 min at 4° C. Cells were washed and immediately analyzed on a Becton-Dickinson IV/40 fluorescence activated cell sorter. Background fluorescence was assessed in the presence of control anti-plasminogen monoclonal antibody.

Hybridoma culture supernatants that produced an antibody which bound to surface proteins on TNF stimulated HUVEC were identified. Three separate antibodies, designated 1G12, 2D5, and 6E6 were obtained. These antibodies were subsequently assayed for their ability to block fibrinogen-mediated binding of leukocytes (THP-1) to HUVEC as described in Example 3B. Hybridoma culture supernatants that produced an antibody which effectively blocked the fibrinogen-mediated binding of THP-1 cells to monolayers of HUVEC were selected for subsequent purification as described in Example 4D and further characterized. Two separate antibodies, designated 1G12 and 2D5, were obtained. A third antibody, 6E6, which reacted with the TNF stimulated HUVEC but did not block fibrinogen-mediated binding of leukocytes to HUVEC was also purified as described in Example 4D and characterized.

D. Identification of Fibrinoaen Binding Site on HUVEC as ICAM-1

Purified monoclonal antibodies 1G12, 2D5, and 6E6 were further characterized to identify the fibrinogen binding site on HUVEC by reactivity with wild-type CHO cells and transfected CHO cells which expressed recombinant ICAM-1 on their surface.

1) Preparation of Cells

The Chinese Hamster Ovary (CHO) cells were cultivated in DMEM medium (Whittaker) supplemented with 10% fetal calf serum (FCS, Whittaker) and 1 mM L-glutamine (Irvine Scientific, Santa Ana, Calif.), non-essential amino acids, penicillin-streptomycin.

2) Transfection of ICAM-1 Expression Vector Into CHO Cells

A full length cDNA clone encoding for ICAM-1 (Simmons et al., Science, 331:624–627 (1988)) was inserted into the mammalian expression vector pRC/CMV (Invitrogen, San Diego, Calif.), oriented, and transfected (15 μg plasmid DNA) in subconfluent cultures of CHO cells by electroporation. Forty-eight hours after transfection, CHO cells were harvested and diluted to 6×10³ cells/80 mm diameter tissue culture Petri dish (Costar) in DMEM (Whittaker) selection medium containing 10% FCS, 1 mM L-glutamine, non-essential amino acids, penicillin-streptomycin plus 1 mg/ml G418 (Geneticin, GIBCO, Grand Island, N.Y.). After a 2 to 3 week culture in selection media, CHO cells were harvested and phenotypically characterized by flow cytometry using anti-ICAM-1 monoclonal antibody (Becton Dickinson, referred to as BD or LB-2). CHO cells which were reactive with the anti-ICAM-1 were cloned by limiting dilution in 96-well tissue culture plates (Costar) in DMEM selection medium at 0.5–2 cells/well.

3) Immunoreactivity of Monoclonal Antibodies with CHO Cells

The monoclonal antibodies 1G12, 2D5, and 6E6 were assayed for reactivity with wild-type and ICAM-1transfected CHO cells. Briefly, aliquots of suspended CHO cells at 1.5×10⁷/ml were washed in PBS, pH 7.2, plus 5 mM EDTA; blocked with 20% normal human serum to prevent Fc-mediated monoclonal antibody binding for 30 min at 4° C.; and incubated with aliquots of each monoclonal antibody for 30 min at 4° C. in complete RPMI 1640 medium plus 10% FCS. After washes, binding of the primary monoclonal antibodies was revealed by the addition of a 1:20 dilution of fluorescein-conjugated goat anti-mouse F(ab')$_2$ fragments for 30 min at 4° C. Cells were washed and immediately analyzed on a Becton-Dickinson IV/40 fluorescence activated cell sorter. Background fluorescence was assessed in the presence of control anti-plasminogen monoclonal antibody.

Results of the FACScan revealed that the monoclonal antibodies 1G12, 2D5, and 6E6 specifically immunoreacted with the ICAM-1-expressing transfectants but not the wild-type CHO cells indicating that the monoclonal antibodies reacted specifically with the recombinant ICAM-1.

4) Immunoscreening of Monoclonal Antibodies by Binding Assays

The monoclonal antibodies 1G12, 2D5, and 6E6 which recognize ICAM-1 were subsequently assayed for their ability to inhibit fibrinogen-mediated leukocyte binding to HUVEC. The monoclonal antibodies are screened by the inhibition of $^{51}$Cr-labelled and fibrinogen-bound THP-1 in a cell attachment assay as described in Example 4C, which are based on the assays described in Example 3A and 3B. The inhibition of binding assay is further described in Example 5.

The monoclonal antibodies 1G12 and 2D5, specific for a region on ICAM-1 on endothelial cells (ICAM-1), inhibited the fibrinogen-mediated leukocyte binding to HUVEC. The monoclonal antibody 6E6, specific for a region on ICAM-1 on endothelial cells (ICAM-1), did not inhibit the fibrinogen-mediated leukocyte binding to HUVEC.

8. Characterization of the I-CAM Receptor Binding Site on Fibrinogen

A. Polypeptide Synthesis

Polypeptides derived from the γ chain of fibrinogen were synthesized using the classical solid-phase technique described by Merrifield, Adv. Enzymol., 32:221–296 (1969) as adapted for use with a model 430 automated peptide synthesizer (Applied Biosystems, Foster City, Calif.). The amino acid residue sequence of the synthesized polypeptide γ3 is N$^{117}$NQKIVNLKEKVAQLEA$^{133}$ (SEQ.ID NO 2). The residue numbers corresponding to specific regions in the mature γ chain are shown for the γ3 polypeptide. The amino acid residue sequences of the synthesized polypeptides L10is L$^{402}$GGAKQAGDV$^{411}$ (SEQ ID NO 5). The residue numbers corresponding to specific regions in the mature γ chain are shown for the L10 polypeptide. Prepared polypeptide resins were cleaved by hydrogen fluoride, extracted and analyzed for purity by high-performance liquid chromatography (HPLC) using a reverse-phase C18 column manufactured by Waters Associates, Milford, Mass. The amino acid composition was verified as described by Altieri, et al., J. Biol. Chem., 268:1847–1853 (1993).

1) Binding Assay with Iodinated γ3 and Cells

Ninety-six well assay plates (Costar, Cambridge, Mass.) were coated with increasing concentrations (1–100 μg/ml) of the polypeptides γ3 and L10 in PBS, pH 7.2, for 18 h at 4° C. Wells were washed in PBS, pH 7.2 and blocked with 3% gelatin for 60 min at 37° C.

Serum-free suspensions of JY lymphocytes were labeled with 0.5 mCi $^{51}$Cr (Na$_2$CrO$_4$, specific activity 487.4 mCi/mg, E. I., DuPont de Nemours, Wilmington, Del.) for 2 h at 37° C., with a final incorporation of 0.2–4 cpm/cell (Languino, et al., supra). Aliquots of $^{51}$Cr-labeled JY lymphocytes at 1×10$^6$/ml were added to peptide-coated-wells for 45 min at 37° C., washed, solubilized in 20% SDS, and radioactivity associated under the various conditions was determined in a scintillation beta-counter. The number of attached cells was quantitated by dividing the cpm harvested by the cpm/cell. Data are the mean±S.D. of two independent experiments.

The specific binding of radiolabelled ICAM-1$^+$ JY lymphocytes to increasing concentrations of γ3 was measured to characterize the ICAM-1 binding site. The results of the binding assay are shown in FIG. 12. The number of attached cells is plotted on the Y-axis against peptide concentration (μg/ml) plotted on the X-axis. The results demonstrate that JY lymphocytes strongly adhered to immobilized γ3 in a specific and dose-dependent fashion, while control peptide L10 did not support lymphocyte adhesion at any concentration tested under the same experimental conditions.

B. Competition of Binding of γ3 Polyneptide to ICAM-1 Binding Site on JY Lymphocytes 1) Inhibition of γ3 Binding to ICAM-1$^+$ JY Lymphocytes With Anti-ICAM-1 Monoclonal Antibodies The specificity of the γ3 polypeptide for the ICAM-1 receptor on JY lymphocytes was confirmed in assays where the binding of purified γ3 to JY lymphocytes was inhibited by monoclonal antibodies which recognize ICAM-1 and have been shown to block ICAM-1:fibrinogen interaction but not by monoclonal antibodies which recognize ICAM-1 but have not been shown to block ICAM-1:fibrinogen interaction.

Binding inhibition assays were performed using radiolabeled ICAM-1$^+$ JY lymphocytes and the γ3 polypeptide. The competitive inhibitors evaluated in the assay included the following: monoclonal antibodies lG12 and 2D5 which recognize ICAM-1 and have been shown to block ICAM-1:fibrinogen interaction (Languino et al., Cell, 73:1423–1434 (1993)), monoclonal antibody 6E6 which recognizes ICAM-1 and has not been shown to block ICAM-1:fibrinogen interaction, and monoclonal antibody 6A11 which recognizes EPR-1. The peptides used in this assay were the γ3 and irrelevant polypeptide L10 prepared as described in Example 7A.

Ninety-six well assay plates were coated with 20 μg/ml of the polypeptides γ3 and L10 and the $^{51}$Cr-labeled JY lymphocytes were prepared as described above. The $^{51}$Cr-labeled JY lymphocytes were preincubated with saturating concentrations (25 μg/ml) of monoclonal antibodies anti-ICAM-1 1G12, 2D5, or 6E6; or anti-EPR-1 6A11 before incubation in the 3 peptide-coated plates. Binding of radiolabelled JY lymphocytes was measured after a 45 min maintenance period in the presence of the monoclonal antibodies in the γ3 peptide-coated plate. Background binding was assessed by the incubation of $^{51}$Cr-labeled JY lymphocytes which had not been preincubated with a monoclonal antibody in the L10 peptide-coated plate. Data are the mean±S.D. of replicates of two independent experiments.

The results of the inhibition of binding assays are shown in FIG. 12. The number of attached cells is plotted on the Y-axis against the peptide L10 plotted on the X-axis. Also plotted on the X-axis is the peptide γ3 and the monoclonal antibodies used in the inhibition study. The amount of inhibition by the individual competitors is consistent with the postulated recognition of fibrinogen (Languino, et al., supra) by anti-ICAM-1monoclonal antibodies 1G12 and 2D5 which were specifically selected for their ability to block ICAM-1:fibrinogen interaction. 1G12 and 2D5 completely inhibited the adhesion of JY lymphocytes to γ3-coated plates. The control anti-ICAM-1 monoclonal antibody 6E6 which recognizes ICAM-1 and has not been shown to block ICAM-1:fibrinogen interaction, did not inhibit adhesion of JY lymphocytes to γ3-coated plates. The irrelevant polypeptide, L10, did not support significant JY lymphocyte adhesion under the same experimental conditions. Thus, the minimal amino acid residue sequence required to promote the attachment of the γ chain of fibrinogen to ICAM-1 is from amino acid residue 117 to amino acid residue 133 as determined from the complete inhibition of binding of ICAM-1$^+$ JY lymphocyte cells to γ3 by monoclonal antibodies which recognize ICAM-1 and have been shown to block ICAM-1:fibrinogen interaction.

C. Binding Assay of γ3 Polypeptide to Transfected Chinese Hamster Ovary Cells Expressing ICAM-1

The direct physical interaction of γ3 with ICAM-1 expressed on the surface of CHO cells was investigated.

1) Preparation of Cells

The Chinese Hamster Ovary (CHO) cells were cultivated and as described in Example 8C1. Quantitation of ICAM-1 surface expression on wild-type (WT) CHO cells or on ICAM-1 transfectants was carried out with monoclonal antibodies LB-2 (Clark et al., Human Immunol., 16:100–113 (1986)) or 2D5 (identified in Example 7C). Background fluorescence was determined in the presence of control monoclonal antibody OKM1.

2) Preparation of Labeled Polypeptides

A variant polypeptide γ3 (KYG-γ3) duplicating the fibrinogen γ chain sequence 117–133 N$^{117}$NQKIVNLKEKVAQLEA$^{133}$ (SEQ ID NO 2) was synthesized with the addition of Lys-Tyr-Gly residues at the amino terminus to facilitate radiolabeling of the polypeptide (KYGN$^{117}$NQKIVNLKEKVAQLEA$^{133}$, SEQ ID NO 4). The variant γ3 and L10 polypeptides were synthesized as described in Example 7A. Typically, 2 mg of KYG-γ3 were iodinated with 5 mCi $^{125}$I-Na (Amersham, Arlington Heights, Ill.) by the IODO-GEN method (Fraker et al., Biochem Biophys Res Commun., 80:849–857, (1978)) for 45 min at 4° C. Free radioactivity was separated from polypeptide-bound radioactivity by gel-filtration over a Bio-Gel P-2 column (Bio-Rad, Richmond, Va.) which had been preequilibrated with PBS, pH 7.2, containing 0.01% BSA, with a flow rate of 0.2 ml/sec.

3) Binding Assays of Polypeptides to CHO Cells Expressing ICAM-1

Confluent monolayers of ICAM-1 CHO transfectants or wild type (WT) CHO cells were incubated in serum-free RPMI 1640 medium with increasing concentrations of $^{125}$I-labeled γ3 peptide (10–150 μg/ml) in the presence of 1 mM CaCl$_2$ and 1 mM MgCl$_2$ for 45 min at 22° C. Cells were washed with three rapid changes of serum-free RPMI 1640, solubilized in 10% SDS, and radioactivity associated under the various conditions tested was quantitated in a beta-counter. Non specific binding was assessed in the presence of a 100-fold molar excess unlabeled γ3 peptide, or control peptide L10 added at the start of incubation, and was subtracted from the total as described above.

The specific binding of γ3 to CHO cells expressing ICAM-1 and WT CHO cells was measured to characterize the direct physical interaction of γ3 with ICAM-1. The results of the binding assay are shown in FIG. 13A. The ng of $^{125}$I-γ3 bound per well is plotted on the Y-axis against the peptide concentration (μg/ml) plotted on the X-axis. The results demonstrate that $^{125}$I-labeled γ3 polypeptide bound to ICAM-1 CHO transfectants in a specific and dose-dependent fashion. $^{125}$I-labeled γ3 polypeptide did not bind to WT CHO cells at 50 μg/ml, under the same experimental conditions (FIG. 13B). Binding of the $^{125}$I-labeled γ3 polypeptide was competitively inhibited by a 100-fold molar excess unlabeled γ3, but not by comparable concentrations of control polypeptide L10 (not shown).

9. Preparation of a Monoclonal Anti-γ3 Polypeptide Specific Antibody

A. Preparation of Immunogen

For preparation of a polypeptide immunogen, the synthetic polypeptide γ3 ($N^{117}$NQKIVNLKEKVAQLEA$^{133}$, SEQ ID NO 2) is prepared as described in Example 7A but is modified with a carboxy-terminal cysteine ($N^{117}$NQKIVNLKEKVAQLEA$^{133}$C, SEQ ID NO 3). The synthesized γ3 is coupled to keyhole-limpet-hemocyanin (KLH) (Sigma, St. Louis, Mo.) using the heterobifunctional crosslinking agent, N-succinimidyl-3-(2-pyridyldithio) propionate (SPDP) (Pierce Biochemicals, Rockford, Ill.). For the coupling procedure, 80 microliters (μl) of 10 mg/ml SPDP dissolved in dimethylformamide is admixed dropwise to 400 μl 15 mg/ml KLH in 0.1 M phosphate, 0.1 M NaCl at pH 8.5 under continuous stirring conditions for 30 minutes at 22° C. in order to form SPDP-activated KLH. The resultant SPDP-activated KLH is then extensively dialyzed at 4° C. against a buffered solution of 0.1 M phosphate and 0.1 M NaCl at pH 7.4 in order to remove uncoupled SPDP. Six mg of prepared γ3 having a C-terminal cysteine is first dissolved in 2 ml of 0.1 M phosphate and 0.1 M NaCl at pH 7.4 and then admixed with SPDP-activated KLH prepared above under continuous stirring conditions. The degree of coupling of γ3 with KLH is monitored by the pyridine-2-thione release at 343 nm ($\epsilon$:8.08×10$^3$ M$^{-1}$ cm$^{-1}$) in a spectrophotometer.

B. Preparation of Anti-γ3 Monoclonal Antibodies

Balb/c ByJ mice (Scripps Clinic and Research Foundation Vivarium, La Jolla, Calif.) are immunized and monoclonal antibodies prepared as described in Example 4B. Culture supernatants are collected about two weeks later and assayed for the presence of γ3-specific antibody by solid phase radioimmunoassay (RIA).

Briefly, 50 μl of PBS containing 5 μg/ml of the prepared γ3 immunogen is admixed into the wells of microtiter plates. The plates are maintained overnight (about 16 hours) at 4° C. to permit the γ3 immunogen to adhere to well walls. After washing the wells four times with SPRIA buffer (2.68 mM KCl, 1.47 mM KH$_2$PO$_4$, 137 mM NaCl, 8.03 mM Na$_2$HPO$_4$, 0.05% Tween-20, 0.1 KIU/ml Traysol, 0.1% bovine serum albumin (BSA), 0.015% NaN$_3$), 200 μl of SPRIA buffer containing 3% normal goat serum (NGS) and 3% BSA are admixed to each well to block excess protein binding sites. The plates are maintained for 30 minutes at 20° C., the wells emptied by shaking, and blotted dry to form a solid-support, i.e., a solid matrix to which γ3 immunogen is operatively affixed.

To each well is then admixed 50 μl of hybridoma tissue culture supernatant to form a solid-liquid phase immunoreaction admixture. The admixture is maintained for 2 hours at 37° C. to permit formation of solid-phase immunoreaction products. After washing the wells as described above, 50 μl of $^{125}$I-labelled goat anti-mouse IgG at 0.25 μg protein/ml are admixed to each well to form a labelling reaction admixture. Radioiodination of immunochemically purified goat anti-mouse IgG is performed enzymatically utilizing the IODO-GEN iodination procedure as described in Example 3A1. The resultant admixture is maintained for one hour at 37° C. to permit formation of $^{125}$I-labelled solid-phase immunoreaction products. After washing the wells as described above, the amount of $^{125}$I-labelled product bound to each well is determined by gamma detection.

Hybridomas are selected from hybridoma cultures that secrete anti-γ3 antibodies into their culture media, and further characterized as described herein.

C. Production and Purification of Anti-γ3 Monoclonal Antibodies

Hybridoma anti-γ3 is cultured in a 5% CO$_2$, humidified atmosphere at 37° C. in DMEM containing 2 mM L-glutamine, 50 μg/ml gentamicin, 10% fetal bovine serum, 10% horse serum, all from Grand Island Biological Co., Lawrence, Mass., 10% NCTC medium from Microbiological Associates, Rockville, Md., 1 mM hypoxanthine and 0.3 mM thymidine, both from Sigma Chemical Corp., St. Louis, Mo. Cell concentration is kept in the range of about 1–2×10$^5$ cells per ml of medium to about 1–2×10$^6$ cells per ml of medium for cell growth, division, and production of antibody.

To produce ascites tumor fluid containing anti-γ3 antibody molecules, 10-week old Balb/c mice are immunologically primed by intraperitoneal injection with 0.3 ml of mineral oil and subsequently intraperitoneally injected with 3–5×10$^5$ anti-γ3 hybridoma cells. The inoculated mice are then maintained for a time period sufficient for anti-γ3 antibody-containing ascites tumor fluids to accumulate, e.g., for about 10 to about 21 days. The ascites fluid is collected and clarified by centrifugation at 15,000×g for one hour at 4° C. and stored frozen at −20° C.

Anti-γ3 antibody molecules are isolated from the ascites fluid by subjecting the fluid to fast protein liquid chromatography (FPLC) on a Pharmacia Mono QHR 5/5 anion exchange column in a Pharmacia FPLC System (both from Pharmacia) using a 0–0.5 M NaCl gradient in 10 mM Tris-HCl, pH 8.0, and following the directions supplied with the column. The anti-γ3 antibody molecules so isolated can then be transferred to any physiologically tolerable diluent desired by dialysis.

Alternatively, anti-γ3 antibody molecules can be isolated from the ascites tumor fluid by precipitation with ammonium sulfate according to the method described by Goding, *Monoclonal Antibodies: Principles and Practice*, Academic Press, p100–101 (1983). Briefly, that method entails slowly admixing saturated ammonium sulfate to the ascites fluid until about a 45% to about a 50% ammonium sulfate concentration is achieved. The precipitated immunoglobulins are then collected by centrifugation at 2000×g, preferably 10,000×g. The precipitate is washed 2 or 3 times in 40% saturated ammonium sulfate. The precipitated anti-γ3 antibody molecules are then dialyzed against 500–1000 volumes of phosphate buffered saline (PBS) or any other physiologically tolerable diluent desired to remove ammonium sulfate. The dialysis fluid is changed several times at intervals of a few hours. The protein concentration of the recovered dialyzed anti-γ3 antibody solution is determined by the Lowry method [Lowry et al., *J. Biol. Chem.*, 193, 265–275 (1951)] using a bovine serum albumin standard.

The anti-γ3 antibodies produced are capable of immunoreacting with the immunizing γ3 polypeptide and with fibrinogen, but do not produce detectable immunoreaction above background when using fibrinogen polypeptide derived from other regions of fibrinogen, such as the Mac-1s binding site, e.g., a polypeptide defined by residues 190–202 shown in SEQ ID NO 1.

10. Effect of Plasma Adhesive Proteins on Leukocyte-Endothelium Interaction

The potential role of the plasma adhesive proteins fibrinogen, vitronectin, and fibronectin on mediating leukocyte-endothelium interaction was investigated.

Fibrinogen had previously been shown to increase leukocyte-endothelium interaction (Languino et al., supra). Since two additional plasma proteins, vitronectin and fibronectin, share fibrinogen's adhesive properties, their role in the regulation of cell-cell interaction was investigated. The functional adhesive properties of the plasma proteins were determined in cell attachment assays.

A. Purification of Fibrinogen, Vitronectin, and Fibronectin

Fibrinogen was isolated from fresh plasma and purified from contaminating fibronectin as described in Example 1A. Human fibronectin was purified from plasma as described in Engvall and Ruoslahti, Int. J. Cancer, 10:1–5 (1977). Human vitronectin was purchased from GIBCO (Bethesda, Md.) or donated by Helena Hessle (Telios Pharmaceuticals, San Diego, Calif.). Control proteins transferrin or BSA were purchased from Sigma (St. Louis, Mo.).

B. Preparation of Cells

1) Cell Cultivation

The promyelocytic HL-60 (Collins, Blood, 70:1233–1244 (1987) were cultivated in the same manner as HUVEC in Example 2A. Suspensions of HL-60 were terminally differentiated to a monocyte-like phenotype by a 4 to 5 day culture in the presence of 0.1 $\mu$M 1,25 dihydroxy vitamin $D_3$ (BioMol, Plymouth Meeting, Pa.) and 17.8 $\mu$g/ml indomethacin (Calbiochem, San Diego, Calif.) as described by Collins, supra. The monocytic cell line THP-1 (Tsuchiya et al., Int. J. Cancer, 26:171–176 (1980)) was cultivated in the same manner as HUVEC in Example 2A with the addition of $10^{-5}$ M $\beta$-mercaptoethanol (Eastman Kodak, Rochester, N.Y.).

2) Phenotypic Characterization of Terminally-Differentiated HL-60 Cells

The phenotypical changes in cell surface adhesion receptors during monocytic differentiation of HL-60 cells were quantitated by flow cytometry as described in Languino, et al supra and Example 7C. The monoclonal antibodies used in the assay included the following: BK (also known as LB-2; Becton Dickinson) which recognizes ICAM-1, IB4 which recognizes the $\beta_2$ integrin subunit CD18 (Wright et al., Proc. Natl. Acad. Sci. U.S.A., 85:7734–7738 (1988)), LM609 which recognizes $\alpha_v\beta_3$, OKM1 which recognizes $CD^{11}b$ (Cheresh, Proc. Natl. Acad. Sci. U.S.A., 84:6471–6475 (1987), and 142 which recognizes $\alpha_v$ (D. A. Cheresh, The Scripps Research Institute, San Diego, Calif.).

Results indicated minimal changes in the surface density of the $\beta_2$ integrin subunit CD18 detected by IB4 and $\alpha_v$ detected by 142, an approximate 15–20 fold increase of the $\alpha$ subunit ($\alpha_m$, CD11b) of the leukocyte fibrinogen receptor CD11b/CD18 detected by OKM1, a 6–20 fold increase in $\alpha_v\beta_3$ integrin as detected by LM609 but with considerable heterogeneity, and an approximate 10 fold increase in ICAM-1 as detected by BD.

C. Effect of Fibrinoaen, Vitronectin, and Fibronectin on Leukocvte-Endothelial Interaction 1) Binding Assays The effect of fibrinogen, vitronectin, and fibronectin on the interaction of terminally-differentiated HL-60 and monocytic THP-1 cells with HUVEC was determined as described in Languino, supra. Briefly, serum-free suspensions of HL-60 or THP-1 cells were labeled with $^{51}$Cr as described in Example 81A to a final incorporation of 0.2–4 cpm/cell. After washes in PBS, pH 7.2, aliquots of the HL-60 cells were resuspended in serum-free RPMI 1640 at $1.5\times10^6$/ml and stimulated with 10 $\mu$M of the chemoattractant formyl-methionyl-leucyl-phenylalanine (fMLP, Sigma, St. Louis, Mo.) and equilibrated with 150 $\mu$g/ml fibrinogen, vitronectin, or fibronectin in the presence of 1 mM CaCl2 for 20 min at 22° C. Equilibrated HL-60 were added to resting HUVEC monolayers that had been previously incubated with fresh complete culture medium 12 hours prior to the experiment and incubated for an additional 30 min at 22° C., washed, solubilized in 10–20% SDS, and associated radio-activity determined in a scintillation $\beta$-counter. The number of attached cells was quantitated by diving the cpm harvested by the cpm/cell. Under these experimental conditions, there was no aggregation of the various leukocyte subpopulations in the presence of the different plasma adhesive proteins, nor disruption of the HUVEC monolayers at any time interval tested, as judged by routine microscopic examination of the adhesion field. Data are the mean±S.D. of triplicates from a representative experiment.

2) Time Dependency of Leukocyte-Endothelial Cell Interaction in the Presence of Vitronectin Experimental conditions were the same as described in Example 9C1 except that the 51Cr-labeled HL-60 cells were equilibrated with 40 $\mu$g/ml vitronectin or control protein transferrin and added to resting HUVEC for increasing time intervals between 10 and 60 minutes at 22° C. before measurement of leukocyte adhesion.

3) Concentration Dependency of Leukocyte-Endothelial Cell Interaction in the Presence of Vitronectin Experimental conditions were the same as described in Example 9C1 except that the $^{51}$Cr-labeled HL-60 cells were equilibrated with several concentrations of vitronectin ranging from 1.84 to 150 $\mu$g/ml and prior to incubation to resting HUVEC.

The results of these experiments are shown in FIG. 10. In FIG. 10A, the data is plotted in a bar graph format with the numbers of attached $^{51}$Cr-labeled HL-60 cells on the Y-axis. Terminally differentiated HL-60 cells which had been stimulated with fMLP and equilibrated with fibrinogen, bound to HUVEC at a two to three-fold higher adhesion rate than HL-60 cells which had not been equilibrated with an adhesive protein. These results are in agreement as previously described in Languino et al., supra. Preincubation with comparable concentrations of vitronectin enhanced the adhesion of differentiated HL-60 cells to HUVEC three to four-fold. Equilibration with fibronectin did not result in an increase in adhesion. FIGS. 10B and C demonstrate that vitronectin-mediated increase in differentiated HL-60 cell adhesion to endothelium occurred in a time-and dose-dependent manner and was saturated for physiologic plasma concentrations of vitronectin at 50 $\mu$M/ml.

4) Binding Assays With THP-1 Cells

Binding assays were also performed as described in Example 10C1 described above with THP-1 cells. With comparable concentrations of vitronectin, but not fibronectin, adhesion of monocytic THP-1 cells to resting HUVEC monolayers was demonstrated in a similar time- and dose-dependent manner.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. An antibody or an antigen binding fragment thereof that immunoreacts with amino acid residues 117–133 of fibrinogen γ chain, which amino acid sequence is shown in SEQ ID NO 2, said antibody or said antigen binding fragment thereof, is capable of binding to fibrinogen and inhibiting fibrinogen binding to endothelial cells.

2. The antibody of claim 1 wherein said antibody is monoclonal.

* * * * *